United States Patent
Malinin et al.

(10) Patent No.: US 10,526,274 B2
(45) Date of Patent: Jan. 7, 2020

(54) PROSTACYCLIN COMPOUNDS, COMPOSITIONS AND METHODS OF USE THEREOF

(71) Applicant: Insmed Incorporated, Bridgewater, NJ (US)

(72) Inventors: Vladimir Malinin, Plainsboro, NJ (US); Walter Perkins, Neshanic Station, NJ (US); Franziska Leifer, Princeton, NJ (US); Donna Konicek, Belle Mead, NJ (US); Zhili Li, Kendall Park, NJ (US); Adam Plaunt, Phillipsburg, NJ (US)

(73) Assignee: INSMED INCORPORATED, Bridgewater, NJ (US)

( * ) Notice: Subject to any disclaimer, the term of this patent is extended or adjusted under 35 U.S.C. 154(b) by 0 days.

(21) Appl. No.: 15/994,574

(22) Filed: May 31, 2018

(65) Prior Publication Data

US 2019/0248731 A1 Aug. 15, 2019

Related U.S. Application Data

(63) Continuation of application No. 15/154,631, filed on May 13, 2016, now Pat. No. 10,010,518, which is a continuation of application No. 14/523,538, filed on Oct. 24, 2014, now Pat. No. 9,469,600, which is a continuation of application No. 61/895,680, filed on Oct. 25, 2013.

(60) Provisional application No. 62/042,123, filed on Aug. 26, 2014, provisional application No. 62/028,758, filed on Jul. 24, 2014, provisional application No. 61/950,967, filed on Mar. 11, 2014, provisional application No. 61/910,703, filed on Dec. 2, 2013.

(51) Int. Cl.
| | |
|---|---|
| *C07C 69/734* | (2006.01) |
| *A61K 47/14* | (2017.01) |
| *A61K 47/28* | (2006.01) |
| *A61K 47/24* | (2006.01) |
| *A61K 47/06* | (2006.01) |
| *A61K 9/10* | (2006.01) |
| *A61K 9/51* | (2006.01) |
| *A61K 9/14* | (2006.01) |
| *A61P 9/12* | (2006.01) |
| *A61P 11/00* | (2006.01) |
| *A61K 9/00* | (2006.01) |
| *A61M 15/00* | (2006.01) |
| *A61M 16/14* | (2006.01) |
| *A61K 47/34* | (2017.01) |

(52) U.S. Cl.
CPC .......... *C07C 69/734* (2013.01); *A61K 9/0019* (2013.01); *A61K 9/0043* (2013.01); *A61K 9/0053* (2013.01); *A61K 9/0073* (2013.01); *A61K 9/0075* (2013.01); *A61K 9/0078* (2013.01); *A61K 9/10* (2013.01); *A61K 9/14* (2013.01); *A61K 9/51* (2013.01); *A61K 47/06* (2013.01); *A61K 47/14* (2013.01); *A61K 47/24* (2013.01); *A61K 47/28* (2013.01); *A61K 47/34* (2013.01); *A61M 15/009* (2013.01); *A61M 15/0085* (2013.01); *A61M 16/14* (2013.01); *A61P 9/12* (2018.01); *A61P 11/00* (2018.01); *A61M 2202/064* (2013.01)

(58) Field of Classification Search
CPC .. C07C 69/734; A61K 9/0073; A61K 9/0075; A61K 9/0078; A61K 47/06; A61K 47/14; A61K 47/24; A61M 2202/064; A61P 11/00
USPC .......................................................... 424/40
See application file for complete search history.

(56) References Cited

U.S. PATENT DOCUMENTS

| | | | |
|---|---|---|---|
| 4,367,237 A | 1/1983 | Wakatsuka et al. |
| 4,668,814 A | 5/1987 | Aristoff |
| 4,837,342 A | 6/1989 | Shibasaki et al. |
| 5,153,222 A | 10/1992 | Tadepalli et al. |
| 5,190,972 A | 3/1993 | Dumble |
| 5,234,953 A | 8/1993 | Crow et al. |
| 5,662,932 A | 9/1997 | Amselem et al. |

(Continued)

FOREIGN PATENT DOCUMENTS

| | | |
|---|---|---|
| CN | 101669904 | 3/2010 |
| EP | 0496548 A1 | 7/1992 |

(Continued)

OTHER PUBLICATIONS

Supplementary European Search Report for European Application No. 13859435.3, dated Mar. 29, 2016, 7 pages.

(Continued)

*Primary Examiner* — Yanzhi Zhang
(74) *Attorney, Agent, or Firm* — Cooley LLP

(57) ABSTRACT

Prostacyclin compounds and compositions comprising the same are provided herein. Specifically, prostacyclin compounds comprising treprostinil covalently linked to a linear $C_5$-$C_{18}$ alkyl, branched $C_5$-$C_{18}$ alkyl, linear $C_2$-$C_{18}$ alkenyl, branched $C_3$-$C_{18}$ alkenyl, aryl, aryl-$C_1$-$C_{18}$ alkyl or an amino acid or a peptide (e.g., dipeptide, tripeptide, tetrapeptide) are described. The linkage, in one embodiment, is via a carbamate, amide or ester bond. Prostacyclin compounds provided herein can also include at least one hydrogen atom substituted with at least one deuterium atom. Methods for treating pulmonary hypertension (e.g., pulmonary arterial hypertension) and portopulmonary hypertension are also provided.

41 Claims, 38 Drawing Sheets

(56) References Cited

U.S. PATENT DOCUMENTS

| | | | |
|---|---|---|---|
| 6,054,486 | A | 4/2000 | Crow et al. |
| 6,165,500 | A | 12/2000 | Ceva |
| 6,242,482 | B1 | 6/2001 | Shorr et al. |
| 6,306,435 | B1 | 10/2001 | Chen et al. |
| 6,521,212 | B1 | 2/2003 | Cloutier et al. |
| 6,756,033 | B2 | 6/2004 | Cloutier et al. |
| 6,803,386 | B2 | 10/2004 | Shorr et al. |
| 7,199,157 | B2 | 4/2007 | Wade et al. |
| 7,384,978 | B2 | 6/2008 | Phares et al. |
| 7,417,070 | B2 | 8/2008 | Phares et al. |
| 7,544,713 | B2 | 6/2009 | Phares et al. |
| 7,858,650 | B2 | 12/2010 | Yamamoto et al. |
| 7,879,909 | B2 | 2/2011 | Wade et al. |
| 7,999,007 | B2 | 8/2011 | Jeffs et al. |
| 8,242,305 | B2 | 8/2012 | Batra et al. |
| 8,349,892 | B2 | 1/2013 | Phares |
| 8,350,079 | B2 | 1/2013 | Walsh |
| 8,461,393 | B2 | 6/2013 | Sharma |
| 8,481,782 | B2 | 7/2013 | Batra et al. |
| 8,609,728 | B2 | 12/2013 | Rothblatt et al. |
| 8,969,409 | B2 | 3/2015 | Rothblatt et al. |
| 9,102,660 | B2 | 8/2015 | Batra et al. |
| 9,255,064 | B2 | 2/2016 | Malinin et al. |
| 9,469,600 | B2 | 10/2016 | Malinin et al. |
| 9,593,061 | B2 | 3/2017 | Batra et al. |
| 9,624,156 | B2 | 4/2017 | Phares et al. |
| 10,010,518 | B2 | 7/2018 | Malinin et al. |
| 2003/0022242 | A1 | 1/2003 | Anderson |
| 2003/0108512 | A1* | 6/2003 | Shorr ............. A61K 31/557 424/78.24 |
| 2003/0108743 | A1 | 6/2003 | Anderson |
| 2004/0156816 | A1 | 8/2004 | Anderson |
| 2005/0165111 | A1 | 7/2005 | Wade et al. |
| 2005/0282901 | A1 | 12/2005 | Phares et al. |
| 2005/0282903 | A1 | 12/2005 | Wade et al. |
| 2007/0078095 | A1 | 4/2007 | Phares et al. |
| 2008/0200449 | A1 | 8/2008 | Olschewski et al. |
| 2008/0249167 | A1 | 10/2008 | Phares et al. |
| 2008/0280986 | A1 | 11/2008 | Wade et al. |
| 2009/0036465 | A1 | 2/2009 | Roscigno et al. |
| 2009/0074828 | A1 | 3/2009 | Alexis et al. |
| 2010/0076083 | A1 | 3/2010 | Olschewski et al. |
| 2010/0324313 | A1 | 12/2010 | Hogan et al. |
| 2012/0004307 | A1 | 1/2012 | Wade et al. |
| 2012/0010159 | A1 | 1/2012 | Rothblatt et al. |
| 2012/0216801 | A1 | 8/2012 | Olschewski et al. |
| 2013/0053581 | A1 | 2/2013 | Wei et al. |
| 2013/0184295 | A1 | 7/2013 | Sprague et al. |
| 2013/0261187 | A1 | 10/2013 | Phares et al. |
| 2014/0193379 | A1 | 7/2014 | Jeffs et al. |
| 2014/0256730 | A1 | 9/2014 | Becker et al. |
| 2014/0275262 | A1 | 9/2014 | Phares et al. |
| 2014/0275616 | A1 | 9/2014 | Batra et al. |
| 2014/0323567 | A1 | 10/2014 | Laing |
| 2015/0005374 | A1 | 1/2015 | Phares et al. |
| 2015/0148414 | A1 | 5/2015 | Malinin et al. |
| 2015/0166503 | A1* | 6/2015 | Becker ............. C07C 59/72 514/450 |
| 2015/0175529 | A1 | 6/2015 | Malinin et al. |
| 2015/0328232 | A1 | 11/2015 | Malinin et al. |
| 2016/0256425 | A1 | 9/2016 | Malinin et al. |
| 2016/0318844 | A1 | 11/2016 | Malinin et al. |
| 2017/0049739 | A1 | 2/2017 | Plaunt et al. |
| 2017/0320813 | A1 | 11/2017 | Malinin et al. |

FOREIGN PATENT DOCUMENTS

| | | |
|---|---|---|
| EP | 0989108 A2 | 3/2000 |
| EP | 1161234 B1 | 7/2003 |
| EP | 1045695 B1 | 3/2004 |
| EP | 1696932 B1 | 9/2009 |
| EP | 1744739 B1 | 3/2010 |
| EP | 1696900 B1 | 7/2010 |
| EP | 2461812 B1 | 1/2014 |
| EP | 2792353 A2 | 10/2014 |
| EP | 2200650 B1 | 1/2016 |
| JP | S61-289034 | 12/1986 |
| JP | H08-507515 | 8/1996 |
| JP | 2002-521423 | 7/2002 |
| JP | 2002-539154 | 11/2002 |
| JP | 2006-528969 | 12/2006 |
| JP | 2008-507585 | 3/2008 |
| JP | 2009-519972 | 5/2009 |
| JP | 2009-537246 | 10/2009 |
| JP | 2012-516187 | 7/2012 |
| WO | WO 99/033490 | 7/1999 |
| WO | WO 2000/006120 | 2/2000 |
| WO | WO 2000/057701 | 10/2000 |
| WO | WO 2004/103348 | 12/2004 |
| WO | WO 2005/007081 | 1/2005 |
| WO | WO 2008/098196 | 8/2008 |
| WO | WO 2009/152160 | 12/2009 |
| WO | WO 2009/158010 | 12/2009 |
| WO | WO 2010/036798 | 4/2010 |
| WO | WO 2010/039531 | 4/2010 |
| WO | WO 2010/129757 | 11/2010 |
| WO | WO 2011/003058 | 1/2011 |
| WO | WO 2011/022707 | 2/2011 |
| WO | WO 2011/089215 | 7/2011 |
| WO | WO 2011/089216 | 7/2011 |
| WO | WO 2011/153363 | 12/2011 |
| WO | WO 2012/009816 | 1/2012 |
| WO | WO 2012/107364 | 8/2012 |
| WO | WO 2012/111627 | 8/2012 |
| WO | WO 2012/124688 | 9/2012 |
| WO | WO 2013/024047 | 2/2013 |
| WO | WO 2013/024048 | 2/2013 |
| WO | WO 2013/024049 | 2/2013 |
| WO | WO 2013/024051 | 2/2013 |
| WO | WO 2013/024052 | 2/2013 |
| WO | WO 2013/024053 | 2/2013 |
| WO | WO 2013/174848 | 11/2013 |
| WO | WO 2014/022373 | 2/2014 |
| WO | WO 2014/022376 | 2/2014 |
| WO | WO 2014/085813 | 6/2014 |
| WO | WO 2014/110094 | 7/2014 |
| WO | WO 2014/110491 | 7/2014 |
| WO | WO 2014/203278 | 12/2014 |
| WO | WO 2015/061720 | 4/2015 |
| WO | WO 2015/138423 | 9/2015 |
| WO | WO 2015/192030 | 12/2015 |
| WO | WO 2016/081658 | 5/2016 |
| WO | WO 2017/223400 | 12/2017 |

OTHER PUBLICATIONS

International Search Report and Written Opinion for International Application No. PCT/US2013/072647, dated Apr. 4, 2014, 9 pages.

International Search Report and Written Opinion for International Application No. PCT/US2015/019661, dated Jun. 3, 2015, 10 pages.

Extended European Search Report for European Application No. 14855785.3, dated May 22, 2017, 9 pages.

International Search Report and Written Opinion for International Application No. PCT/US2014/062232, dated Apr. 23, 2015, 11 pages.

Extended European Search Report for European Application No. 15862092.2, dated May 25, 2018, 8 pages.

International Search Report and Written Opinion for International Application No. PCT/US2015/061427, dated Feb. 2, 2016, 9 pages.

International Search Report and Written Opinion for International Application No. PCT/US2017/038932, dated Sep. 21, 2017, 10 pages.

Channick, R. N. et al., "Inhaled treprostinil: a therapeutic review," Drug Design, Development and Therapy, 2012:6, p. 19-28.

Kleemann, E. et al., "Iloprost-containing liposomes for aerosol application in pulmonary arterial hypertension: formulation aspects and stability," Pharmaceutical Research, 24(2):277-287, Feb. 2007, Epub Dec. 2006.

Kuo, Y-C. et al., "Physicochemical properties of nevirapine-loaded solid lipid nanoparticles and nanostructured lipid carriers," Colloids and Surfaces B: Biointerfaces 83 (2011) 299-306.

(56) References Cited

OTHER PUBLICATIONS

Leifer, F. et al., "Prolonged activity of inhaled treprostinil prodrug nanoparticles in a rat model of pulmonary arterial hypertension," Poster presented at the European Respiratory Society (ERS) International Congress, Sep. 6-10, 2014, Munich, Germany. Retrieved from the Internet: <URL: http://www.insmed.com/pdf/3-ProlongedInhaledTreprostinil.pdf>. [Retrieved on May 4, 2017], 1 page.

Lehofer, B., Master's Thesis, "Investigation of liposomal formulations suitable for pulmonary application of iloprost with different nebulizer devices," Graz University of Technology, Feb. 2013, [Online], Retrieved from the Internet: <URL: http://diglib.tugraz.at/download.php?id=576a742a427d7&location=browse>, 117 pages.

Mayo Clinic [online], "Pulmonary Fibrosis, Symptoms and Causes," Retrieved from the Internet on Dec. 15, 2016, <URL: http://www.mayoclinic.org/diseases-conditions/pulmonary-fibrosis/symptoms-causes/dxc-20211754>, 5 pages.

McLaughlin, V. V. et al., "Addition of inhaled treprostinil to oral therapy for pulmonary arterial hypertension," Journal of the American College of Cardiology, 55(18):1915-1922 (2010).

Moriarty, R. M. et al., "The intramolecular asymmetric pauson-khand cyclization as a novel and general stereoselective route to benzindene prostacyclins: synthesis of UT-15 (treprostinil)," J. Org. Chem., 69(6):1890-1902 (2004).

Muller, R. H. et al., "Solid lipid nanoparticles (SLN) for controlled drug delivery—a review of the state of the art," European Journal of Pharmaceutics and Biopharmaceutics, 50 (2000) 161-177.

Poms, A. et al., "Inhaled Treprostinil for the treatment of Pulmonary Arterial Hypertension," Critical Care Nurse, 31(6):e1-e11 (2009).

Provencher, S., "Long-term treprostinil in pulmonary arterial hypertension: is the glass half full or half empty?," Eur. Respir. J., 28(6):1073-1075 (2006).

Saleemi, S., "Portopulmonary hypertension," Ann. Thorac Med., 5(1):5-9 (Jan.-Mar. 2010).

Skoro-Sajer, N. et al., "Treprostinil for pulmonary hypertension," Vascular Health and Risk Management, 4(3):507-513 (2008).

Sorbera, L. A. et al., "UT-15. Treatment of pulmonary hypertension treatment of peripheral vascular disease," Drug of the Future, 26(4):364-374 (2001).

PubChem Substance of Record for UNII-8GJK87S89F, PubChem CID: 91617675, published online Mar. 18, 2015, pp. 1-8.

Mosgoeller, W. et al., "Nanoparticle-Mediated Treatment of Pulmonary Arterial Hypertension," Chapter 17 In: Methods in Enzymology, vol. 508, (2012) pp. 325-354.

Oberdorster, G. et al., "Nanotoxicology: An emerging discipline evolving from studies of ultrafine particles," Environmental Health Perspectives, vol. 113, No. 7, pp. 823-839 (Jul. 2005).

Vieira, D. B. et al., "Assembly of a model hydrophobic drug into cationic bilayer fragments," Journal of Colloid and Interface Science, vol. 293, pp. 240-247 (2006).

Sriwongsitanont, S. et al., "Effect of PEG Lipid (DSPE-PEG2000) and freeze-thawing process on the phospholipid vesicle size and lamellarity," Colloid Polymer Science, vol. 282, No. 7, pp. 753-760 (May 2004); published online Dec. 3, 2003.

\* cited by examiner

PROSTACYCLIN COMPOUNDS, COMPOSITIONS AND METHODS OF USE THEREOF

CROSS REFERENCE TO RELATED APPLICATIONS

This application is a continuation of U.S. patent application Ser. No. 15/154,631, filed May 13, 2016, which is a continuation of U.S. patent application Ser. No. 14/523,538, now U.S. Pat. No. 9,469,600, filed Oct. 24, 2014, which claims priority from U.S. Provisional Application Ser. No. 62/042,123, filed Aug. 26, 2014; 62/028,758, filed Jul. 24, 2014; 61/950,967, filed Mar. 11, 2014; 61/910,703, filed Dec. 2, 2013; 61/895,680, filed Oct. 25, 2013; each of which is incorporated by reference in its entirety for all purposes.

BACKGROUND OF THE INVENTION

Pulmonary hypertension (PH) is characterized by on abnormally high blood pressure in the lung vasculature. It is a progressive, lethal disease that leads to heart failure and can occur in the pulmonary artery, pulmonary vein, or pulmonary capillaries. Symptomatically patients experience shortness of breath, dizziness, fainting, and other symptoms, all of which are made worse by exertion. There are multiple causes, and can be of unknown origin, idiopathic, and can lead to hypertension in other systems, for example, portopulmonary hypertension in which patients have both portal and pulmonary hypertension.

Pulmonary hypertension has been classified into five groups by the World Health Organization (WHO). Group I is called pulmonary arterial hypertension (PAH), and includes PAH that has no known cause (idiopathic), inherited PAH (i.e., familial PAH or FPAH), PAH that is caused by drugs or toxins, and PAH caused by conditions such as connective tissue diseases, HIV infection, liver disease, and congenital heart disease. Group II pulmonary hypertension is characterized as pulmonary hypertension associated with left heart disease. Group III pulmonary hypertension is characterized as PH associated with lung diseases, such as chronic obstructive pulmonary disease and interstitial lung diseases, as well as PH associated with sleep-related breathing disorders (e.g., sleep apnea). Group IV PH is PH due to chronic thrombotic and/or embolic disease, e.g., PH caused by blood clots in the lungs or blood clotting disorders. Group V includes PH caused by other disorders or conditions, e.g. blood disorders (e.g., polycythemia vera, essential thrombocythemia), systemic disorders (e.g., sarcoidosis, vasculitis), metabolic disorders (e.g., thyroid disease, glycogen storage disease).

Pulmonary arterial hypertension (PAH) afflicts approximately 200,000 people globally with approximately 30,000-40,000 of those patients in the United States. PAH patients experience constriction of pulmonary arteries which leads to high pulmonary arterial pressures, making it difficult for the heart to pump blood to the lungs. Patients suffer from shortness of breath and fatigue which often severely limits the ability to perform physical activity.

The New York Heart Association (NYHA) has categorized PAH patients into four functional classes, used to rate the severity of the disease. Class I PAH patients as categorized by the NYHA, do not have a limitation of physical activity, as ordinary physical activity does not cause undue dyspnoea or fatigue, chest pain, or near syncope. Treatment is not needed for class I PAH patients. Class II PAH patients as categorized by the NYHA have a slight limitation on physical activity. These patients are comfortable at rest, but ordinary physical activity causes undue dyspnoea or fatigue, chest pain or near syncope. Class III PAH patients as categorized by the NYHA have a marked limitation of physical activity. Although comfortable at rest, class III PAH patients experience undue dyspnoea or fatigue, chest pain or near syncope as a result of less than ordinary physical activity. Class IV PAH patients as categorized by the NYHA are unable to carry out any physical activity without symptoms. Class IV PAH patients might experience dyspnoea and/or fatigue at rest, and discomfort is increased by any physical activity. Signs of right heart failure are often manifested by class IV PAH patients.

Patients with PAH are treated with an endothelin receptor antagonist (ERA), phosphodiesterase type 5 (PDE-5) inhibitor, a guanylate cyclase stimulator, a prostanoid (e.g., prostacyclin), or a combination thereof. ERAs include abrisentan (Letairis®), sitaxentan, bosentan (Tracleer®), and macitentan (Opsumit®) PDE-5 inhibitors indicated for the treatment of PAH include sildenafil (Revatio®), tadalafil (Adcirca®). Prostanoids indicated for the treatment of PAH include iloprost, epoprosentol and treprostinil (Remodulin®, Tyvaso®). The one approved guanylate cyclase stimulator is riociguat (Adempas®). Additionally, patients are often treated with combinations of the aforementioned compounds.

Portopulmonary hypertension is defined by the coexistence of portal and pulmonary hypertension, and is a serious complication of liver disease. The diagnosis of portopulmonary hypertension is based on hemodynamic criteria: (1) portal hypertension and/or liver disease (clinical diagnosis-ascites/varices/splenomegaly), (2) mean pulmonary artery pressure>25 mmHg at rest, (3) pulmonary vascular resistance>240 dynes s/cm$^5$, (4) pulmonary artery occlusion pressure>15 mmHg or transpulmonary gradient>12 mmHg. PPH is a serious complication of liver disease, and is present in 0.25 to 4% of patients suffering from cirrhosis. Today, PPH is comorbid in 4-6% of those referred for a liver transplant.

Despite there being treatment for PAH and PPH, the current prostacyclin therapies are associated with severe toxicity and tolerability issues, as well as the requirement for inconvenient dosing schedules. The present invention overcomes addresses these factors by providing compounds and treatment schedules that provide for less toxicity, better tolerability and more convenient dosing schedules.

SUMMARY OF THE INVENTION

In one aspect of the invention, a prostacyclin compound of Formula (I), or a pharmaceutically acceptable salt, is provided:

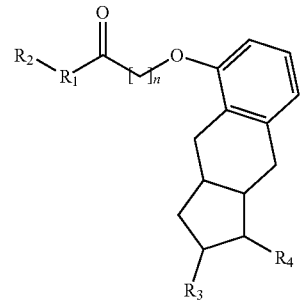

Formula (I)

wherein $R_1$ is NH, O or S; $R_2$ is H, a linear $C_5$-$C_{18}$ alkyl, branched $C_5$-$C_{18}$ alkyl, linear $C_2$-$C_{18}$ alkenyl, branched $C_3$-$C_{18}$ alkenyl, aryl, aryl-$C_1$-$C_{18}$ alkyl; an amino acid or a peptide; $R_3$ is H, OH, O-alkyl or O-alkenyl; $R_4$ is an optionally substituted linear or branched $C_1$-$C_{15}$ alkyl, or an optionally substituted linear or branched $C_2$-$C_{15}$ alkenyl; and n is an integer from 0 to 5, with the proviso that the prostacyclin compound is not treprostinil.

In another aspect of the invention, a prostacyclin compound of Formula (II), or a pharmaceutically acceptable salt, is provided:

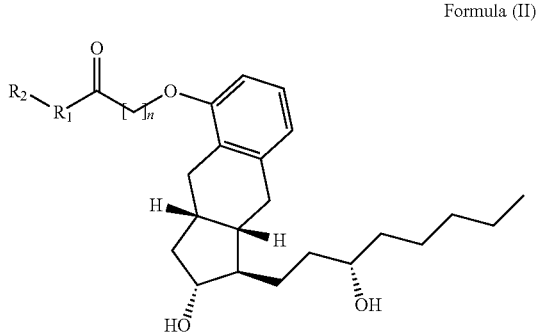

Formula (II)

wherein $R_1$ is NH, O or S; $R_2$ is a linear or branched $C_5$-$C_{18}$ alkyl, a linear $C_2$-$C_{18}$ alkenyl or a branched $C_3$-$C_{18}$ alkenyl, aryl, aryl-$C_1$-$C_{18}$ alkyl, an amino acid or a peptide; and n is an integer from 0 to 5.

In one embodiment, a compound of Formula (I) and/or (II) is provided, wherein one or more hydrogen atoms is substituted with a deuterium. Accordingly, in one embodiment, the present invention relates to an isotopologue of formula (I) and/or (II), substituted with one or more deuterium atoms. The isotopologue of Formula (I) and/or (II) may be used to accurately determine the concentration of compounds of Formula (I) and/or (II) in biological fluids and to determine metabolic patterns of compounds of Formula (I) and/or (II) and its isotopologues. The invention further provides compositions comprising these deuterated isotopologues and methods of treating diseases and conditions, as set forth herein.

In one embodiment of the invention a compound of Formula (I) or (II), or a pharmaceutically acceptable salt, is provided, wherein $R_1$ is N and n is 1. In a further embodiment, $R_2$ is a linear $C_5$-$C_{18}$ alkyl or a branched $C_5$-$C_{18}$ alkyl. In a further embodiment, $R_2$ is a linear $C_6$-$C_{12}$ alkyl or a branched $C_6$-$C_{12}$ alkyl.

Another embodiment of the invention provides a compound of Formula (I) or (II), wherein $R_1$ is O and n is 1. In another embodiment, a compound of Formula (I) or (II) is provided, wherein $R_1$ is S and n is 1. In yet another embodiment of the invention, a compound of Formula (I) or (II) is provided, wherein $R_1$ is N and n is 0.

Another embodiment of the invention provides a prostacyclin compound of Formula (I) or (II), wherein $R_2$ is a linear $C_5$-$C_{18}$ alkyl. In a further embodiment, n is 0 or 1. In even a further embodiment, $R_1$ is N or O. In yet a further embodiment, $R_2$ is a linear $C_6$-$C_{16}$ alkyl. Yet another embodiment provides a prostacyclin compound of Formula (I) or (II), wherein $R_1$ is N, $R_2$ is a linear $C_6$-$C_{18}$ alkyl, and n is 1. In even a further embodiment, $R_2$ is a linear $C_6$, $C_8$, $C_{10}$, $C_{12}$, or $C_{14}$ alkyl.

Another embodiment of the invention provides a prostacyclin compound of Formula (I) or (II), or a pharmaceutically acceptable salt, wherein $R_2$ is a branched $C_5$-$C_{18}$ alkyl. In a further embodiment, n is 0 or 1. In yet a further embodiment, $R_1$ is N or O. In even a further embodiment, the branched alkyl is hexyl, octyl, decyl, dodecyl, tetradecyl, hexadecyl or octadecyl.

In yet another embodiment, a prostacyclin compound of formula (I) or (II), or a pharmaceutically acceptable salt, is provided, wherein $R_2$ is a linear $C_5$-$C_{18}$ alkenyl. In a further embodiment, n is 0 or 1. In yet a further embodiment, $R_1$ is N or O. In even a further embodiment, the branched alkyl is hexyl, octyl, decyl, dodecyl, tetradecyl, hexadecyl or octadecyl.

In yet another embodiment, a prostacyclin compound of Formula (I) or (II), or a pharmaceutically acceptable salt, is provided, wherein $R_2$ is a branched $C_5$-$C_{18}$ alkenyl. In a further embodiment, n is 0 or 1. In yet a further embodiment, $R_1$ is N or O. In yet a further embodiment, the branched alkenyl is pentenyl, hexenyl, heptenyl, octenyl, nonenyl, decenyl, undecenyl, dodecenyl, tridecenyl, tetradecenyl, pentadecenyl, hexadecenyl, heptadecenyl or octadecenyl.

In one embodiment, a prostacyclin compound of Formula (I) or (II), or a pharmaceutically acceptable salt, is provided, wherein $R_2$ is a branched chain alkyl that is either a symmetrical branched alkyl or an asymmetrical branched alkyl. In one embodiment of Formula (I) or (II), $R_1$ is O or N and $R^2$ is

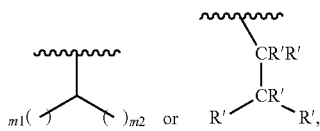

where m1 and m2 are independently an integer selected from 1 to 9 and each occurrence of R' is independently H, a linear or branched $C_1$-$C_8$ alkyl, or a linear or branched $C_1$-$C_8$ alkenyl. When m1 and/or m2 is an integer from 2-9, the m1/m2 at the end of the carbon chain is $CH_3$, while the remaining m1/m2 groups are $CH_2$. In a further embodiment, n is 0 or 1. In even a further embodiment, n is 1, $R_1$ is O, $R_2$ is

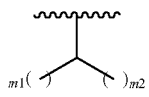

and the following compound is provided:

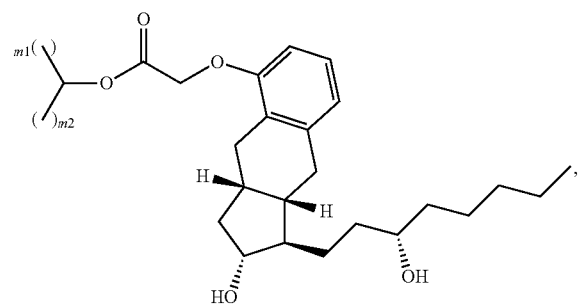

or a pharmaceutically acceptable will thereof. In one embodiment, m1 and m2 are both 4. In another embodiment, m1 is 3 and m2 is 4. In even a further embodiment, n is 1.

In one embodiment, a compound of Formula (I) or (II) is provided, $R_1$ is O and $R_2$ is

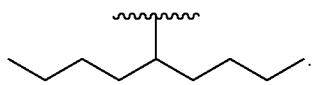 [SMILES: *C(CCCC)CCCC]

In yet another embodiment of Formula (I) or (II), $R_1$ is O and $R_2$ is

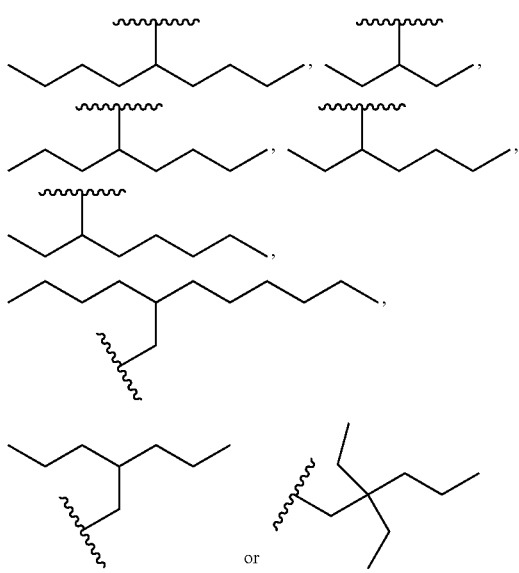

In one embodiment, a compound of Formula (I) or (II) is provided, $R_1$ is N and $R_2$ is

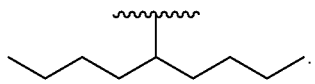

In yet another embodiment of Formula (I) or (II), $R_1$ is N and $R_2$ is

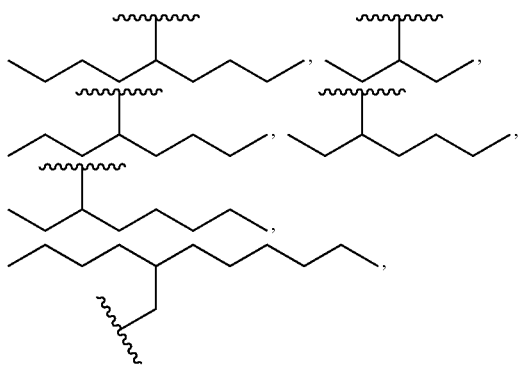

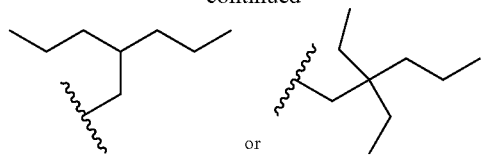

In a further embodiment, n is 1 and the following compound is provided:

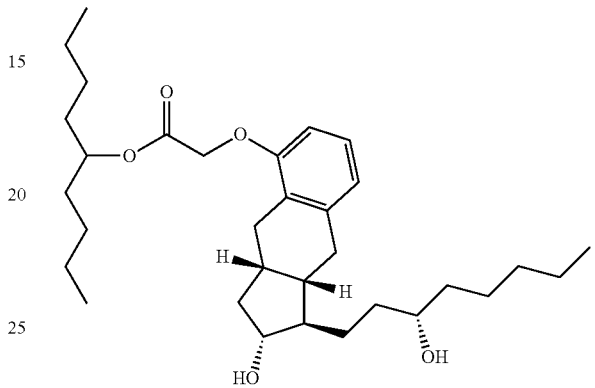

(referred to herein as 5-nonanyl-treprostinil or 5C9-TR).

In one embodiment, the prostacyclin compounds of the formulae provided herein having a branched alkyl or branched alkenyl (e.g., where $R_2$ of the formulae provided herein is 5-nonanyl, 3-heptyl, 4-heptyl, 4-octyl, 3-octyl, 2-octyl, 2-dimethyl-1-propyl, 3,3-dimethyl-1-butyl, 2-ethyl-1-butyl, 3-pentyl) at position $R_2$ exhibit a slower conversion rate relative to a prostacyclin compound having a linear alcohol chain at position $R_2$, and have the further advantage of high solubility.

Yet another embodiment of the invention relates to a prostacyclin compound of Formula (III), or a pharmaceutically acceptable salt.

Formula (III)

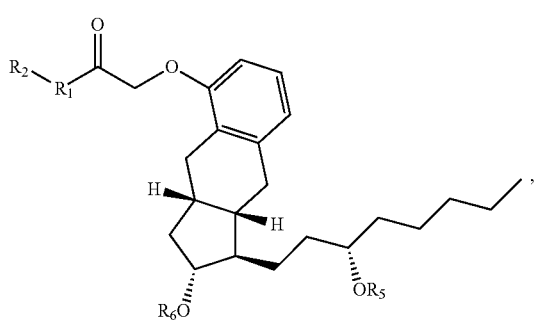

wherein $R_1$ and $R_2$ are defined above, and $R_5$ and $R_6$ are independently selected from H, optionally substituted linear or branched $C_1$-$C_{15}$ alkyl, optionally substituted linear or branched $C_2$-$C_{15}$ alkenyl, (C=O)-optionally substituted linear or branched $C_1$-$C_{15}$ alkyl or (C=O)-optionally substituted linear or branched $C_2$-$C_{15}$ alkenyl, with the proviso that the prostacyclin compound of Formula (III) is not treprostinil.

Another aspect of the invention relates to a prostacyclin composition comprising a prostacyclin compound of Formula (I), (II) or (III). In one embodiment, the prostacyclin composition comprises a prostacyclin compound of Formula (I), (II) or (III) and a hydrophobic additive. In a further embodiment, the hydrophobic additive is a hydrocarbon, a terpene or a hydrophobic lipid. In another embodiment, the hydrophobic additive is cholesteryl acetate, ethyl stearate, palmitate, myristate, palmityl palmitate, tocopherol acetate, a monoglyceride, a diglyceride, a triglyceride like palmitate, myristate, dodecanoate, decanoate, octanoate or squalane. In even a further embodiment, the hydrophobic additive is squalane.

In another aspect of the invention, a composition comprising a prostacyclin compound of Formula (I), (II) or (III), and an amphiphilic agent is provided. In one embodiment, the amphiphilic agent is a PHGylated lipid, a surfactant or a block copolymer. In a further embodiment, the prostacyclin composition comprises a prostacyclin compound of Formula (I), (II) or (III), and a PEGylated lipid. In a further embodiment, the PEGylated lipid comprises PEG400, PEG500, PEG1000, PEG2000, PEG3000, PEG4000, or PEG5000. In a further embodiment the lipid component of the PEGylated lipid comprises PEG covalently linked to dimyristoyl phosphatidylethanolamine (DMPE), dipalmitoyl phosphoethanolamine (DPPE), distearoylphosphatidylethanolamine (DSPE), dimyristoylglycerol glycerol (DMG), diphosphatidylglycerol (DPG), disteraroylglycerol (DSG).

In another embodiment of the invention, a composition comprising a prostacyclin compound of Formula (I), (II) or (III), a hydrophobic additive and an amphiphilic agent is provided. In one embodiment, the amphiphilic agent is a PEGylated lipid, a surfactant or a block copolymer. In a further embodiment, the hydrophobic additive is squalene. In a further embodiment, a PEGylated lipid is present in the composition and comprises PBG400, PEG500, PEG1000, PEG2000, PEG3000, PEG4000 or PEG5000.

In another aspect of the invention, a method for treating pulmonary hypertension (PH) is provided. The treatment methods include treatment of group I (PAH), group II, group III, group IV or group V PH. In one embodiment, the method for treating PH comprises treatment of pulmonary arterial hypertension (PAH) in a patient in need thereof. In one embodiment, the method for treating PAH comprises administering to the patient in need of treatment, a prostacyclin compound of Formula (I), (II) or (III), or a pharmaceutically acceptable salt thereof, or a composition comprising a prostacyclin compound of Formula (I), (II) or (III), or a pharmaceutically acceptable salt thereof. In a further embodiment, the administration is subcutaneous, oral, nasal, intravenous or a pulmonary route of administration. In the case of pulmonary administration, the compound of Formula (I), (II) or (III), or the composition comprising the prostacyclin compound of Formula (I), (II) or (III) is administered to the patient via a nebulizer, dry powder inhaler, or metered dose inhaler.

In another aspect of the invention, a method for treating portopulmonary hypertension (PPH) in a patient in need thereof is provided. In one embodiment, the method for treating PPH comprises administering to the patient in need of treatment, a prostacyclin compound of Formula (I), (II) or (III), or a pharmaceutically acceptable salt thereof, or a composition comprising a prostacyclin compound of Formula (I), (II) or (III), or a pharmaceutically acceptable salt thereof. In a further embodiment, the administration is subcutaneous, oral, nasal, intravenous or a pulmonary route of administration. In the case of pulmonary administration, the compound of Formula (I), (II) or (III), or a pharmaceutically acceptable salt thereof, or the composition comprising the prostacyclin compound of Formula (I), (II) or (III) is administered to the patient via a nebulizer, dry powder inhaler, or metered dose inhaler.

In one embodiment of the invention, a method for treating PH, PAH or PPH in a patient in need thereof is provided, comprises administering to the lungs of the patient a prostacyclin compound of Formula (I), (II) or (III), or a pharmaceutically acceptable salt thereof, via a metered dose inhaler comprising a propellant. In a further embodiment, the propellant is a fluorocarbon. In one embodiment the compound of Formula (I), (II) or (III) or pharmaceutically acceptable salt thereof is administered via a metered dose inhaler to the lungs of a patient in need of PH, PAH or PPH treatment, and administration occurs once, twice or three limes daily. In embodiments where the compound of Formula (I), (II) or (III), or a composition comprising the compound of Formula (I), (II) or (III), is administered orally, nasally, subcutaneously, intravenously or to the lungs (e.g., via nebulization, dry powder inhaler or metered dose inhaler), administration to the patient is either once or twice daily. In one embodiment, the compound of Formula (I), (II) or (III), or a composition comprising the compound of Formula (I), (II) or (III) is administered once daily to the patient in need of treatment, and administration is subcutaneous, intravenous, oral, nasal, or to the lungs via aerosolization using a nebulizer, dry powder inhaler, or metered dose inhaler.

In one embodiment, the patient treated for PH, PAH or PPH with the compounds, compositions and methods described herein experiences a decreased number of side effect(s), or a reduction in severity of side effect(s), compared to the number of side effect(s) or severity of side effect(s) experienced when the patient is administered treprostinil. In one embodiment, the side effect is the patient's cough response, and the frequency and/or severity is reduced, as compared to the frequency and/or severity of cough response experienced by the patient when administered treprostinil.

In another embodiment, the prostacyclin compound administered to a patient in need thereof via a pulmonary route by the PH, PAH or PPH treatment methods described herein provides a greater pulmonary elimination half-life ($t_{1/2}$) of the prostacyclin compound and/or its metabolite treprostinil, compared to the pulmonary elimination half-life ($t_{1/2}$) of treprostinil, when treprostinil is administered via a pulmonary route (e.g., by nebulization, dry powder inhaler, or a metered dose inhaler) to the patient.

In another embodiment, the prostacyclin compound administered to a patient in need thereof, via the PH, PAH or PPH treatment methods described herein provides a greater systemic half-life ($t_{1/2}$) of the prostacyclin compound and/or its metabolite treprostinil, compared to the systemic elimination half-life ($t_{1/2}$) of treprostinil, when treprostinil is administered to the patient. In a further embodiment, administration of the prostacyclin compound and treprostinil comprises subcutaneous or intravenous administration.

In another embodiment, the prostacyclin compound administered to a patient in need of PH, PAH or PPH treatment provides a greater mean pulmonary $C_{max}$ and/or lower plasma $C_{max}$ of treprostinil for the patient, compared to the respective pulmonary or plasma $C_{max}$ of treprostinil, when treprostinil is administered to the patient.

In another embodiment, the prostacyclin compound administered to a patient in need of PH (e.g., PAH) or PPH treatment provides a greater mean pulmonary or plasma area under the curve ($AUC_{0-t}$) of the prostacyclin compound and/or its metabolite treprostinil, compared to the mean pulmonary or plasma area under the curve ($AUC_{0-t}$) of treprostinil, when treprostinil is administered to the patient. In yet another embodiment, the prostacyclin compound administered to a patient in need thereof provides a greater pulmonary or plasma time to peak concentration ($t_{max}$) of the prostacyclin compound and/or its metabolite treprostinil, compared to the pulmonary or plasma time to peak concentration ($t_{max}$) of treprostinil, when treprostinil is administered to the patient.

BRIEF DESCRIPTION OF THE FIGURES

FIG. 18, bottom panel, shows the EC50 of $5C_9$-TR over time, calculated from the cAMP response of CHO-K1 cells vs. 5C9-TR.

FIG. 19, bottom panel, shows the EC50 of $C_{14}$-TR overtime, calculated from the cAMP response of CHO-K1 cells vs. $C_{14}$-TR.

FIG. 20, bottom panel, shows the EC50 of $C_{16}$-TR overtime, calculated from the cAMP response of CHO-K1 cells vs. $C_{16}$-TR.

Figure 23:
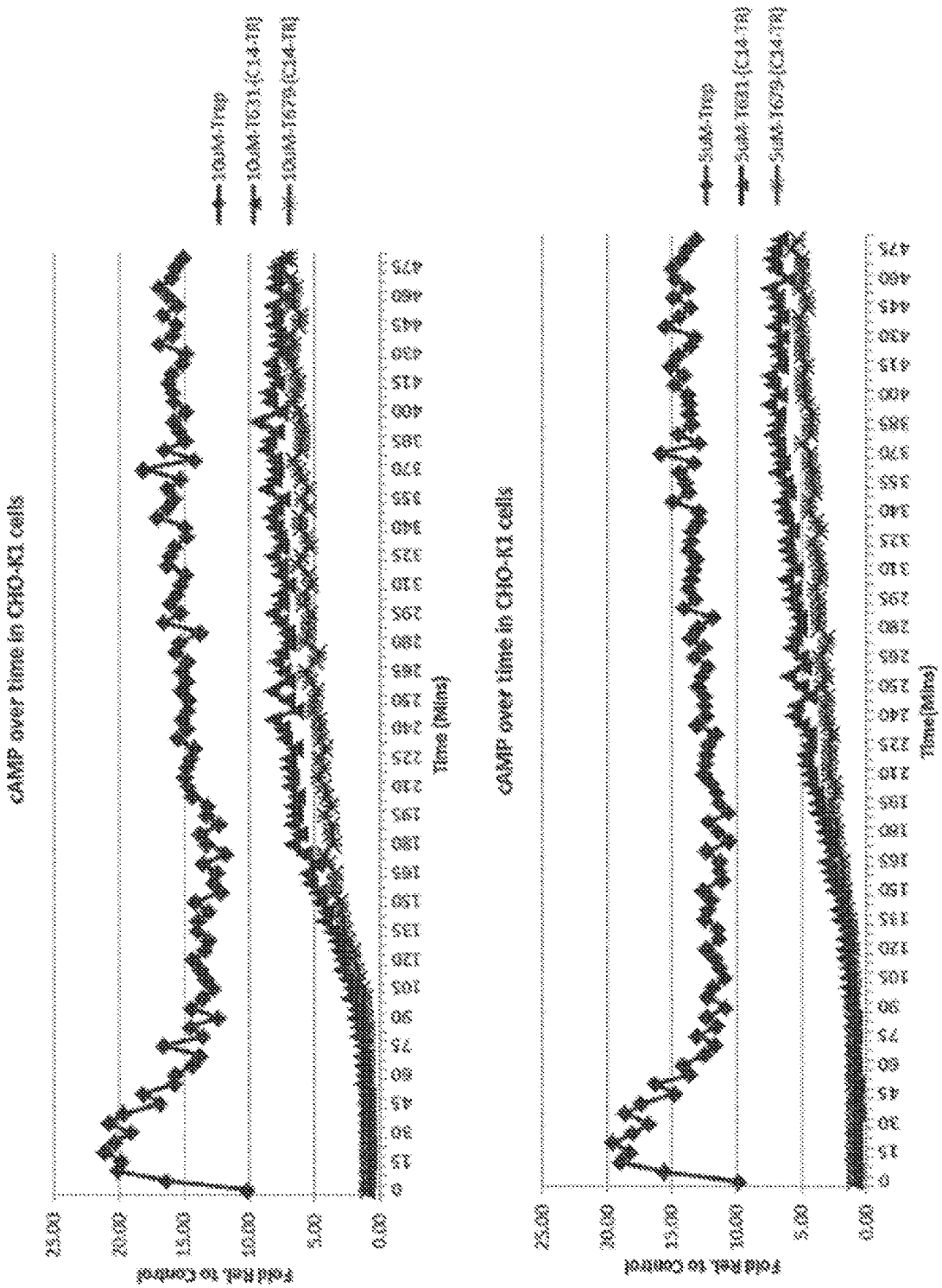

FIG. 23 is a graph of relative cAMP response of CHO-K1 cells vs. time, in response to challenge with treprostinil, T631 ($C_{14}$-TR 40 mol %, squalane 40 mol %, chol-PEG2k 10 mol %, DOPC 10 mol %), or T679 ($C_{14}$-TR 45 mol %, squalane 45 mol %, chol-PEG2k 10 mol %) at 10 µM (top panel) or 5 µM (bottom panel).

Figure 24:
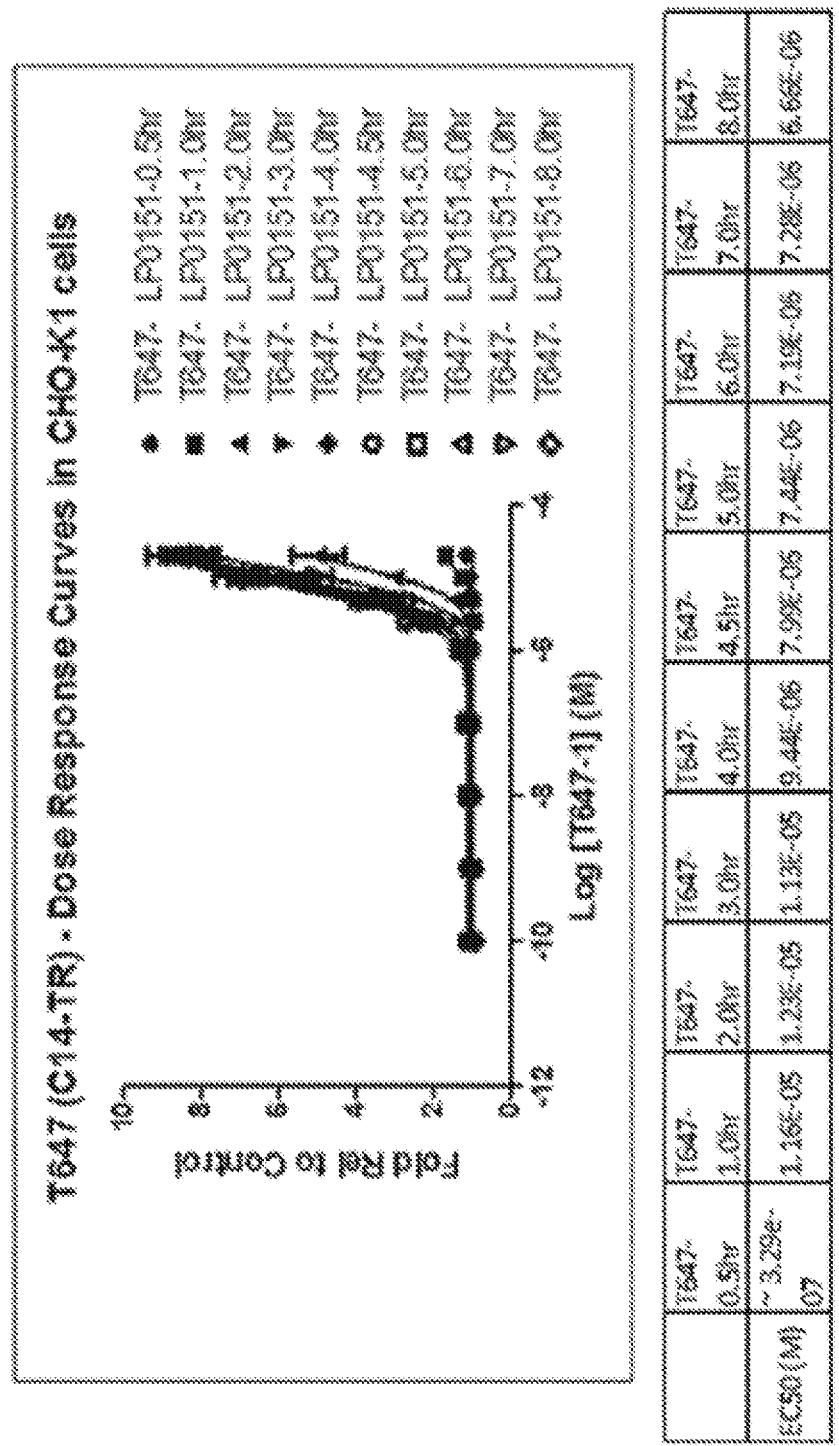

FIG. 24, top panel, is a graph of relative cAMP response of CHO-K1 cells vs. T647 ($C_{14}$-TR 90 mol %, chol-PEG2k 10 mol %) treprostinil alkyl ester composition challenge, at various dosages and time points. FIG. 24, bottom panel, shows the EC50 of T647 over time, calculated from the cAMP responses of CHO-K1 cells v. T647-TR.

Figure 25:
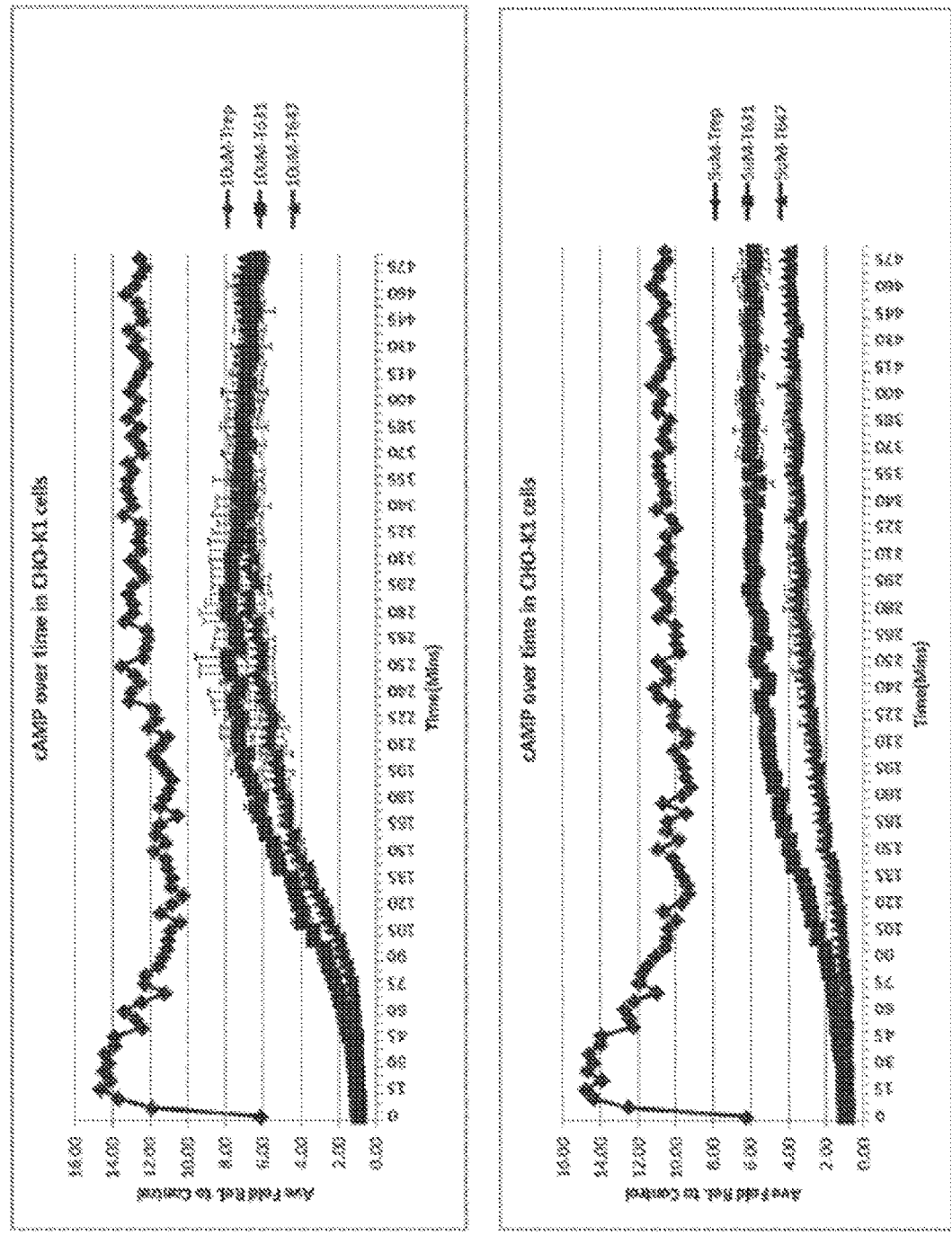

FIG. 25 are graphs of relative cAMP response of CHO-K1 cells vs. time, in response to challenge with treprostinil, T631 ($C_{14}$-TR 40 mol %, squalane 40 mol %, chol-PEG2k 10 mol %, DOPC 10 mol %), or T647 ($C_{14}$-TR 90 mol %, chol-PEG2k 10 mol %) at 10 µM (top panel) or 5 µM (bottom panel).

Figure 26:
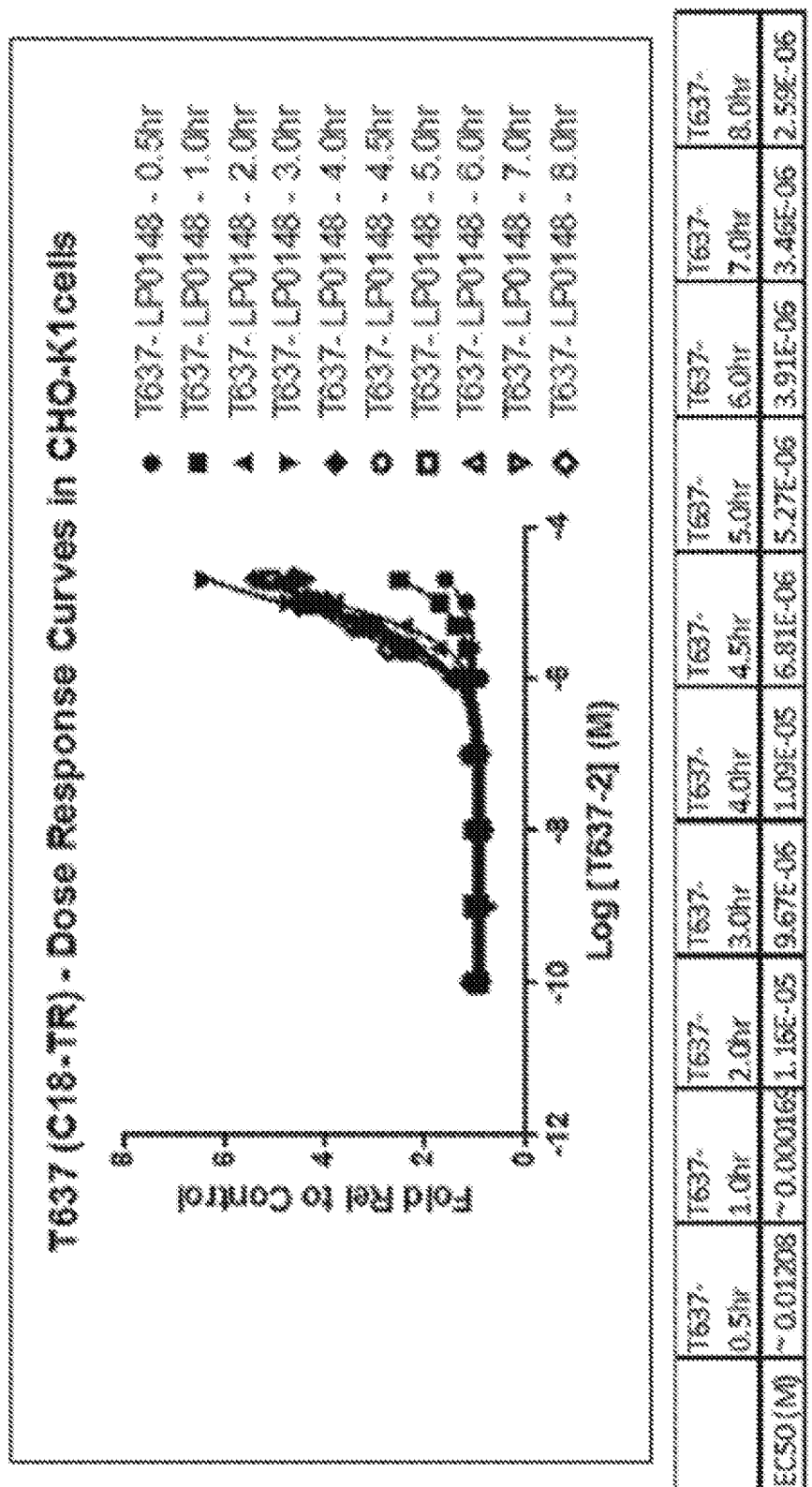

FIG. 26, top panel, is a graph of relative cAMP responses of CHO-K1 cells v. T637 ($C_{18}$-TR 40 mol %, squalane 40 mol %, chol-PEG2k 10 mol %, DOPC 10 mol %) treprostinil alkyl ester lipid nanoparticle composition challenge, at various dosages and time points. FIG. 26, bottom panel, shows the EC50 of T637 overtime, calculated from the cAMP responses of CHO-K1 cells v. T637-TR.

Figure 27:
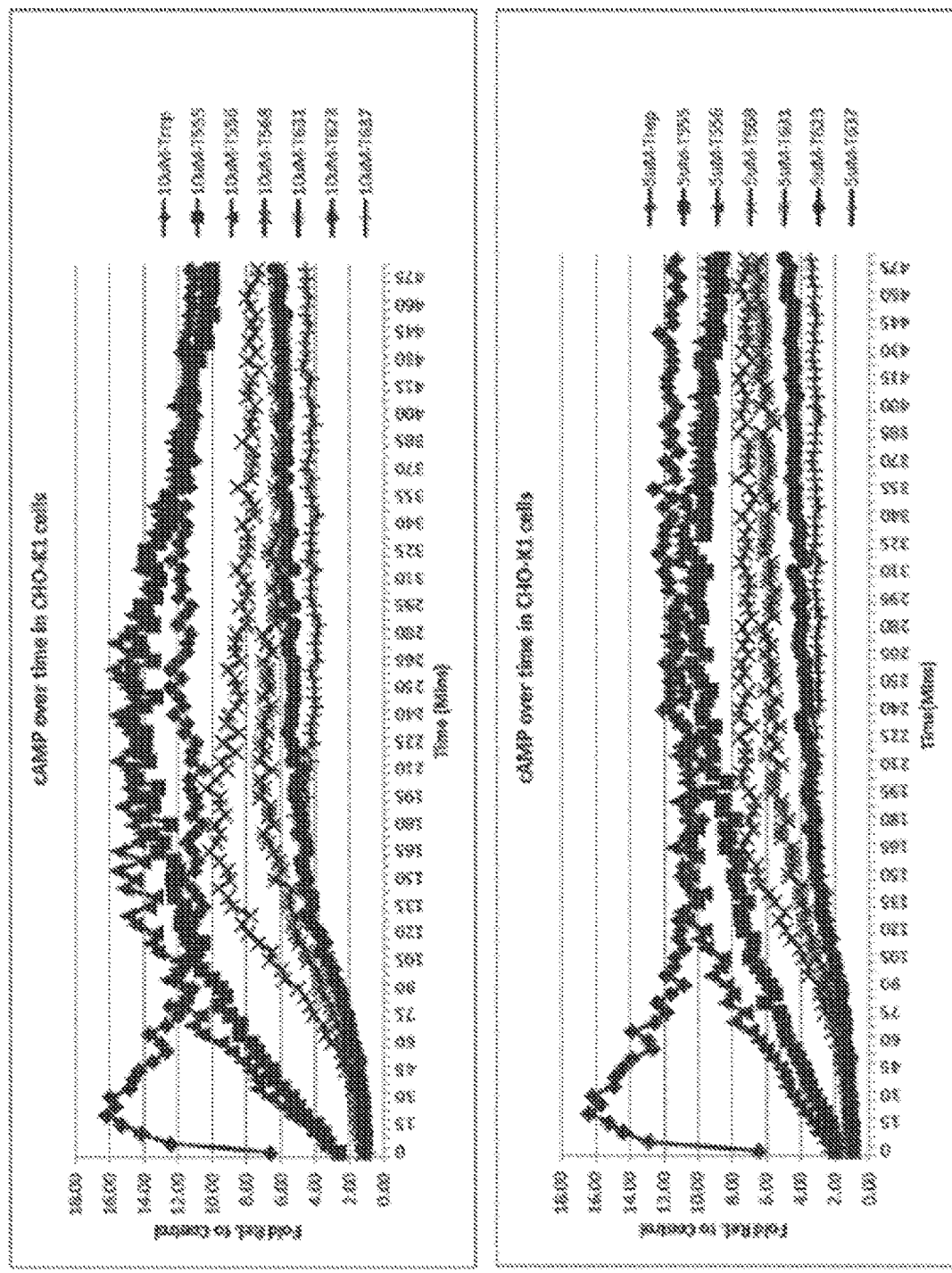

FIG. 27 are graphs of relative cAMP response of CHO-K1 cells vs. time, in response to challenge with treprostinil, T555 ($C_8$-TR 40 mol %, squalane 40 mol %, chol-PEG2k 10 mol %, DOPC 10 mol %), T556 ($C_{10}$-TR 40 mol %, squalane 40 mol %, chol-PEG2k 10 mol %, DOPC 10 mol %), T568 ($C_{12}$-TR 40 mol %, squalane 40 mol %, chol-PEG2k 10 mol %, DOPC 10 mol %), T631 ($C_{14}$-TR 40 mol %, squalane 40 mol %, chol-PEG2k 10 mol %, DOPC 10 mol %), T623 ($C_{16}$-TR 40 mol %, squalane 40 mol %, chol-PEG2k 10 mol %, DOPC 10 mol %), or T637 ($C_{18}$-TR 40 mol %, squalane 40 mol %, chol-PEG2k 10 mol %, DOPC 10 mol %) at 10 µM (top panel) or 5 µM (bottom panel).

Figure 28:
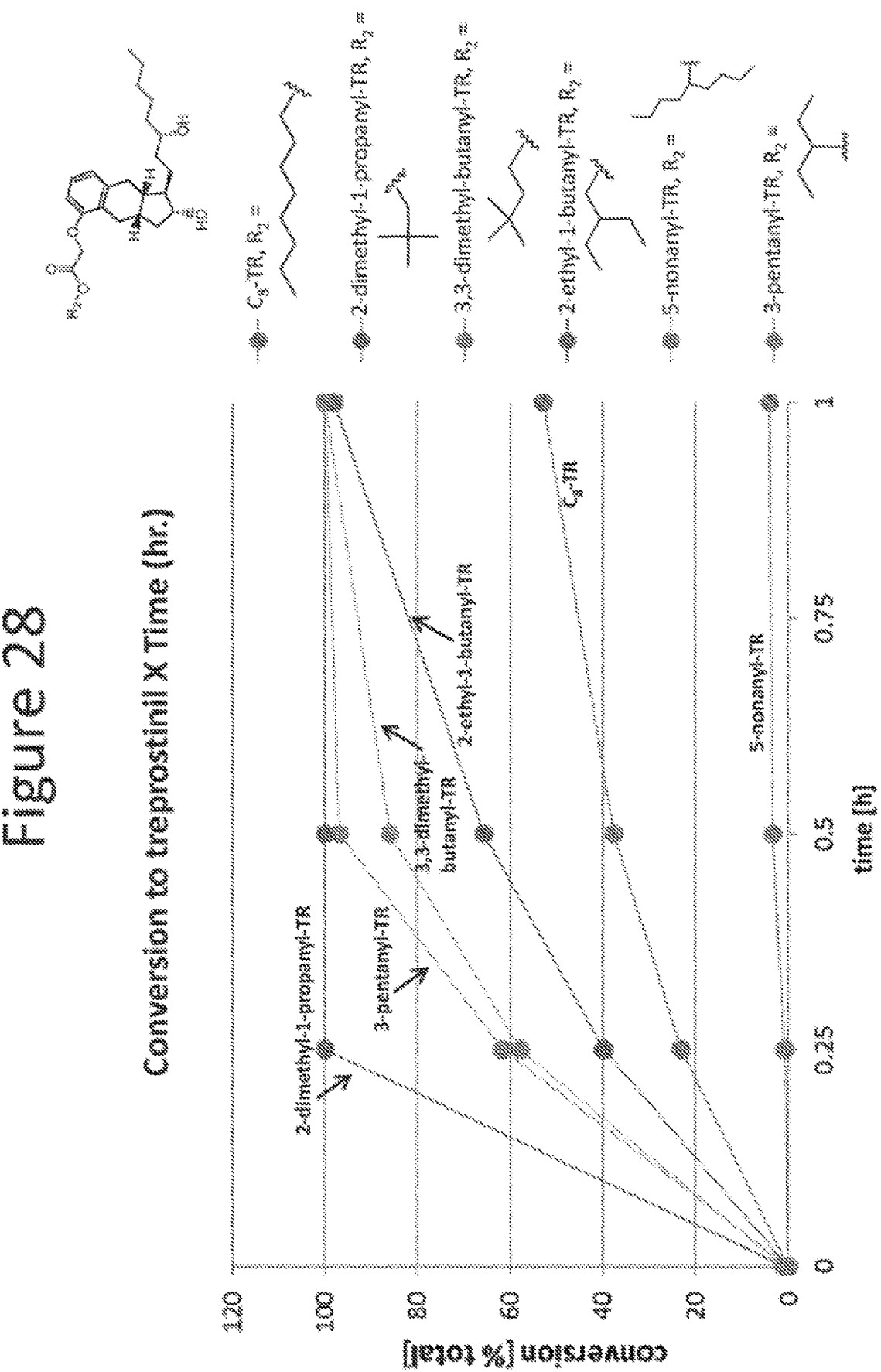

FIG. 28 is a graph of the conversion rate (% of total) over time (hours) for linear (C8TR) versus branched (2-dimethyl-1-propanyl-TR, 3,3-dimethyl-1-butanyl-TR, 2-ethyl-1-butanyl-TR, 5-nonanyl-TR, or 3-pentanyl-TR) prostacyclin compounds.

Figure 29:
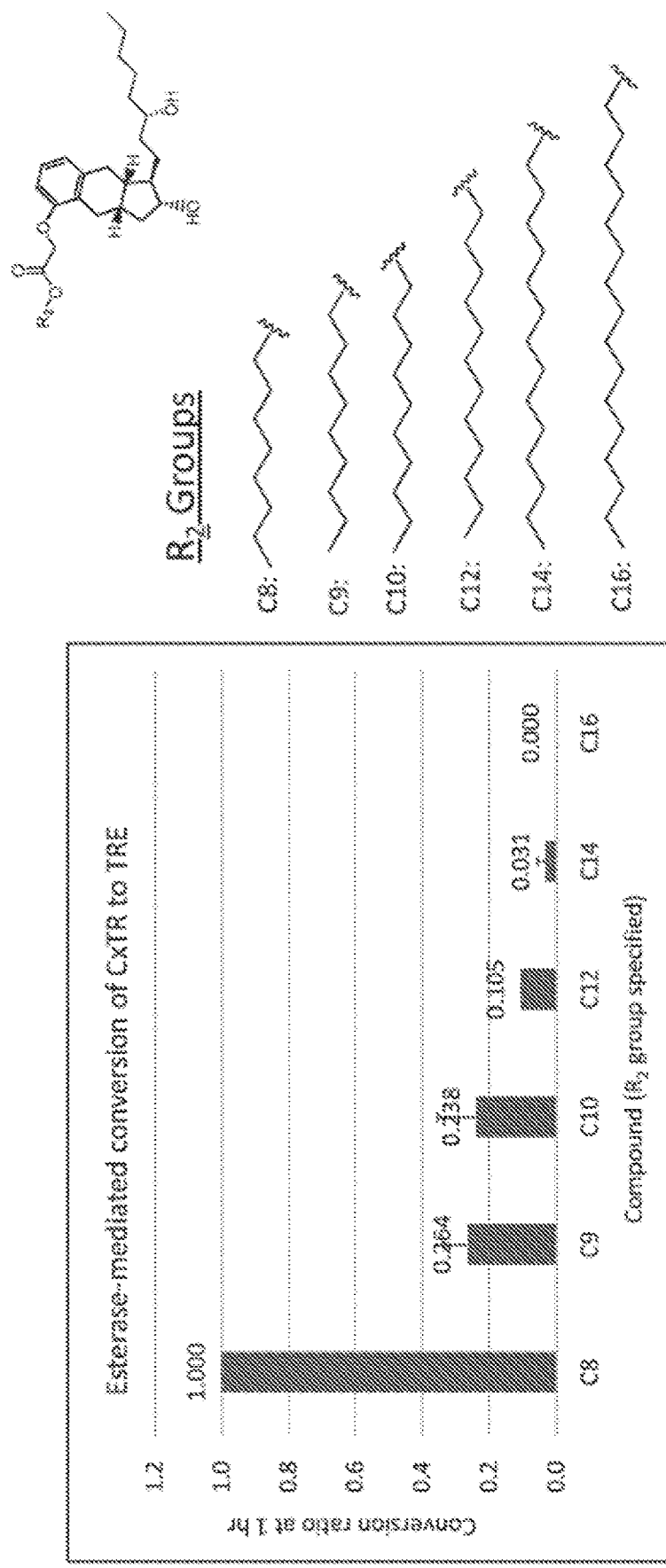

FIG. 29 is a graph showing the conversion of treprostinil compounds derivatized with various linear alkyl chains, relative to the conversion of the treprostinil compound derivatized with an octyl moiety ($R_2=C_8$). Conversion was measured at 1 hr after incubation with esterase.

Figure 30:
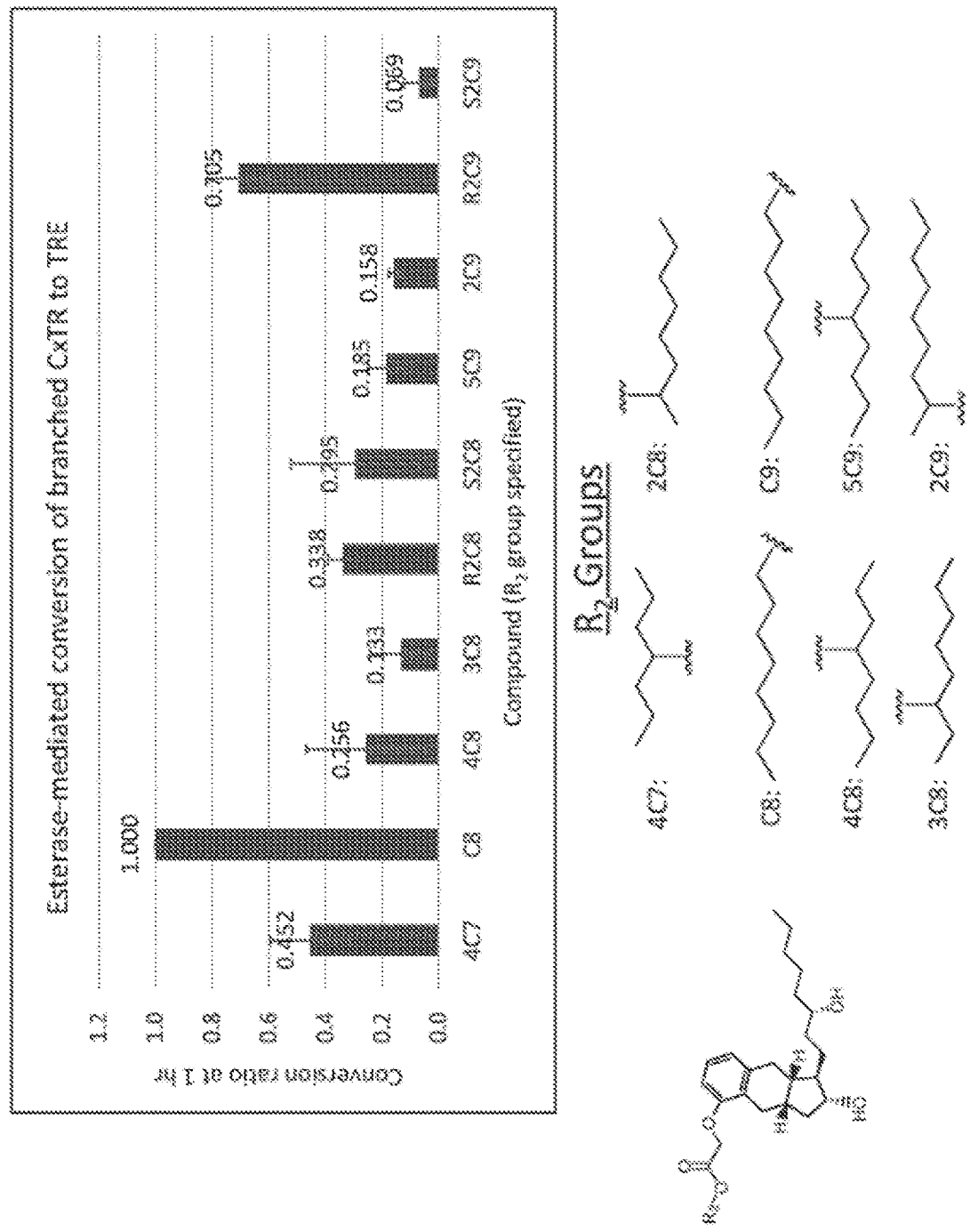

FIG. 30 is a graph showing the conversion of treprostinil compounds derivatized with various branched alkyl chains, relative to the conversion of the treprostinil compound derivatized with an octyl moiety ($R_2=C_8$). Conversion was measured at 1 hr after incubation with esterase.

Figure 31:
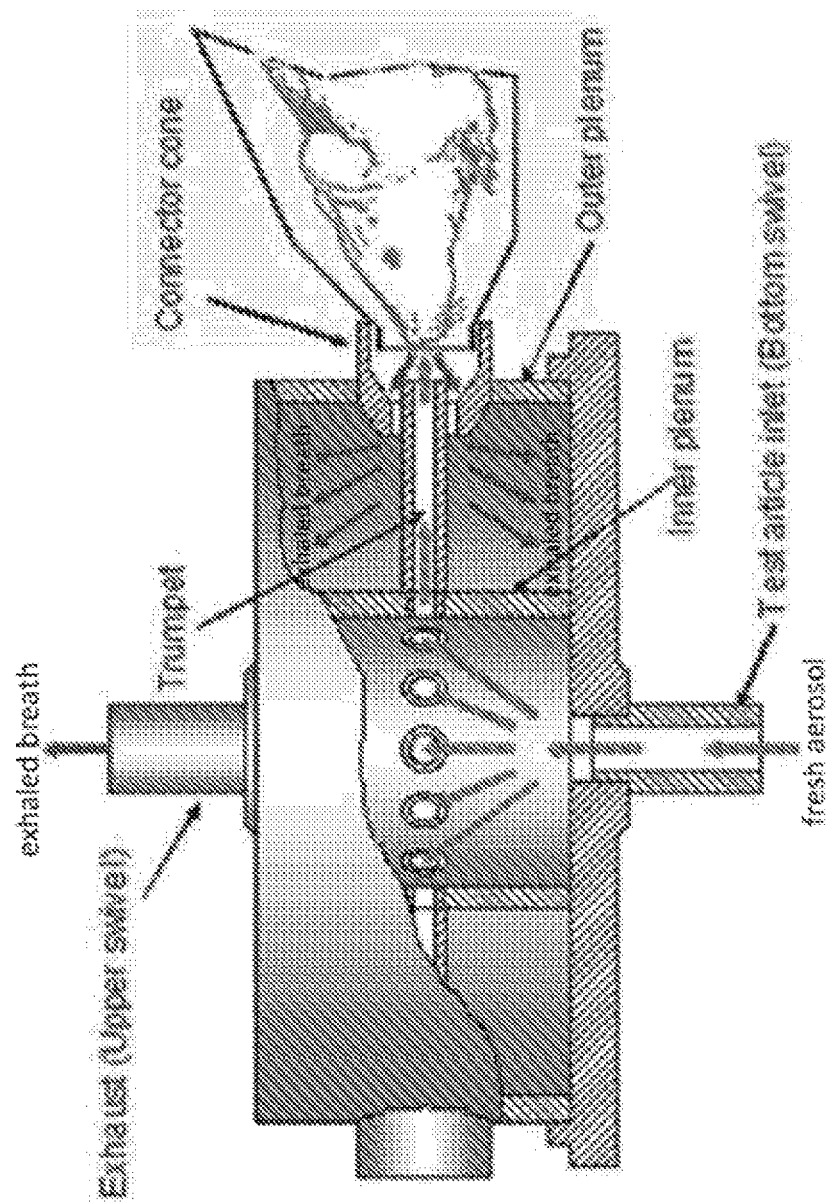

FIG. 31 is a schematic of the Jaeger-NYU nose only directed-flow inhalation exposure system (CH Technologies, Westwood, N.J., www.onares.org) used for a 24-hour pharmacokinetics study.

Figure 32:
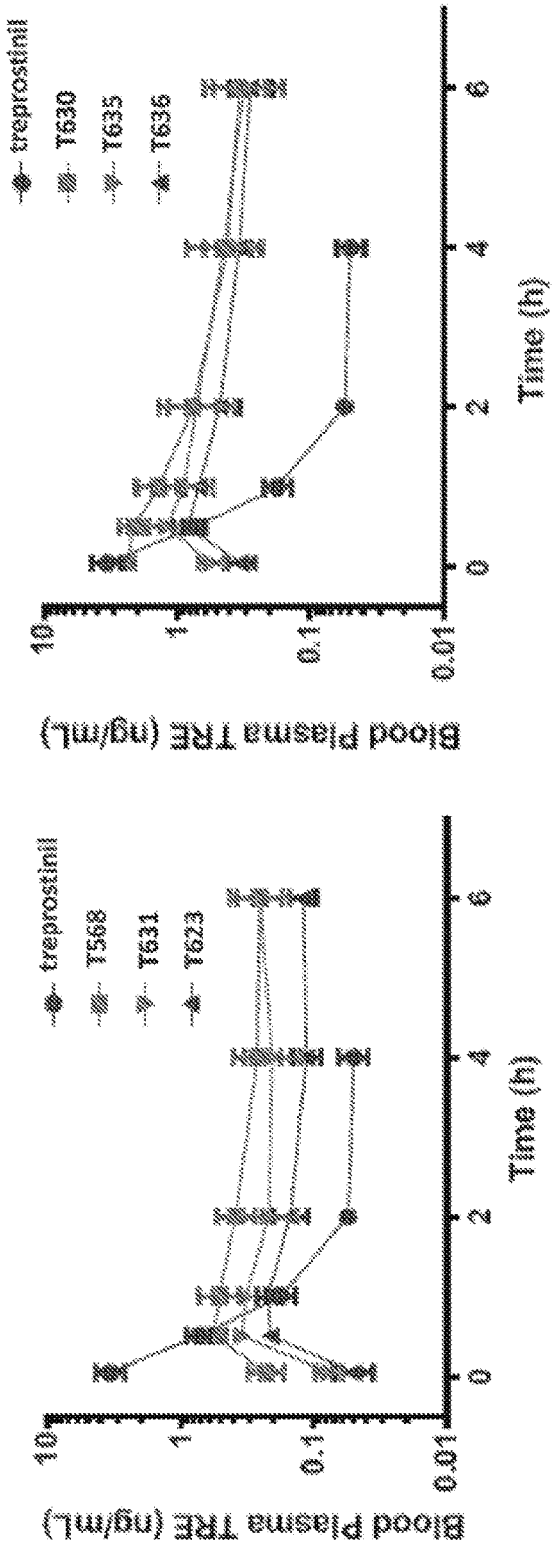

FIG. 32, left, is a graph of treprostinil blood plasma levels (ng/mL) as a function of time for treprostinil and various inhaled treprostinil alkyl ester formulations. FIG. 32, right, is a graph of treprostinil blood plasma levels (ng/mL) as a function of time for treprostinil and various inhaled treprostinil alkyl ester micelle formulations.

Figure 33:
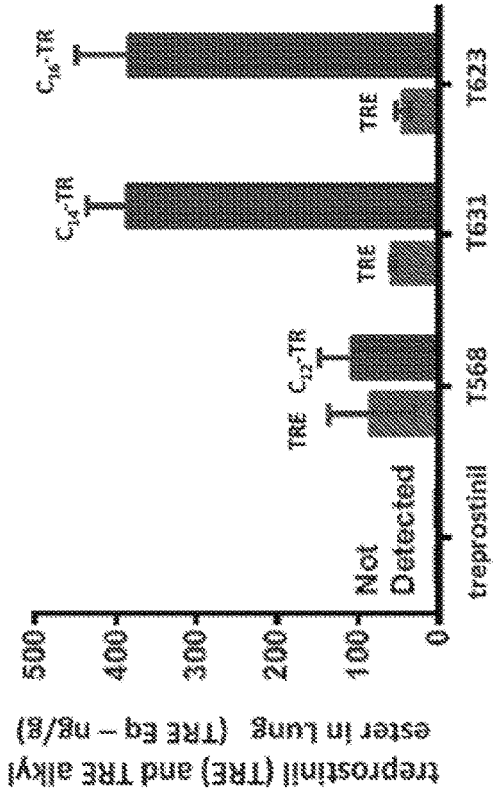

FIG. 33 is a graph of treprostinil and treprostinil alkyl ester concentration in the lung after dosing with nebulized treprostinil solution or formulated treprostinil alkyl ester suspensions. Lungs were collected at 6 hours after dosing. Treprostinil alkyl ester concentration is presented as treprostinil equivalent on a mole base.

Figure 34:
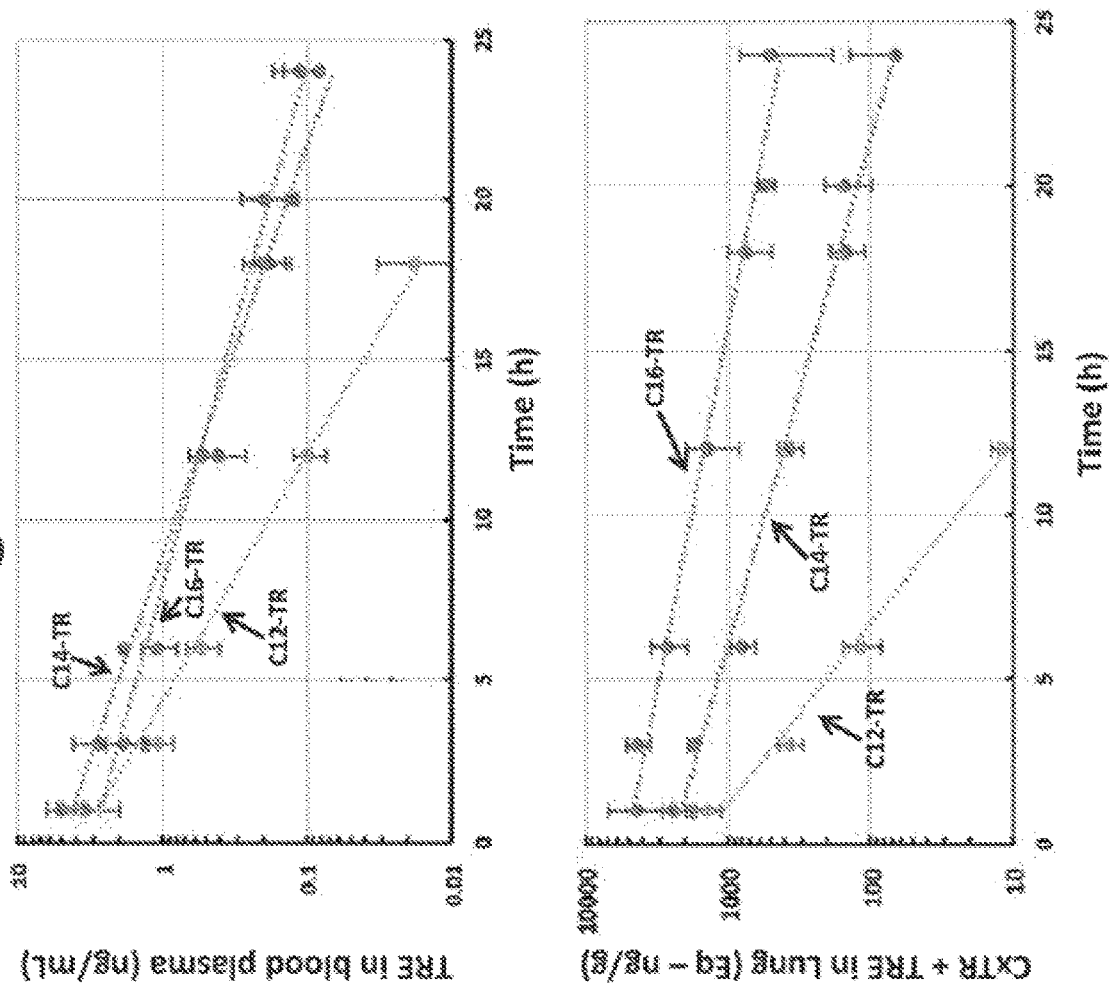

FIG. 34, top, is a graph of treprostinil blood plasma levels (ng/mL) as a function of time in rats after nose-only inhalation of nebulized treprostinil alkyl ester formulations. FIG. 34, bottom, is a graph of treprostinil and treprostinil alkyl ester blood plasma levels (ng/mL) as a function of time in rats after nose-only inhalation of nebulized treprostinil alkyl ester formulations.

Figure 35:
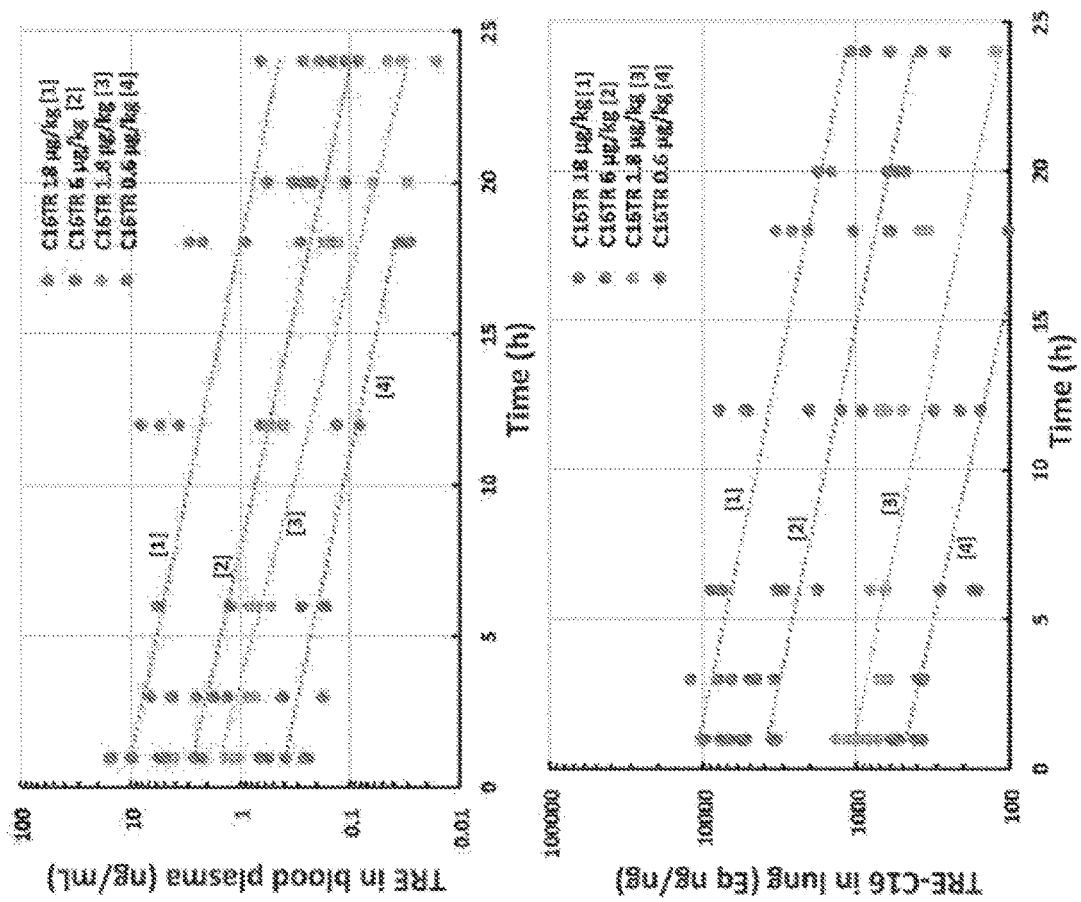

FIG. 35, top is a graph of treprostinil blood plasma levels (ng/mL) as a function of time after nebulization of various concentrations of $C_{16}$-TR formulations (nose only dosing). FIG. 35, bottom is a graph of treprostinil and $C_{16}$-TR blood plasma levels (ng/mL) as a function of time after nebulization of various concentrations of $C_{16}$-TR formulations (nose only dosing).

Figure 36:
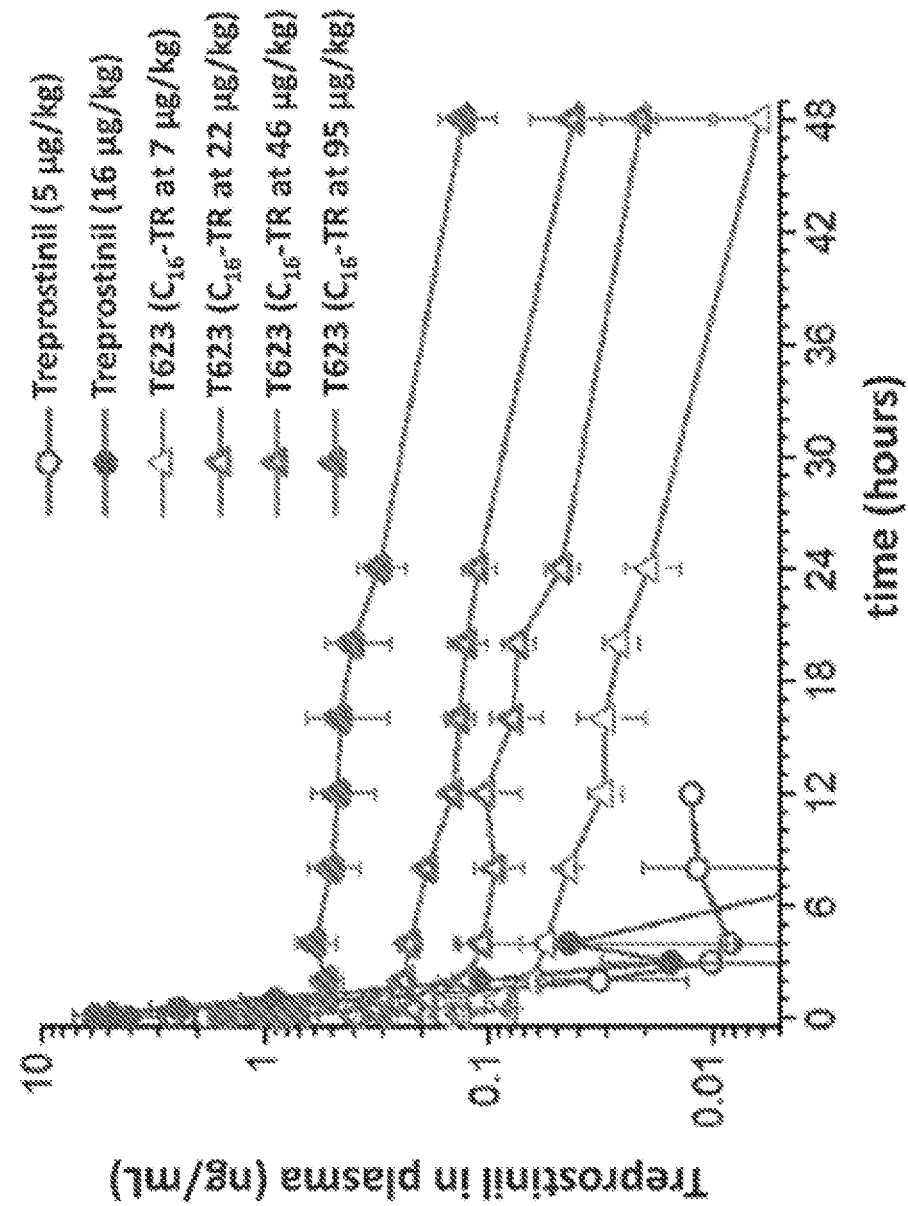

FIG. 36 is a graph of plasma concentrations of treprostinil (ng/mL) in intubated dogs as a function of time, after administration of treprostinil or the T623 lipid nanoparticle formulation ($C_{16}$-TR 40 mol %, squalane 40 mol %, chol-PEG2k 10 mol %, DOPC 10 mol %).

Figure 37:
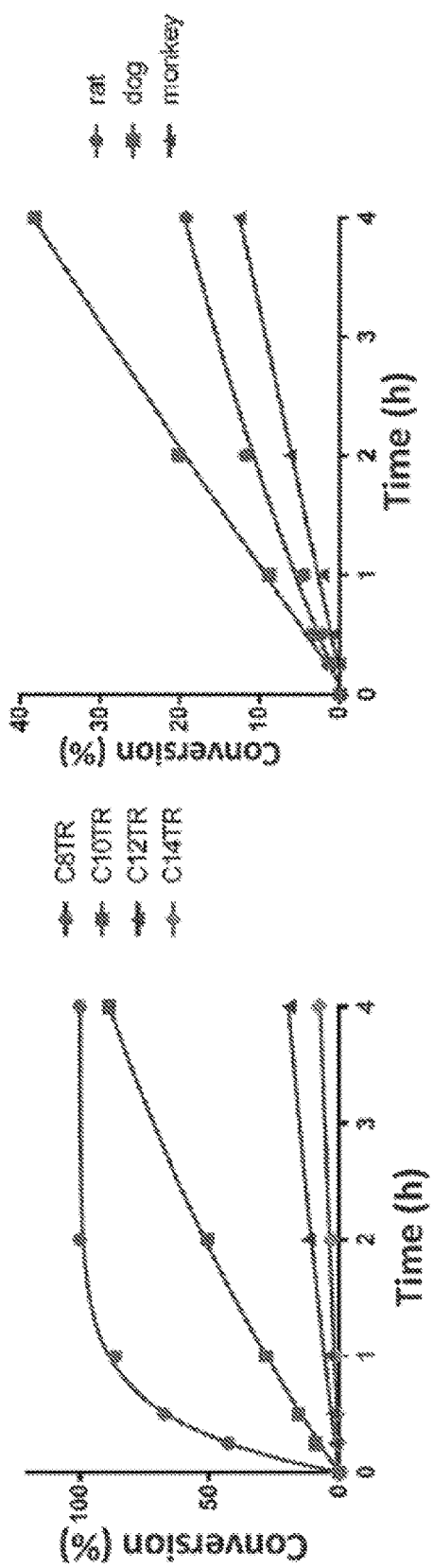

FIG. 37, left is a graph of treprostinil alkyl ester conversion to treprostinil as function of time for various treprostinil alkyl esters exposed to rat lung tissue homogenate. FIG. 37, right, is a graph of $C_{12}$-treprostinil conversion to treprostinil us function of time in rat, dog and monkey lung tissue homogenate.

Figure 38:
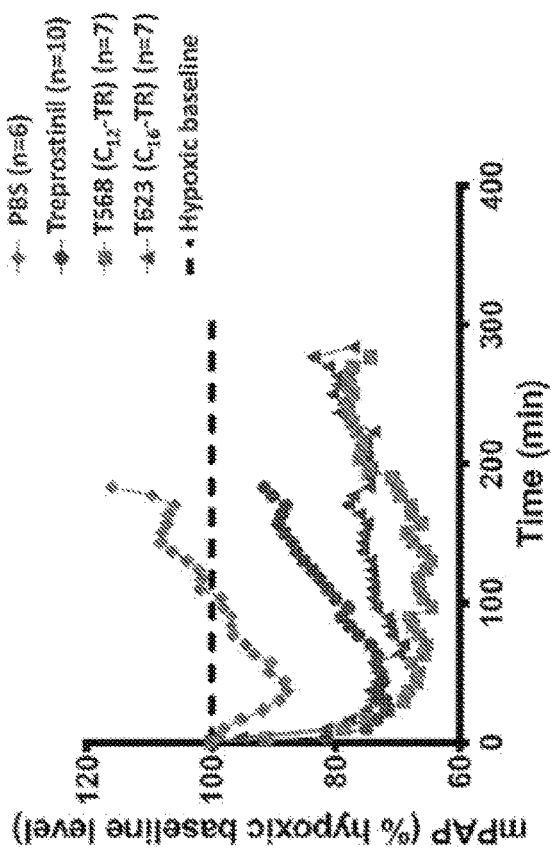

FIG. 38 is a graph of mean pulmonary arterial pressure (mPAP) as a function of time in rats treated with PBS, treprostinil, T568 ($C_{12}$-TR 40 mol %, squalane 40 mol %, chol-PEG2k 10 mol %, DOPC 10 mol %) of T623 ($C_{16}$-TR 40 mol %, squalane 40 mol %, chol-PEG2k 10 mol %, DOPC 10 mol %).

Figure 39:
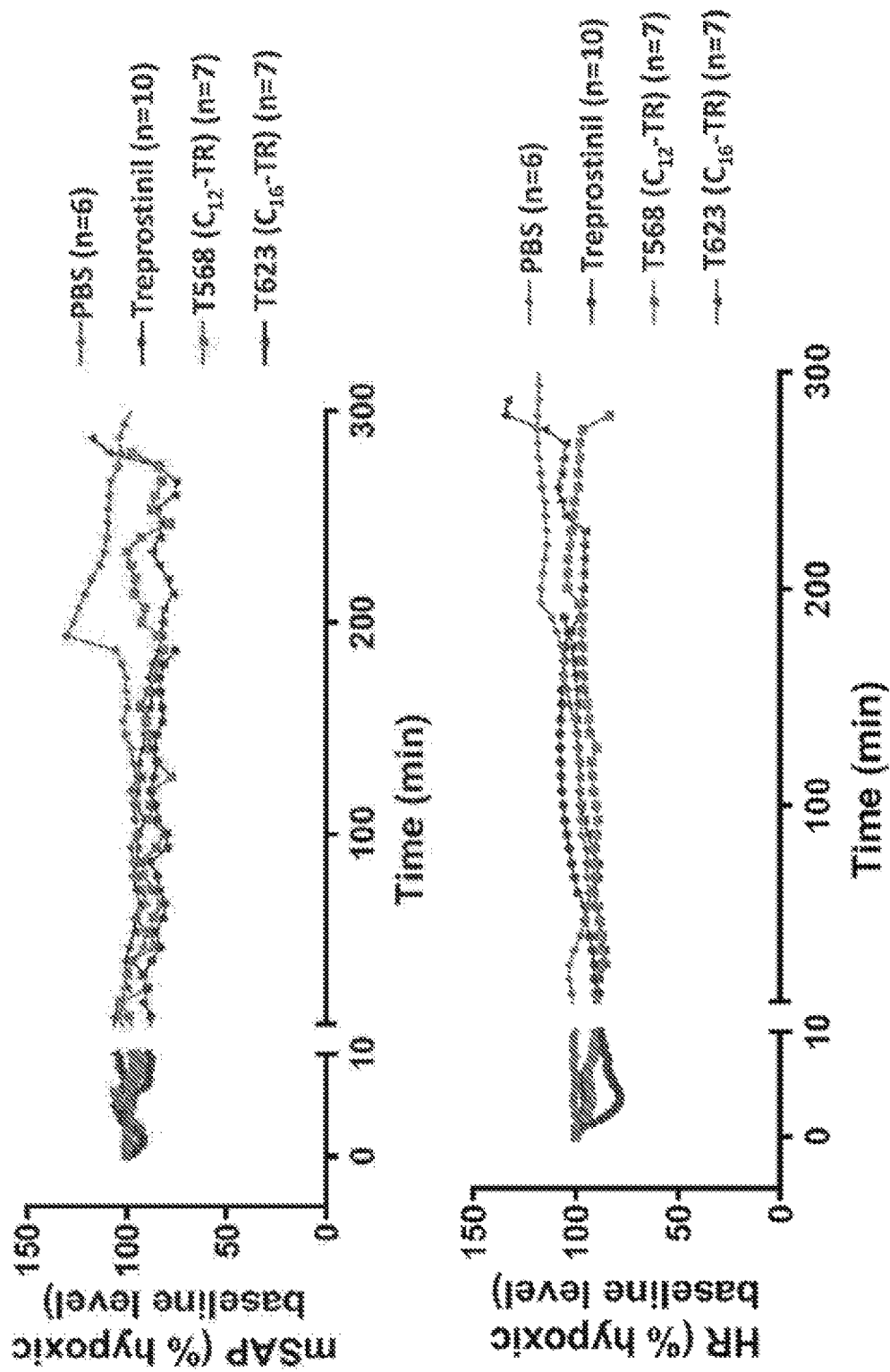

FIG. 39 top, is a graph of mean systemic arterial pressure (mSAP) as a function of time in rats treated with PBS, treprostinil, T568 or T623. FIG. 39, bottom, is a graph of heart rate as a function of time in rats treated with PBS, treprostinil, T568 or T623.

Figure 40:
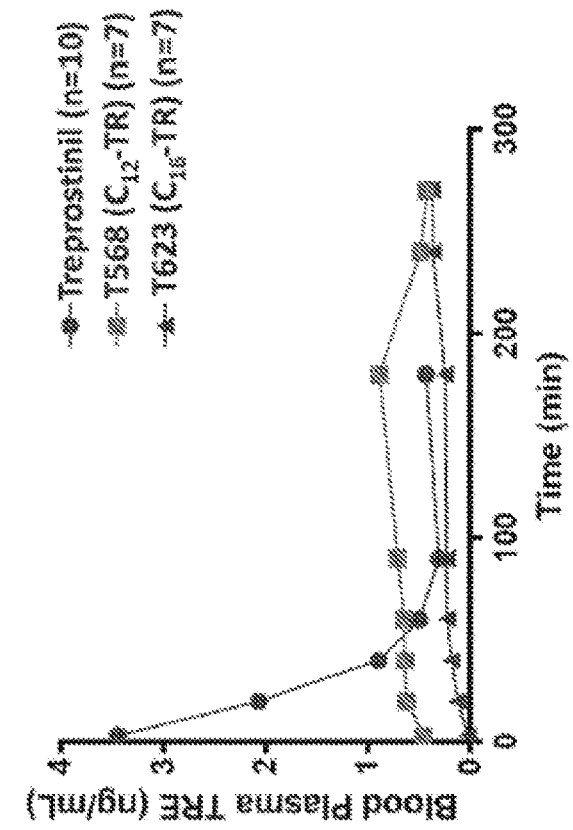

FIG. 40 is a graph of treprostinil blood plasma levels (ng/mL) as a function of time in rats after administration of free treprostinil, T568 or T623.

Figure 41:
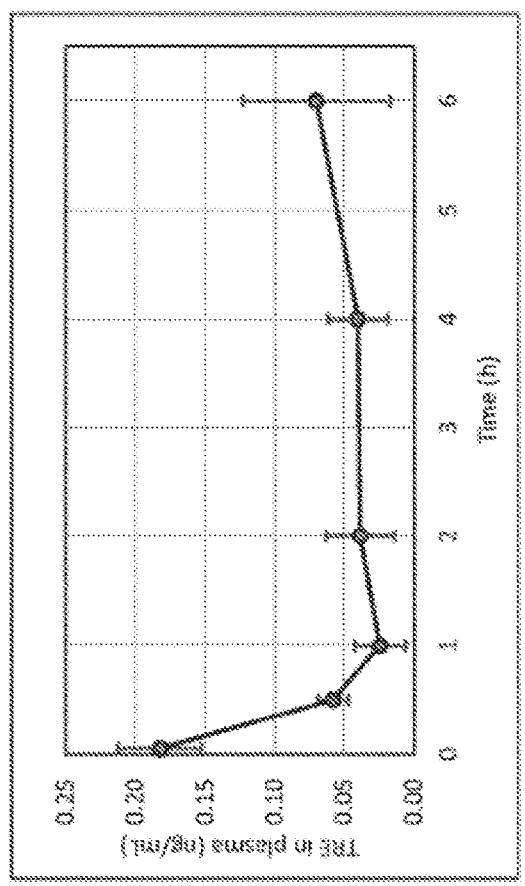

FIG. 41 is a graph of treprostinil blood plasma levels (ng/mL) as a function of time in rats after administration of composition T763 i

DETAILED DESCRIPTION OF THE INVENTION

The term "alkyl" as used herein refers to both a straight chain alkyl, wherein alkyl chain length is indicated by a range of numbers, and a branched alkyl, wherein a branching point in the chain exists, and the total number of carbons to the chain is indicated by a range of numbers. In exemplary embodiments, "alkyl" refers to an alkyl chain as defined above containing 6, 7, 8, 9, 10, 11, 12, 13, 14, 15, 16 carbons (i.e., $C_6$-$C_{16}$ alkyl).

The term "alkenyl" as used herein refers to a carbon chain containing one or more carbon-carbon double bonds.

The term "aryl" as used herein refers to a cyclic hydrocarbon, where the ring is characterized by delocalized π electrons (aromaticity) shared among the ring members, and wherein the number of ring atoms is indicated by a range of numbers. In exemplary embodiments, "aryl" refers to a cyclic hydrocarbon as described above containing 6, 7, 8, 9, or 10 ring atoms (i.e., $C_6$-$C_{10}$ aryl). Examples of an aryl group include, but are not limited to, benzene, naphthalene, tetralin, indene, and indane.

The term "alkoxy" as used herein refers to —O-(alkyl), wherein "alkyl" is as defined above.

The term "substituted" in connection with a moiety as used herein refers to a further substituent which is attached to the moiety at any acceptable location on the moiety. Unless otherwise indicated, moieties can bond through a carbon, nitrogen, oxygen, sulfur, or any other acceptable atom.

The term "amino acid" refers to both natural (genetically encoded) and non-natural (non-genetically encoded) amino acids, and moieties thereof. Of the twenty natural amino acids, 19 have the general structure:

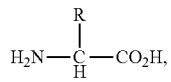

where R is the amino acid sidechain. The 20$^{th}$ amino acid, proline, is also within the scope of the present invention, and has the following structure:

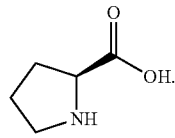

Of the twenty natural amino acids, all but glycine is chiral, and both the D- and L-amino amino acid isomers, as well as mixtures thereof, are amenable for use with the prostacyclin compounds described herein. It is also noted that an amino acid moiety is encompassed by the term "amino acid." For example, the amino acid moieties

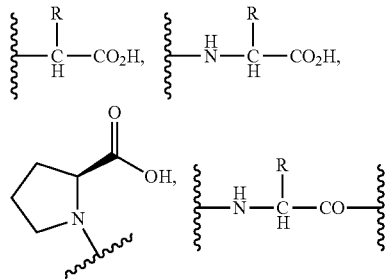

are encompassed by the term "amino acid."

Examples of non-natural amino acids amenable for use with the present invention include β-alanine (β-Ala); 2,3-diaminopropionic acid (Dpr); nipecotic acid (Nip); pipecolic acid (Pip); ornithine (Om); citrulline (Cit); t-butylalanine (t-buA); 2-tbutylglycine (t-BuG); N-methylisoleucine (MeIle); phenylglycine (PhG); cyclohexylalanine (ChA); norleucine (Nle); naphthylalanine (Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyllysine (AcLys); 2,4-diaminobutyric acid (Dbu); 2,3-diaminobutyric acid (Dab); p-aminophenylalanine (Phe (pNH$_2$)), N-methyl valine (MeVal); homocysteine (hCys), homophenylalanine (hPhe); homoserine (hSer); hydroxyproline (Hyp); homoproline (hPro), and the corresponding D-enantiomer of each of the foregoing. Other non-genetically encoded amino acid residues include 3-aminopropionic acid; 4-aminobutyric acid; isonipecotic acid (Inp); aza-pipecolic acid (azPip); aza-proline (azPro); α-aminoisobutyric acid (Aib); ε-aminohexanoic acid (Aha); δ-aminovaleric acid (Ava); N-methylglycine (MeGly).

A "peptide" is a polymer of amino acids (or moieties thereof) linked by a peptide bond. Peptides for use with the present invention, comprise from about two to about fifteen amino acids, for example, two, three, four, five, six, seven, eight, nine or ten amino acids (or moieties thereof).

The term "salt" or "salts" as used herein encompasses pharmaceutically acceptable salts commonly used to form alkali metal salts of free acids and to form addition salts of free bases. The nature of the salt is not critical, provided that it is pharmaceutically acceptable. Suitable pharmaceutically acceptable acid addition salts may be prepared from an inorganic acid or from an organic acid. Exemplary pharmaceutical salts are disclosed in Stahl, P. H., Wermuth, C. G., Eds. *Handbook of Pharmaceutical Salts: Properties, Selection and Use*; Verlag Helvetica Chimica Acta/Wiley-VCH: Zurich, 2002, the contents of which are hereby incorporated by reference in their entirely. Specific non-limiting examples of inorganic acids are hydrochloric, hydrobromic, hydroiodic, nitric, carbonic, sulfuric and phosphoric acid. Appropriate organic acids include, without limitation, aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric or galacturonic acid. Suitable pharmaceutically acceptable salts of free acid-containing compounds disclosed herein include, without limitation, metallic salts and organic salts. Exemplary metallic salts include, but are not limited to, appropriate alkali metal (group Ia) salts, alkaline earth metal (group IIa) salts, and other physiological acceptable metals. Such salts can be made from aluminum, calcium, lithium, magnesium, potassium, sodium and zinc. Exemplary organic salts can be made from primary amines, secondary amines, tertiary amines and quaternary ammonium salts, for example, tromethamine, diethylamine, tetra-N-methylammonium, N,N'-dibenzylethylenediamine, chloroprocaine, choline, diethanolamine, ethylenediamine, meglumine (N-methylglucamine) and procaine.

In one aspect, the present invention provides a prostacyclin compound, for example, a treprostinil derivative, or a composition comprising the same, that is effective when employed in a once-daily, twice-daily or three-times daily dosing regimen, for example, for the treatment of pulmonary arterial hypertension or portopulmonary hypertension in a patient in need thereof. The prostacyclin compound provided herein, in one embodiment, can be administered less frequently than treprostinil, with equal or greater efficacy. Moreover, in one embodiment, the side effect profile of the compounds provided herein is less deleterious than the side effect profile resulting from treprostinil administrator. These advantages, in one embodiment, allow for greater patient compliance. Treatment, in one embodiment, occurs through pulmonary administration of one of the compounds provided herein, for example via a nebulizer, dry powder inhaler, or a metered dose inhaler. In some embodiments, a composition comprising one of the compounds provided herein is administered via a nebulizer to a patient in need of PH treatment. In some embodiments a compound described herein is suspended in a propellant and delivered to a patient via a metered dose inhaler.

In one aspect of the invention described herein, a prostacyclin compound of Formula (I), or a pharmaceutically acceptable salt thereof, is provided:

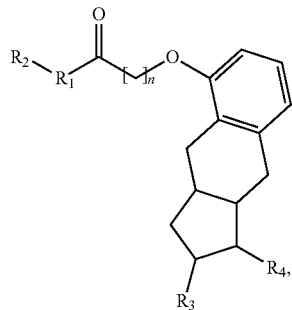

Formula (I)

wherein $R_1$ is NH, O or S;

$R_2$ is H, a linear $C_5$-$C_{18}$ alkyl, branched $C_5$-$C_{18}$ alkyl, linear $C_2$-$C_{18}$ alkenyl, branched $C_3$-$C_{18}$ alkenyl, aryl, aryl-$C_1$-$C_{18}$ alkyl; an amino acid or a peptide;

$R_3$ is H, OH, optionally substituted linear or branched $C_1$-$C_{15}$ alkyoxy, O-optionally substituted linear or branched $C_2$-$C_{15}$ alkenyl, O—(C═O)-optionally substituted linear or branched $C_1$-$C_{15}$ alkyl, or O—(C═O)-optionally substituted linear or branched $C_2$-$C_{15}$ alkenyl;

$R_4$ is an optionally substituted linear or branched $C_1$-$C_{15}$ alkyl, or an optionally substituted linear or branched $C_2$-$C_{15}$ alkenyl; and n is an integer from 0 to 5, with the proviso that the prostacyclin compound of Formula (I) is not treprostinil.

In a further embodiment, a prostacyclin compound of Formula (I) is provided, wherein $R_3$ is OH and n is 0 or 1. In even a further embodiment, $R_4$ is an optionally substituted linear or $C_1$-$C_{15}$ alkyl. In even a further embodiment, $R_1$ is NH or O.

In one embodiment, a prostacyclin compound of Formula (I) is provided, wherein $R_1$ is NH, O or S; R; is a linear $C_5$-$C_{18}$ alkyl, branched $C_5$-$C_{18}$ alkyl, linear $C_2$-$C_{18}$ alkenyl, branched $C_3$-$C_{18}$ alkenyl; $R_3$ is H, OH or O-alkyl; $R_4$ is an optionally substituted linear or branched $C_1$-$C_{15}$ alkyl, or an optionally substituted linear or branched $C_2$-$C_{15}$ alkenyl; and n is an integer from 0 to 5. In even a further embodiment, $R_1$ is NH or O and $R_2$ is a linear $C_5$-$C_{18}$ alkyl or a branched $C_5$-$C_{18}$ alkyl.

In one embodiment, $R_2$ is aryl or aryl-$C_1$-$C_{18}$ alkyl; $R_3$ is OH and n is 0 or 1. In even a further embodiment, $R_1$ is an optionally substituted linear or branched $C_1$-$C_{15}$ alkyl.

In one embodiment, the present invention provides a prostacyclin compound of Formula (I), wherein the compound is a compound of one of Formulae (Ia), (Ib), (Ic) or (Id), or a pharmaceutically acceptable salt thereof:

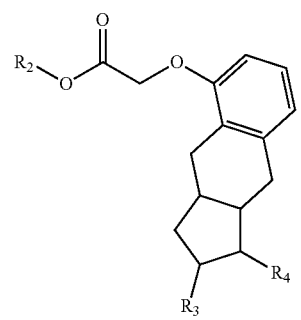

Formula (Ia)

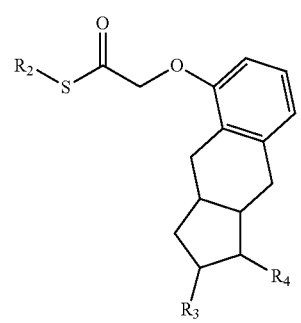

Formula (Ib)

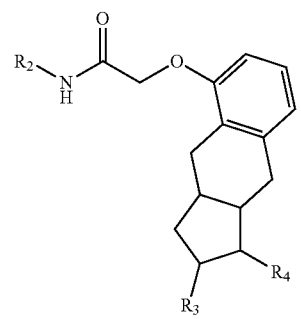

Formula (Ic)

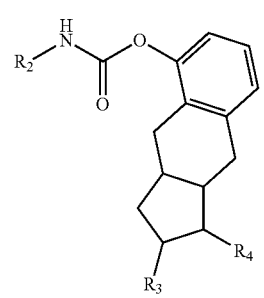

Formula (Id)

wherein, $R_2$ is H, a linear or branched $C_5$-$C_{18}$ alkyl, linear $C_2$-$C_{18}$ alkenyl, or a branched $C_3$-$C_{18}$ alkenyl;

$R_1$ is H, OH, optionally substituted linear or branched $C_1$-$C_{15}$ alkyoxy, O-optionally substituted linear or branched $C_2$-$C_{15}$ alkenyl, —O(C═O)-optionally substituted linear or branched $C_1$-$C_{15}$ alkyl, or —O(C═O)-optionally substituted linear or branched $C_2$-$C_{15}$ alkenyl; and $R_4$ is

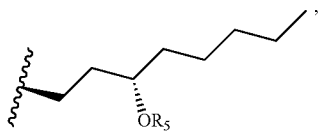

an optionally substituted linear or branched $C_1$-$C_{15}$ alkyl, or an optionally substituted linear or branched $C_2$-$C_{15}$ alkenyl, where $R_5$ is H, optionally substituted linear or branched $C_1$-$C_{15}$ alkyl, optionally substituted linear or branched $C_2$-$C_{15}$ alkenyl, (C=O)-optionally substituted linear or branched $C_1$-$C_{15}$ alkyl, or (C=O)-optionally substituted linear or branched $C_2$-$C_{15}$ alkenyl. In a further embodiment, $R_4$ is

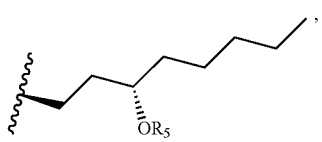

with the proviso that the compound is not treprostinil, i.e., $R_2$ and $R_5$ cannot both be H.

In one embodiment of Formula (Ia), Formula (Ib), formula (Ic) and Formula (Id), $R_2$ is a linear or branched $C_5$-$C_{18}$ alkyl. In even a further embodiment, $R_2$ is

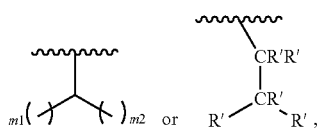

where m1 and m2 are each independently an integer selected from 1 to 9 and each occurrence of R' is independently H, a linear or branched $C_1$-$C_8$ alkyl, or a linear or branched $C_1$-$C_8$ alkenyl. In even a further embodiment, $R_2$ is

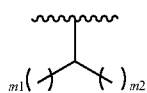

and m1 and m2 are both 4. In another embodiment, $R_2$ is

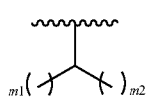

and m1 is 3 and m2 is 4, or m1 is 2 and m2 is 3.

When m1 and/or m2 is an integer from 2-9, the m1/m2 at the end of the carbon chain is $CH_3$, while the remaining m1/m2 groups are $CH_2$.

In one embodiment of Formula (Ia), Formula (Ib), Formula (Ic) and Formula (Id), $R_2$ is

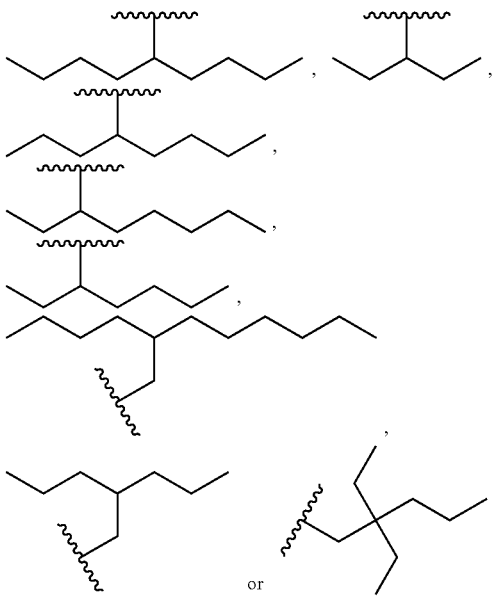

In a further embodiment, $R_3$ is OH and $R_4$ is

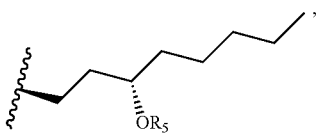

where $R_5$ is H, optionally substituted linear or branched $C_1$-$C_{15}$ alkyl, optionally substituted linear or branched $C_2$-$C_{15}$ alkenyl, (C=O)-optionally substituted linear or branched $C_1$-$C_{15}$ alkyl, or (C=O)-optionally substituted linear or branched $C_2$-$C_{15}$ alkenyl.

In one embodiment of Formulae (Ia), (Ib), (Ic) or (Id), $R_2$ is H, $R_3$ is OH and $R_4$ is

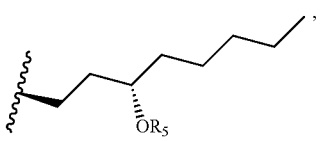

and $R_5$ is

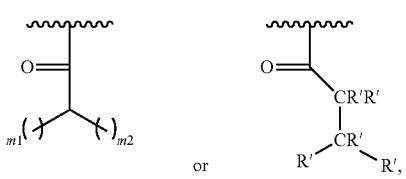

where m1 and m2 are each independently an integer selected from 1 to 9 and each occurrence of R' is independently H, a linear or branched $C_1$-$C_8$ alkyl, or a linear or branched $C_1$-$C_8$ alkenyl. When m1 and/or m2 is an integer from 2-9, the m1/m2 at the end of the carbon chain is $CH_3$, while the remaining m1/m2 groups are $CH_2$.

In another embodiment, a prostacyclin compound of one of formula (Ia), (Ib), (Ic) or (Id) is provided wherein $R_3$ is OH, as provided in one of Formulae (Ia'), (Ib'), (Ic') or (Id').

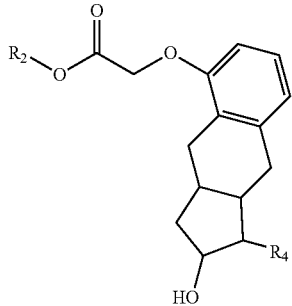

Formula (Ia')

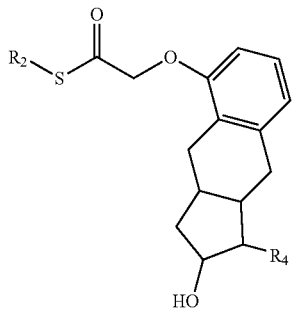

Formula (Ib')

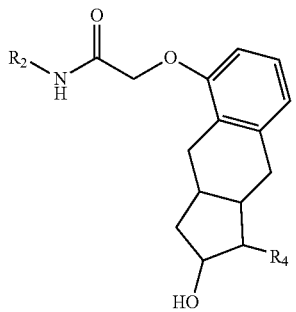

Formula (Ic')

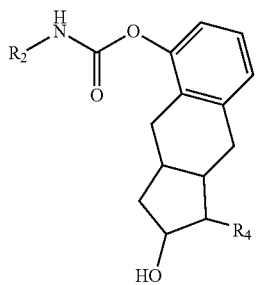

Formula (Id')

wherein, $R_2$ is H, a linear or branched $C_5$-$C_{18}$ alkyl, or a linear or branched $C_5$-$C_{18}$ alkenyl; and $R_4$ is

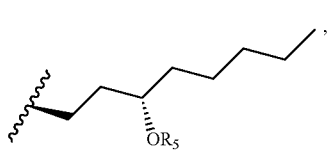

an optionally substituted linear or branched $C_1$-$C_{15}$ alkyl, or an optionally substituted linear or branched $C_2$-$C_{15}$ alkenyl, wherein $R_5$ is H, optionally substituted linear or branched $C_1$-$C_{15}$ alkyl, optionally substituted linear or branched $C_2$-$C_{15}$ alkenyl, (C=O)-optionally substituted linear or branched $C_1$-$C_{15}$ alkyl, or (C=O)-optionally substituted linear or branched $C_2$-$C_{15}$ alkenyl, with the proviso that $R_2$ and $R_5$ are not both H. In one embodiment of Formula (Ia'), Formula (Ib'), Formula (Ic') and Formula (Id'), $R_4$ is

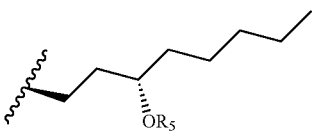

and $R_2$ is

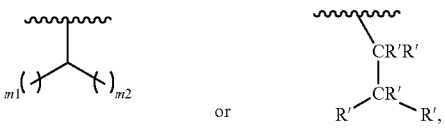

or $R^5$ is

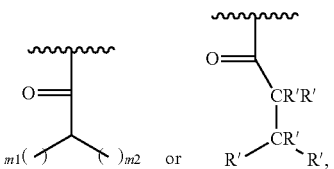

where m1 and m2 are each independently an integer selected from 1 to 9 and each occurrence of R' is independently H, a linear or branched $C_1$-$C_8$ alkyl, or a linear or branched $C_1$-$C_8$. In even a further embodiment, $R_2$ is

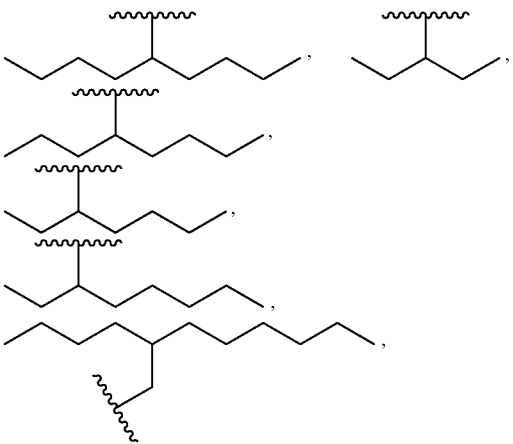

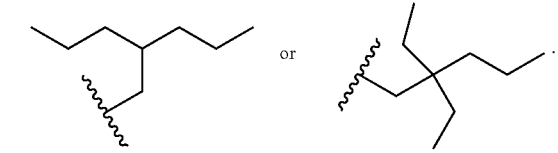

Yet another embodiment of the invention relates to a prostacyclin compound of one of Formula (Ia"), (Ib"), (Ic") or (Id"), or a pharmaceutically acceptable salt thereof:

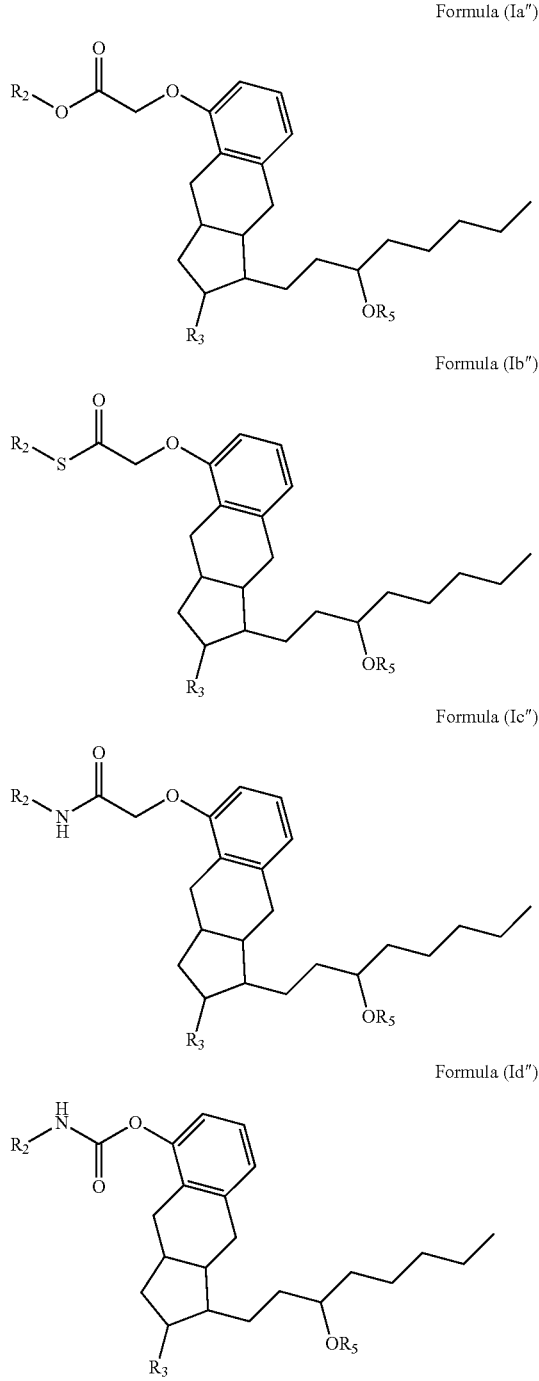

Formula (Ia")

Formula (Ib")

Formula (Ic")

Formula (Id")

wherein, $R_2$ is H, a linear or branched $C_5$-$C_{18}$ alkyl, linear $C_2$-$C_{18}$ alkenyl, branched $C_3$-$C_{18}$ alkenyl, aryl, aryl-$C_1$-$C_{18}$ alkyl, an amino acid or a peptide; and $R_3$ is H, OH, optionally substituted linear or branched $C_1$-$C_{15}$ alkyoxy, O-optionally substituted linear or branched $C_2$-$C_{15}$ alkenyl, O—(C═O)-optionally substituted linear or branched $C_1$-$C_5$ alkyl, or O—(C═O)-optionally substituted linear or branched $C_2$-$C_{15}$ alkenyl; and $R_5$ is H, optionally substituted linear or branched $C_1$-$C_{15}$ alkyl, optionally substituted linear or branched $C_2$-$C_{15}$ alkenyl, (C═O)-optionally substituted linear or branched $C_1$-$C_{15}$ alkyl, or (C═O)-optionally substituted linear or branched $C_2$-$C_{15}$ alkenyl, with the proviso that $R_2$ and $R_5$ are not both H. In a further embodiment, $R_3$ is OH and $R_2$ is 5-nonanyl, 4-heptyl, 4-octyl, 3-octyl, 2-dimethyl-1-propyl, 3,3-dimethyl-1-butyl, 2-ethyl-1-butyl, 3-pentyl, pentyl, hexyl, heptyl, octyl, nonyl, decyl, undecyl, dodecyl, tridecyl, tetradecyl, pentadecyl, hexadecyl, heptadecyl or octadecyl. In even a further embodiment, $R_2$ is decyl, undecyl, dodecyl, tridecyl, tetradecyl, pentadecyl, hexadecyl, heptadecyl or octadecyl. In even a further embodiment, $R_2$ is a linear alkyl.

One embodiment of the present invention is directed to compounds of Formula (Ic), (Ic') and (Ic"). In a further embodiment, $R_2$ is a linear $C_5$-$C_{18}$ alkyl or a branched $C_5$-$C_{18}$ alkyl. In even a further embodiment, $R_2$ is a linear $C_6$-$C_{18}$ alkyl or a branched $C_6$-$C_{18}$ alkyl. In yet a further embodiment, $R_2$ is a linear $C_6$-$C_{14}$ alkyl, e.g., a linear $C_6$ alkyl, $C_8$ alkyl, $C_{10}$ alkyl, $C_{12}$ alkyl or $C_{14}$ alkyl.

In one embodiment, a compound of Formula (Ic") is provided wherein $R_2$ is a linear $C_5$-$C_{18}$ alkyl; $R_3$ is OH and $R_5$ is H. In another embodiment, a compound of Formula (Ic") is provided wherein $R_2$ is a linear $C_6$-$C_{18}$ alkyl; $R_3$ is OH and $R_5$ is H. In yet embodiment, a compound of Formula (Ic") is provided wherein $R_2$ is a linear $C_6$-$C_{16}$ alkyl; $R_3$ is OH and $R_5$ is H. In even another embodiment, a compound of Formula (Ic") is provided wherein $R_2$ is a linear $C_8$-$C_{14}$ alkyl; $R_3$ is OH and $R_5$ is OH.

In one embodiment, a compound of Formula (Ic") is provided wherein $R_2$ is a linear $C_5$-$C_{18}$ alkyl, $R_3$ is OH and $R_5$ is H. In another embodiment, a compound of Formula (Ic") is provided wherein $R_2$ is a branched $C_6$-$C_{18}$ alkyl; $R_3$ is OH and $R_5$ is H. In yet embodiment, a compound of Formula (Ic") is provided wherein $R_2$ is a branched $C_6$-$C_{16}$ alkyl; $R_3$ is OH and $R_5$ is H. In even another embodiment, a compound of Formula (Ic") is provided wherein $R_2$ is a branched $C_8$-$C_{14}$ alkyl; $R_3$ is OH and $R_5$ is H.

In even a further embodiment, a compound of Formula (Ic), (Ic') and (Ic") is administered to a patient in need of PH treatment via a metered dose inhaler.

In yet another embodiment of Formula (Ia"), (Ib"), (Ic") or (Id"), $R_3$ is OH, $R_5$ is H and $R_2$ is

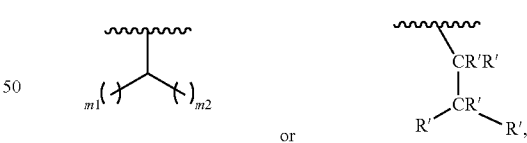

where m1 and m2 are each independently an integer selected from 1 to 9. In even a further embodiment, $R_2$ is

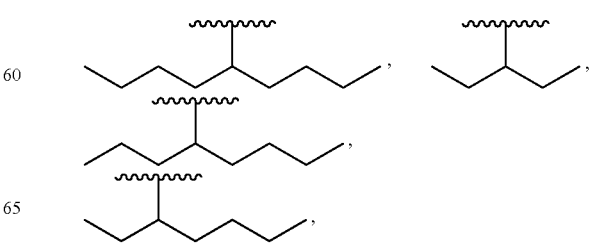

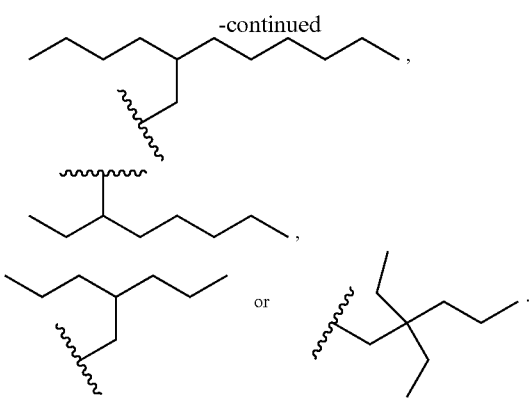

In yet another embodiment of Formula (Ia"), (Ib"), (Ic") or (Id"), $R_2$ is H, $R_3$ is OH, and $R_5$ is

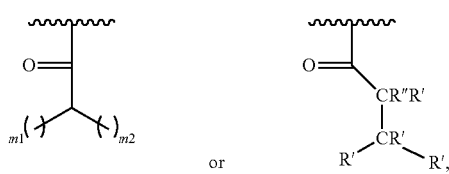

where m1 and m2 are each independently an integer selected from 1 to 9. In even a further embodiment, $R_2$ is

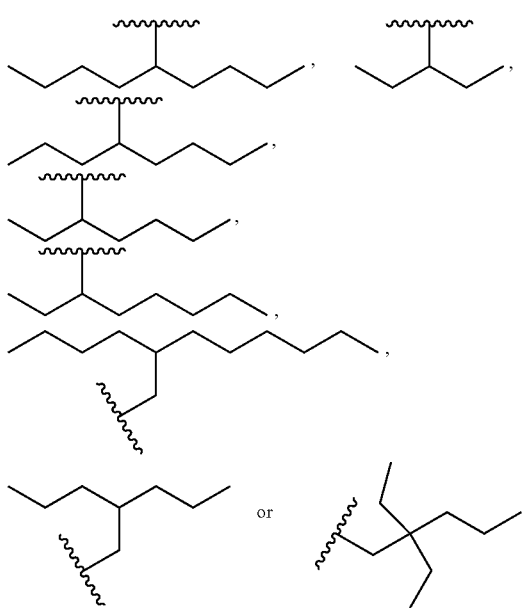

In one embodiment, a prostacyclin compound of Formula (I), (Ia), (Ib), (Ic) or (Id) is provided where $R_2$ is a linear or branched $C_5$-$C_{18}$ alkyl. In a further embodiment, $R_2$ is 5-nonanyl, 4-heptanyl, 4-octanyl, 3-octanyl, 2-dimethyl-1-propanyl, 3,3-dimethyl-1-butanyl, 2-ethyl-1-butanyl, 3-pentanyl, pentyl, hexyl, heptyl, octyl, nonyl, decyl, undecyl, dodecyl, tridecyl, tetradecyl, pentadecyl, hexadecyl, heptadecyl or octadecyl.

In one embodiment, a prostacyclin compound of Formula (I), (Ia), (Ib), (Ic), (Id), (Ia'), (Ib'), (Ic'), (Id'), (Ia"), (Ib"), (Ic") or (Id") is provided where $R_2$ is a linear or branched $C_5$-$C_{18}$ alkyl. In even a further embodiment, $R_2$ is a linear $C_5$-$C_{18}$ alkyl. In another embodiment, $R_2$ is where m1 and m2 are each independently an integer selected from 1 to 9 and each occurrence of R' is independently H, a linear or branched $C_1$-$C_8$ alkyl, or a linear or branched $C_1$-$C_8$ alkenyl. In even a further embodiment, $R_2$ is In another embodiment, a prostacyclin compound of Formula (I), (Ia), (Ib), (Ic) or (Id) is provided wherein $R_2$ is a branched $C_5$-$C_{18}$ alkyl. In a further embodiment, $R_2$ is 5-nonanyl, 4-heptyl, 4-octyl, 3-octyl, 2-dimethyl-1-propyl, 3,3-dimethyl-1-butyl, 2-ethyl-1-butyl, 3-pentyl, pentyl, hexyl, heptyl, octyl, nonyl, decyl, undecyl, dodecyl, tridecyl, tetradecyl, pentadecyl, hexadecyl, heptadecyl or octadecyl.

In one embodiment of the invention, the prostacyclin compound of the invention has the following structure:

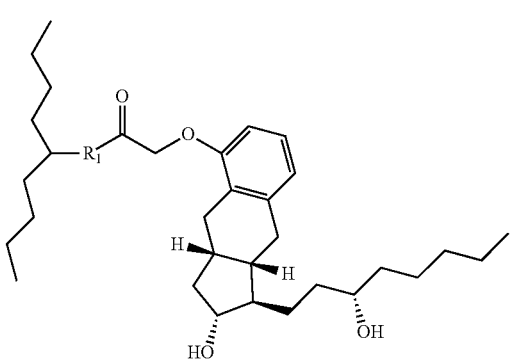

wherein $R_1$ is NH, O of S.

For example, $R_1$ is O or N, and one of the following compounds (5-nonanyl treprostinil (alkyl ester, $5C_9$-TR) or 5-nonanyl treprostinil (amide linked; 5C9-TR-A), is provided:

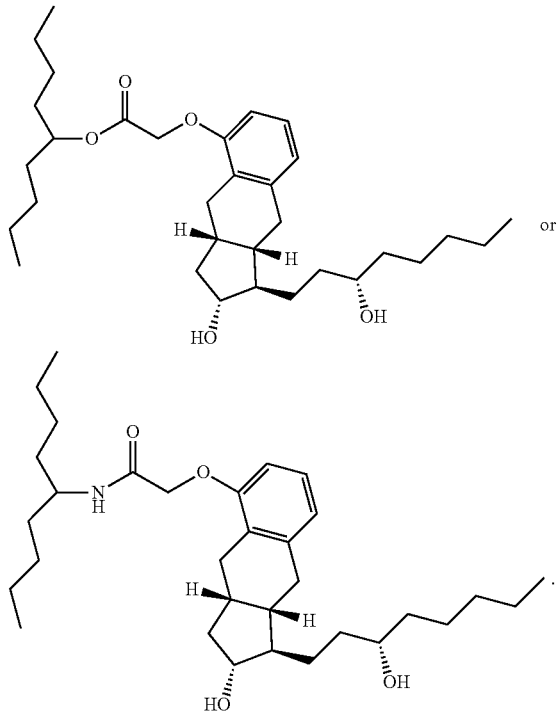

In one embodiment, a prostacyclin compound of Formula (I), (Ia), (Ib), (Ic) or (Id) is provided wherein $R_2$ is

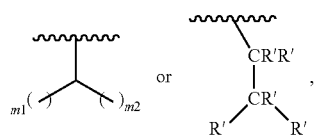

where m1 and m2 are each independently each an integer selected from 1 to 9 and each occurrence of R' is independently H, a linear or branched $C_1$-$C_8$ alkyl, or a linear or branched $C_1$-$C_8$ alkenyl.

When m1 and/or m2 is an integer from 2-9, the m1/m2 at the end of the carbon chain is $CH_3$, while the remaining m1/m2 groups are $CH_2$.

In even another embodiment a compound of Formula (I), (Ia), (Ib), (Ic), (Id), (Ia'), (Ib'), (Ic') (Id'), (Ia"), (Ib") (Ic") or (Id") is provided and $R_2$ is

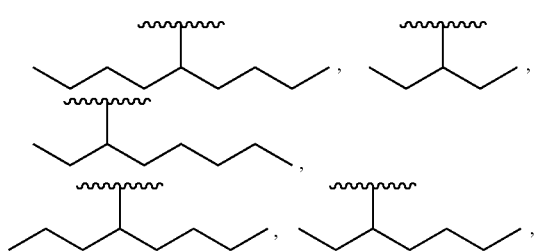

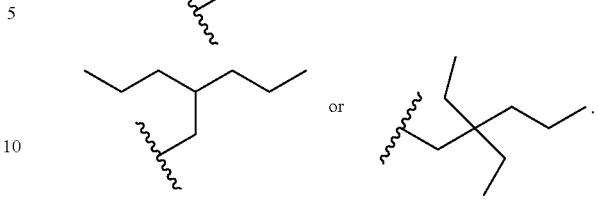

The compounds provided herein can include a symmetrical branched alkyl or an asymmetrical branched alkyl as the $R_2$ moiety. For example, where $R_2$ is

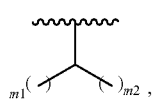

m1 and m2 can be the same integer and $R_2$ is therefore a symmetrical branched alkyl. $R_2$ is an asymmetrical branched alkyl when m1 and m2 are different.

In another embodiment, a compound of Formula (I), (Ia), (Ib), (Ic), (Id), (Ia'), (Ib'), (c'), (Id'), (Ia"), (Ib"), (Ic") or (Id") is provided, $R_2$ is

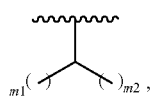

m1 is 2 and m2 is 3, m1 and m2 are each independently 4, or m1 and m2 are each independently 3.

In another embodiment, the prostacyclin compound complies an asymmetrical branched alkyl at the $R_2$ position, such as, for example, 3-hexanyl ($3C_6$), 2-heptanyl ($2C_7$), 3-heptanyl ($3C_7$), 2-octanyl ($2C_8$), 3-octanyl ($3C_8$), or 4-octanyl ($4C_8$).

In another embodiment, a prostacyclin compound of Formula (I), (Ia), (Ib), (Ic) or (Id) is provided wherein $R_2$ is a branched alkyl selected from 2,2-diethyl-1-pentyl, 3-pentyl, 4-octyl, 5-nonanyl, 2-ethyl-1-butyl, 2-propyl-1-pentyl, 12-butyl-1-octyl, 2-dimethyl-1-propyl, and 3,3-dimethyl-1-butyl.

In another embodiment, a prostacyclin compound of Formula (I), (Ia), (Ib), (Ic), (Id), (Ia'), (Ib'), (Ic') or (Id') is provided, wherein, $R_2$ is a linear or branched $C_5$-$C_{18}$ alkenyl. For example, in one embodiment, $R_2$ is a linear $C_5$-$C_{18}$ alkenyl selected from pentenyl, hexenyl, heptenyl, octenyl, nonenyl, decenyl, undecenyl, tridecenyl, tetradecenyl, pentadecenyl, hexadecenyl, heptadecenyl, or octadecenyl. In a further embodiment, $R_3$ is OH. In another embodiment, $R_2$ is a branched $C_5$-$C_{18}$ alkenyl selected from pentenyl, hexenyl, heptenyl, octenyl, nonenyl, decenyl, undecenyl, tridecenyl, tetradecenyl, pentadecenyl, hexadecenyl, heptadecenyl, nonenyl or octadecenyl. In a further embodiment, $R_3$ is OH.

In one embodiment, a prostacyclin compound of Formula (I), (Ia), (Ib), (Ic) or (Id) is provided and $R_4$ is

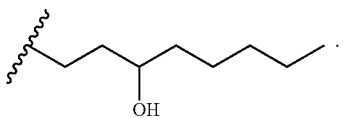 [SMILES: *CCC(O)CCCCC]

In a further embodiment, R$_4$ is

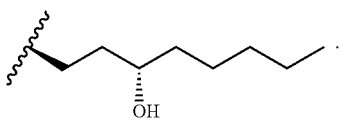

In one embodiment, a prostacyclin compound of Formula (I), (Ia), (Ib), (Ic) or (Id) is provided and R$_2$ a linear C$_5$-C$_{18}$ alkyl, R$_3$ is OH and R$_4$ is

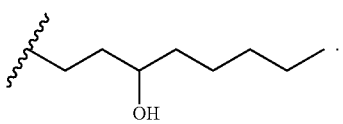 [SMILES: *CCC(O)CCCCC]

In a further embodiment, R$_2$ is 5-nonanyl, 4-heptyl, 4-octanyl, 3-octanyl, 2-dimethyl-1-propyl, 3,3-dimethyl-1-butyl, 2-ethyl-1-butyl, 3-pentyl, pentyl, hexyl, heptyl, octyl, nonyl, decyl, undecyl, dodecyl, tridecyl, tetradecyl, pentadecyl, hexadecyl, heptadecyl or octadecyl.

In one embodiment, a prostacyclin compound of Formula (I), (Ia), (Ib), (Ic) or (Id) is provided and R$_2$ hexyl, dodecyl, tetradecyl, hexadecyl, 5-nonanyl, 4-heptanyl, 4-octanyl, 3-octanyl, 2-dimethyl-1-propyl, 3,3-dimethyl-1-butyl, 2-ethyl-1-butyl, 3-pentyl, R$_3$ is OH and R$_4$ is

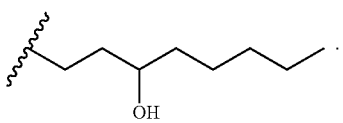 [SMILES: *CCC(O)CCCCC]

In one embodiment, a prostacyclin compound of Formula (I), (Ia), (Ib), (Ic) or (Id) is provided and R$_2$ hexyl, R$_3$ is OH and R$_4$ is

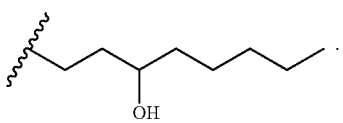 [SMILES: *CCC(O)CCCCC]

In one embodiment, a prostacyclin compound of Formula (I), (Ia), (Ib), (Ic) or (Id) is provided and R$_2$ hexyl, R$_3$ is OH and R$_4$ is

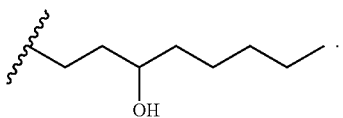 [SMILES: *CCC(O)CCCCC]

In another embodiment, a prostacyclin compound of Formula (Ia″), (Ib″), (Ic″) or (Id″) is provided and R$_2$ hexyl, R$_3$ is OH R$_4$ is H. In a further embodiment, the compound is a compound of Formula (Ic″). In yet another embodiment, a prostacyclin compound of Formula (Ia″), (Ib″), (Ic″) or (Id″) is provided and R$_2$ dodecyl, tetradecyl, pentadecyl or hexadecyl, R$_3$ is OH R$_4$ is H. In a further embodiment, the compound is a compound of Formula (Ia″). In even a further embodiment, the compound is present in a lipid nanoparticle formulation as described in more detail below.

In one embodiment, a prostacyclin compound of Formula (I), (Ia), (Ib), (Ic) or (Id), or pharmaceutically acceptable salt, is provided, and R$_2$ heptyl, R$_3$ is OH and R$_4$ is

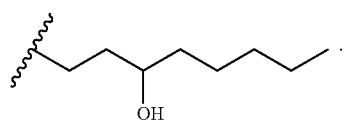 [SMILES: *CCC(O)CCCCC]

In one embodiment, a prostacyclin compound of Formula (I), (Ia), (Ib), (Ic) or (Id), or pharmaceutically acceptable salt, is provided, and R$_2$ octyl, R$_3$ is OH and R$_4$ is

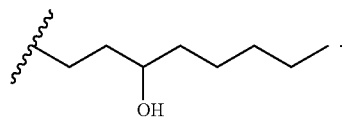 [SMILES: *CCC(O)CCCCC]

In one embodiment, a prostacyclin compound of Formula (I), (Ia), (Ib), (Ic) or (Id), or pharmaceutically acceptable salt, is provided, and R$_2$ nonyl, R$_3$ is OH and R$_4$ is

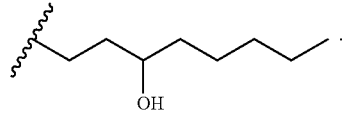 [SMILES: *CCC(O)CCCCC]

In another embodiment, a prostacyclin compound of Formula (I), (Ia), (Ib), (Ic) or (Id), or pharmaceutically acceptable salt, is provided, and R$_2$ decyl, R$_3$ is OH and R$_4$ is

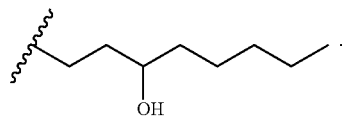 [SMILES: *CCC(O)CCCCC]

In yet another embodiment, a prostacyclin compound of Formula (I), (Ia), (Ib), (Ic) or (Id), or pharmaceutically acceptable salt, is provided, and R$_2$ undecyl, R$_3$ is OH and R$_4$ is

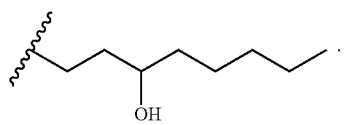

In even another embodiment, a prostacyclin compound of Formula (I), (Ia), (Ib), (Ic) or (Id), or pharmaceutically acceptable salt, is provided, and R₂ dodecyl, R₃ is OH and R₄ is

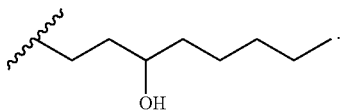 [SMILES: *CCC(O)CCCCC]

In one embodiment, a prostacyclin compound of Formula (I), (Ia), (Ib), (Ic) or (Id), or pharmaceutically acceptable salt, is provided, and R₂ tridecyl, R₃ is OH and R₄ is

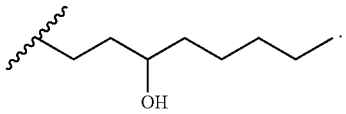 [SMILES: *CCC(O)CCCCC]

In another embodiment, a prostacyclin compound of Formula (I), (Ia), (Ib), (Ic), or (Id), or pharmaceutically acceptable salt, is provided, and R₂ tetradecyl, R₃ is OH and R₄ is

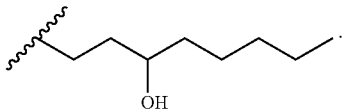 [SMILES: *CCC(O)CCCCC]

In even another embodiment, a prostacyclin compound of Formula (I), (Ia), (Ib), (Ic) or (Id), or pharmaceutically acceptable salt, is provided, and R₂ pentadecyl, R₃ is OH and R₄ is

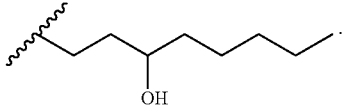

Another embodiment of the invention concerns a prostacyclin compound of Formula (I), (Ia), (Ib), (Ic) or (Id), a or pharmaceutically acceptable salt, wherein R₂ hexadecyl, R₃ is OH and R₄ is

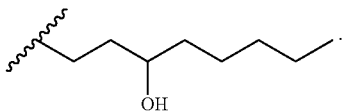 [SMILES: *CCC(O)CCCCC]

Yet another embodiment of the mention concerns a prostacyclin compound of Formula (I), (Ia), (Ib), (Ic) or (Id), a or pharmaceutically acceptable salt, wherein R₂ heptadecyl, R₃ is OH and R₄ is

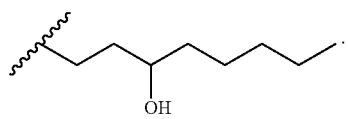 [SMILES: *CCC(O)CCCCC]

Yet another embodiment of the invention concerns a prostacyclin compound of Formula (I), (Ia), (Ib), (Ic) or (Id), or a pharmaceutically acceptable salt, wherein R₂ octadecyl, R₃ is OH and R₄ is

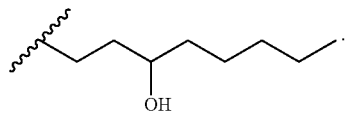 [SMILES: *CCC(O)CCCCC]

In one embodiment, a compound of Formula (I), (Ia), (Ib), (Ic) or (Id), or a pharmaceutically acceptable salt, is provided, wherein one or more hydrogen atoms is substituted with a deuterium. Accordingly, in one embodiment, the present invention relates to an isotopologue of Formula (I), (Ia), (Ib), (Ic) or (Id), substituted with one or more deuterium atoms. The isotopologue of Formula (I), (Ia), (Ib), (Ic) or (Id) may be used to accurately determine the concentration of compounds of Formula (I), (Ia), (Ib), (Ic) or (Id) in biological fluids and to determine metabolic patterns of compounds of Formula (I), (Ia), (Ib), (Ic) or (Id) and its isotopologues. The invention further provides compositions comprising these deuterated isotopologues and methods of treating diseases and conditions, as set forth herein.

In another aspect of the invention, a prostacyclin compound of Formula (II), or a pharmaceutically acceptable salt thereof, is provided:

Formula (II)

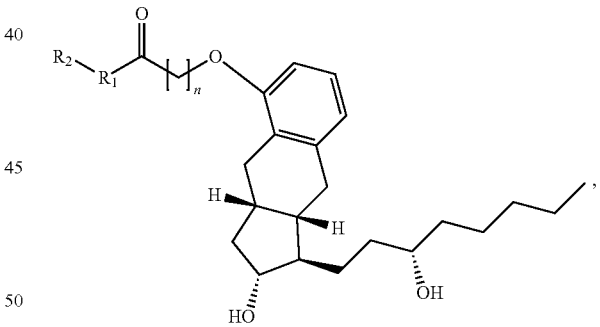

wherein R₁ is NH, O or S;
R₂ is a linear or branched C₅-C₁₈ alkyl, a linear C₂-C₁₈ alkenyl or a branched C₃-C₁₈ alkenyl, aryl, aryl-C₁-C₁₈ alkyl, an amino acid or a peptide; and
n is an integer from 0 to 5.

In one embodiment, a prostacyclin compound of Formula (II), or a pharmaceutically acceptable salt thereof, is provided, wherein R₃ is NH, O or S; R₂ is a linear or branched C₅-C₁₈ alkyl, a linear C₂-C₁₈ alkenyl or a branched C₃-C₁₈ alkenyl; and n is an integer from 0 to 5. In a further embodiment, n is 1 and R₁ is NH or O.

In one embodiment, the present invention relates to the prostacyclin compound of Formula (II), wherein the compound is a compound of formula (IIa), (IIb), (IIc) or (IId), or a pharmaceutically acceptable salt thereof:

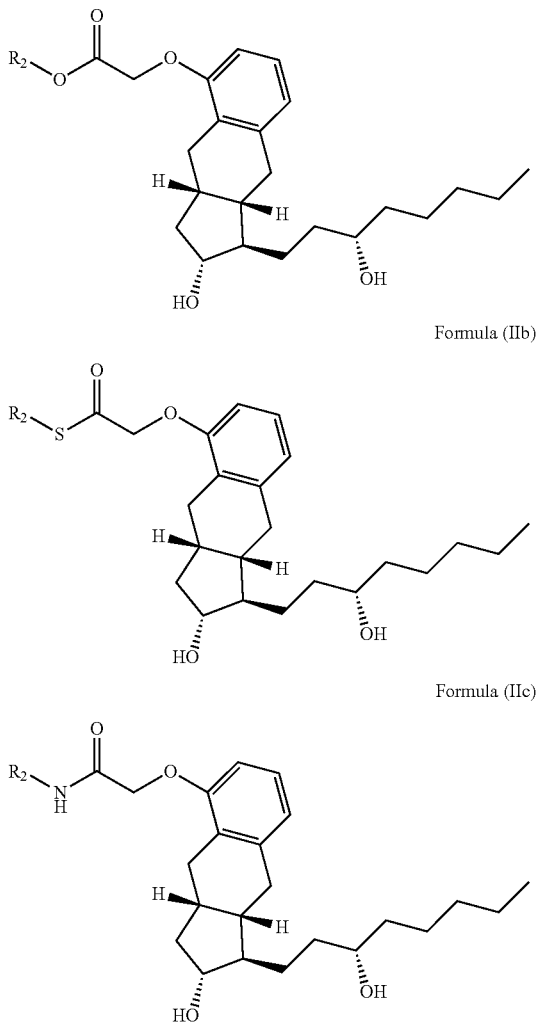

Formula (IIa)

Formula (IIb)

Formula (IIc)

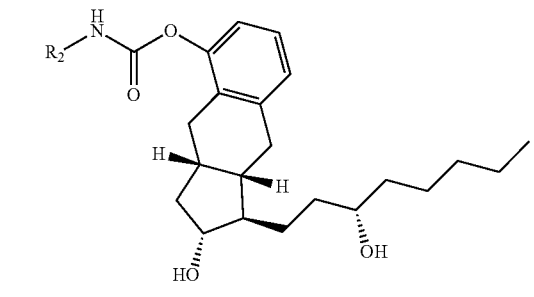

Formula (IId)

wherein $R_2$ is a linear or branched $C_5$-$C_{18}$ alkyl, a linear $C_2$-$C_{18}$ alkenyl or a branched $C_3$-$C_{18}$ alkenyl, aryl, aryl-$C_1$-$C_{18}$ alkyl, an amino acid or a peptide. In a further embodiment, a compound of formula (IIa), (IIb), (IIc) or (IId) is wherein $R_1$ is a linear or branched $C_5$-$C_{18}$ alkyl, a linear $C_2$-$C_{18}$ is alkenyl or a branched $C_3$-$C_{18}$ alkenyl. In one embodiment, a compound of Formula (II), (IIa), (IIb), (IIc) or (IId) is provided, wherein one or more hydrogen atoms is substituted with a deuterium. Accordingly, in one embodiment, the present invention related to an isotopologue of Formula (II), (IIa), (IIb), (IIc) or (IId), substituted with one or more deuterium atoms. The isotopologue of Formula (II), (IIa), (IIb), (IIc) or (IId) may be used to accurately determine the concentration of compounds of Formula (II), (IIa), (IIb), (IIc) or (IId) in biological fluids and to determine metabolic patterns of compounds of Formula (II), (IIa), (IIb), (IIc) of (IId) and its isotopologues. The invention further provides compositions comprising these deuterated isotopologues and methods of treating diseases and conditions as set forth herein.

In one embodiment, the prostacyclin derivative is a compound of Formula (IIc). In a further embodiment, $R_2$ is a linear $C_5$-$C_{18}$ alkyl or a branched $C_5$-$C_{18}$ alkyl. For example, in one embodiment, $R_2$ is a linear $C_6$-$C_{18}$ alkyl. In another embodiment of Formula (IIc), $R_2$ is a linear $C_6$-$C_{19}$ alkyl. In even a further embodiment of Formula (IIc), $R_2$ is a hexyl, heptyl or octyl.

Compounds of Formula (IIa) and Formula (IId) are provided in tables A and B below.

TABLE A

Compounds of Formula (IIa)

| | | | |
|---|---|---|---|
| $R_2$-linear $C_5$—$C_{18}$ alkyl | $R_2$-branched $C_5$—$C_{18}$ alkyl | $R_2$-linear $C_8$ alkyl | $R_2$-branched $C_6$ alkyl |
| $R_2$-linear $C_6$—$C_{18}$ alkyl | $R_2$-branched $C_6$—$C_{18}$ alkyl | $R_2$-linear $C_9$ alkyl | $R_2$-branched $C_7$ alkyl |
| $R_2$-linear $C_7$—$C_{18}$ alkyl | $R_2$-branched $C_7$—$C_{18}$ alkyl | $R_2$-linear $C_{10}$ alkyl | $R_2$-branched $C_8$ alkyl |
| $R_2$-linear $C_8$—$C_{18}$ alkyl | $R_2$-branched $C_8$—$C_{18}$ alkyl | $R_2$-linear $C_{11}$ alkyl | $R_2$-branched $C_9$ alkyl |
| $R_2$-linear $C_9$—$C_{18}$ alkyl | $R_2$-branched $C_9$—$C_{18}$ alkyl | $R_2$-linear $C_{12}$ alkyl | $R_2$-branched $C_{10}$ alkyl |
| $R_2$-linear $C_{10}$—$C_{18}$ alkyl | $R_2$-branched $C_{10}$—$C_{18}$ alkyl | $R_2$-linear $C_{13}$ alkyl | $R_2$-branched $C_{11}$ alkyl |
| $R_2$-linear $C_{11}$—$C_{18}$ alkyl | $R_2$-branched $C_{11}$—$C_{18}$ alkyl | $R_2$-linear $C_{14}$ alkyl | $R_2$-branched $C_{12}$ alkyl |
| $R_2$-linear $C_{12}$—$C_{18}$ alkyl | $R_2$-branched $C_{12}$—$C_{18}$ alkyl | $R_2$-linear $C_{15}$ alkyl | $R_2$-branched $C_{13}$ alkyl |

TABLE B

Compounds of Formula (IIc)

| | | | |
|---|---|---|---|
| $R_2$-linear $C_5$—$C_{18}$ alkyl | $R_2$-branched $C_5$—$C_{18}$ alkyl | $R_2$-linear $C_6$ alkyl | $R_2$-branched $C_6$ alkyl |
| $R_2$-linear $C_6$—$C_{18}$ alkyl | $R_2$-branched $C_6$—$C_{18}$ alkyl | $R_2$-linear $C_7$ alkyl | $R_2$-branched $C_7$ alkyl |
| $R_2$-linear $C_7$—$C_{18}$ alkyl | $R_2$-branched $C_7$—$C_{18}$ alkyl | $R_2$-linear $C_8$ alkyl | $R_2$-branched $C_8$ alkyl |
| $R_2$-linear $C_8$—$C_{18}$ alkyl | $R_2$-branched $C_8$—$C_{18}$ alkyl | $R_2$-linear $C_9$ alkyl | $R_2$-branched $C_9$ alkyl |
| $R_2$-linear $C_9$—$C_{18}$ alkyl | $R_2$-branched $C_9$—$C_{18}$ alkyl | $R_2$-linear $C_{10}$ alkyl | $R_2$-branched $C_{10}$ alkyl |
| $R_2$-linear $C_{10}$—$C_{18}$ alkyl | $R_2$-branched $C_{10}$—$C_{18}$ alkyl | $R_2$-linear $C_{11}$ alkyl | $R_2$-branched $C_{11}$ alkyl |

TABLE B-continued

Compounds of Formula (IIc)

| | | | |
|---|---|---|---|
| $R_2$-linear $C_5$—$C_{12}$ alkyl | $R_2$-branched $C_5$—$C_{12}$ alkyl | $R_2$-linear $C_{12}$ alkyl | $R_2$-branched $C_{12}$ alkyl |
| $R_2$-linear $C_6$—$C_{10}$ alkyl | $R_2$-branched $C_6$—$C_{10}$ alkyl | $R_2$-linear $C_{13}$ alkyl | $R_2$-branched $C_{13}$ alkyl |

Yet another embodiment of the invention relates to a prostacyclin compound of Formula (III), or a pharmaceutically acceptable salt thereof:

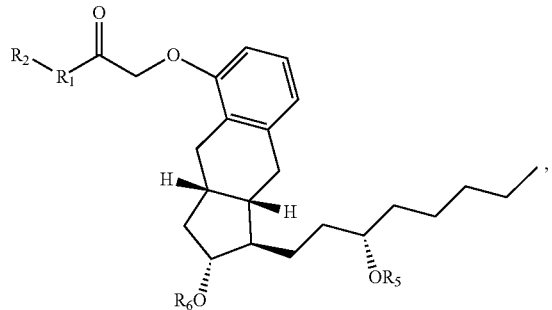

(Formula III)

wherein $R_1$ and $R_2$ are defined as provided for Formula (I) and (II), and $R_5$ and $R_6$ are independently selected from H, optionally substituted linear or branched $C_1$-$C_{15}$ alkyl, optionally substituted linear or branched $C_2$-$C_{15}$ alkenyl, (C=O)-optionally substituted linear or branched $C_1$-$C_{15}$ alkyl, or (C=O)-optionally substituted linear or branched $C_2$-$C_{15}$ alkenyl, with the proviso that the prostacyclin compound of Formula (III) is not treprostinil.

In one embodiment, the branched chain prostacyclin compounds provided herein exhibit both higher solubility and slower enzymatic conversion to treprostinil relative to a linear chain derivatized prostacyclin compound. In one embodiment, an asymmetrical branched chain prostacyclin compound is provided, wherein the asymmetrical branched chain prostacyclin compound is more stable than a corresponding symmetrical branched chain prostacyclin compound.

In one embodiment, the present invention provides prostacyclin compounds that contain a chiral moiety at one or more of the $R_2$, $R_5$ and/or $R_6$ positions. For example, the moiety at position $R_2$, in one embodiment, is a chiral moiety and comprises either the R isomer, the S isomer, or a mixture thereof. An optical isomer at position $R_2$, $R_5$ and/or $R_6$ can also be classified with the D/L nomenclature. For example, where $R_2$ is an amino acid or an amino acid moiety, the amino acid or amino acid moiety can be the D-isomer, L-isomer, or a mixture thereof.

In one embodiment, one of more of the $R_2$, $R_5$ and/or $R_6$ moieties is the R isomer or S isomer. In another embodiment, one or more of the $R_2$, $R_5$ and/or $R_6$ moieties provided herein comprise a mixture of R and S moieties. The "R isomer" or "S isomer" as used herein refers to an enantiomerically pure isomer. An "enantiomerically pure isomer" has at least 90%, at least 95%, at least 96% at least 97%, at least 98%, or at least 99% pure R- or S-isomer or when using the D/L nomenclature. D- or L-isomer. A racemic compound is a compound having a mixture in equal amounts of both enantiomers.

In another aspect of the invention, the prostacyclin compound described herein is provided in a composition, for example, for delivery to a patient for the treatment of pulmonary hypertension (PH). Compositions can include the compound, a pharmaceutically acceptable salt of the compound, or a combination thereof. In one embodiment, the PH is pulmonary arterial hypertension (PAH). Prostacyclin compositions (so called "lipid nanoparticle compositions") and formulations comprising a prostacyclin, a canonic compound, and a surfactant have been described in PCT publication no. WO 2014/085813, the disclosure of which is hereby incorporated by reference in its entirety for all purposes. The compositions described in WO 2014/085813 are amenable for use with the prostacyclin derivative compounds provided herein.

In one embodiment, the composition comprises one of the prostacyclin compounds described herein, i.e., a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), and an amphiphilic agent. When formulated together, in one embodiment, the prostacyclin compound and amphiphilic agent form micro- or nanoparticles. In one embodiment, the amphiphilic agent is a PEGylated lipid, a surfactant or a block copolymer. In another embodiment, the prostacyclin composition provided herein comprises two or more of the prostacyclin compounds described herein (e.g., a compound of Formula (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), including deuterated compounds) and an amphiphilic agent (e.g., PEGylated lipid, a lipid, a surfactant or a block copolymer). In one embodiment, the prostacyclin composition comprising the prostacyclin compound component and amphiphilic agent, when formulated together, comprise a plurality of nanoparticles. In a further embodiment, the mean diameter of the plurality of nanoparticles is from about 20 nm to about 700 nm, for example about 50 nm to about 500 nm, about 100 nm to about 600 nm or about 100 nm to about 500 nm. When the amphiphilic agent comprises a lipid, e.g., a PEGylated lipid such as Cholesterol-PEG or distearoylphosphatidylethanolamine-PEG (DSPE-PEG), the composition is described as comprising lipid nanoparticles.

In a further embodiment, the prostacyclin composition comprises a prostacyclin compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc), (IId), or (III), and a PEGylated lipid as the amphiphilic agent. In a further embodiment, the PEGylated lipid comprises PEG400-PEG5000. For example, in one embodiment, the PEGylated lipid comprises PEG400, PEG500, PEG1000, PEG2000, PEG3000, PEG4000, or PEG5000. In a further embodiment the lipid component of the PEGylated lipid comprises cholesterol, dimyristoyl phosphatidylethanolamine (DMPE), dipalmitoyl phosphoethanolamine (DPPE), distearoylphosphatidylethanolamine (DSPE), dimyristoylglycerol glycerol (DMG), diphosphatidylglycerol (DPG) or disteraroylglycerol (DSG). In even a further embodiment, the PEGylated lipid is cholesterol-PEG2000 or DSPE-PEG2000.

Depending on its molecular weight (MW), PEG is also referred to in the art as polyethylene oxide (PEO) or polyoxyethylene (POE). The PEGylated lipid can include a branched or unbranched PEG molecule, and is not limited by a particular PEG MW.

For example, the PEGylated lipid, in one embodiment, comprises a PEG molecule having a molecular weight of 300 g/mol, 400 g/mol, 500 g/mol, 1000 g/mol, 1500 g/mol, 2000 g/mol, 2500 g/mol, 3000 g/mol, 3500 g/mol, 4000 g/mol, 4500 g/mol, 5000 g/mol, or 10,000 g/mol. In one embodiment, the PEG has a MW of 1000 g/mol or 2000 g/mol.

The lipid component of the PEGylated lipid, can have a net-charge (e.g., cationic or anionic), or can be net-neutral. The lipids used in the PEGylated lipid component of the present invention can be synthetic, semi-synthetic or naturally-occurring lipid, including a phospholipid, a sphingolipid, a glycolipid, a ceramide, a tocopherol, a sterol, a fatty acid, or a glycoprotein such as albumin. In one embodiment, the lipid is a sterol. In a further embodiment, the sterol is cholesterol. In another embodiment, the lipid is a phospholipid. Phospholipids include, but are not limited to phosphatidylcholine (PC), phosphatidyl glycerol (PG), phosphatidylinositol (PI), phosphatidyl serine (PS), phosphatidylethanolamine (PE), and phosphatide acid (PA). In one embodiment the phospholipid is an egg phospholipid, a soya phospholipid or a hydrogenated egg and soya phospholipid. In one embodiment, the PEGylated lipid comprises a phospholipid. In a further embodiment, the phospholipid comprises ester linkages of fatty acids in the 2 and 3 of glycerol positions containing chains of 12 to 26 carbon atoms and different head groups in the 1 position of glycerol that include choline, glycerol, inositol serine, ethanolamine, as well as the corresponding phosphatide acids. The chains on these fatty acids can be saturated or unsaturated, and the phospholipid can be made up of fatty acids of different chain lengths and different degrees of unsaturation. In particular, in one embodiment, the PEGylated lipid of the prostacyclin composition provided herein comprises distearoylphosphoethanol amine (DSPE), dipalmitoylphosphatidylcholine (DPPC), dioleoylphosphatidylcholine (DOPC) dimyristoyl phosphatidylethanolamine (DMPE), dipalmitoylphosphoethanolamine (DPPE), distearoylphosphatidylethanolamine (DSPE), dimyristoylglycerol (DMG), diphosphatidylglycerol (DPG) or disteraroylglycerol (DSG).

Other examples of lipids for use in the compositions comprising PEGylated lipids disclosed herein include dimyristoyl phosphatidylcholine (DMPC), dimyristoylphosphatidylglycerol (DMPG), dipalmitoylphosphatidylglycerol (DPPG), distearoylphasphatidylcholine (DSPC), distearoylphosphatidylglycerol (DSPG) dioleylphosphatidylethanolamine (DOPE), and mixed phospholipids such as palmitoylstearoylphosphatidylcholine (PSPC) and palmitoylstearoylphosphatidylglycerol (PSPG), triacyglycerol, diacylglycerol, ceramide, sphingosine, sphingomyelin and single acylated phospholipids such as mono-oleoyl-phosphatidylethanolamine (MOPE). In another embodiment lipid portion of the PEGylated lipid comprises an ammonium salt of a fatty acid, a phospholipid, a glyceride, a phospholipid and glyceride, a sterol (e.g. cholesterol), phosphatidylglycerol (PG), phosphatide acid (PA), a phosphotidylcholine (PC), a phosphatidylinositol (PI), a phosphatidylserine (PS), or a combination thereof. The fatty acid, in one embodiment, comprises fatty acids of carbon chain lengths of 12 to 26 carbon atoms that are either saturated or unsaturated. Some specific examples include: myristylamine, palmitylamine, laurylamine and stearyl amine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9 (Z)-octadecenyloxy)-prop-1-yl-N,N,N-trimethylammonium chloride (DOTMA) and 1,2-bis(oleoyloxy)-3-trimethylammonio)propane (DOTAP). Examples of sterols for use in the compositions provided herein include cholesterol and ergosterol. Examples of PGs, PAs, PIs, PCs and PSs for use in the compositions provided herein include DMPG, DPPG, DSPG, DMPA, DPPA, DSPA, DMPI, DPPI, DSPI, DMPS, DPPS and DSPS, DSPC, DPPG, DMPC, DOPC, egg PC and soya PC.

In one embodiment, the PEGylated lipid is cholesterol-PEG2000, DSPE-PEG1000 or DSG-PEG2000.

In another embodiment, the prostacyclin composition provided herein comprises a prostacyclin compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), and a hydrophobic additive. In a further embodiment, the composition comprises an amphiphilic agent, e.g., a PEGylated lipid, as described above.

In yet another embodiment, two or more of the prostacyclin compounds described herein (e.g., a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III)) an amphiphilic agent (e.g., PEGylated lipid, a lipid, a surfactant or a block copolymer) and a hydrophobic additive are provided in a composition.

In one embodiment, the prostacyclin composition comprises a prostacyclin compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III) and a PEGylated lipid. In another embodiment, the prostacyclin composition comprises a prostacyclin compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III) and a surfactant. In yet another embodiment, the prostacyclin composition comprises a prostacyclin compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), a hydrophobic additive and an amphiphilic agent. In a further embodiment, the amphiphilic agent is a surfactant, a PEGylated lipid or a block copolymer. In even a further embodiment, the amphiphilic agent is a PEGylated lipid.

In one embodiment, the prostacyclin compound is present in the composition at 5 mol %-99 mol %. In a further embodiment, the prostacyclin compound is present in the composition at 40 mol %-95 mol %. In a further embodiment, the prostacyclin compound is present in the composition at 40 mol %-60 mol %. In one embodiment, the prostacyclin compound is present in the composition at about 40 mol % or about 45 mol %.

The amphiphilic agent, e.g., a PEGylated lipid, when present in the composition, in one embodiment, is present at 10 mol %-30 mol %, for example, 10 mol %-20 mol % or 15 mol %-25 mol %. In even a further embodiment, the PEGylated lipid is present in the composition at about 10 mol % or 20 mol %.

The hydrophobic additive, when present in the composition, in one embodiment, is present in the composition at 25 mol %-50 mol %, for example, 30 mol %-50 mol %, 35 mol %-45 mol %. In even a further embodiment, the hydrophobic additive is present in the composition at about 40 mol % or about 45 mol %.

The prostacyclin composition, in one embodiment, comprises a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or a pharmaceutically acceptable salt thereof, as described herein, an amphiphilic agent and a hydrophobic additive. In one embodiment, the hydrophobic additive (e.g., an additive that is at least partially hydrophobic) is a hydrocarbon, a terpene compound or a hydrophobic lipid (e.g., tocopherol, tocopherol acetate, sterol, sterol ester, alkyl ester, vitamin A acetate, a triglyceride, a phospholipid). In one embodiment, the composition comprises a prostacyclin compound, for example, a compound of Formula (I) or (II), an amphiphilic agent, and a hydrocarbon. The hydrocarbon can be aromatic, an alkane, alkene, cycloalkane or an alkyne. In one embodiment, the hydrocarbon is an alkane (i.e., a saturated hydrocarbon). In another embodiment, the hydrocarbon is a $C_{15}$-$C_{50}$ hydrocarbon. In a further embodiment, the hydrocarbon is a $C_{15}C_{20}$, $C_{25}$, $C_{30}$, $C_{35}$, $C_{40}$, $C_{45}$ or $C_{50}$ hydrocarbon. In yet another embodiment, the hydrophobic additive is a $C_{15}$-$C_{25}$ hydrocarbon, $C_{15}$-$C_{35}$ hydrocarbon, $C_{15}$-$C_{45}$ hydrocarbon, $C_{15}$-$C_{20}$ hydrocarbon, $C_{20}$-$C_{45}$ hydrocarbon, $C_{25}$ hydrocarbon, $C_{25}$-$C_{30}$ hydrocarbon, $C_{30}$-$C_{35}$ hydrocarbon, $C_{35}$-$C_{40}$ hydrocarbon, $C_{40}$-$C_{45}$ hydrocarbon or a $C_{45}$-$C_{50}$ hydrocarbon.

In one embodiment, a composition comprising a prostacyclin compound, an amphiphilic agent and a terpene compound (e.g., the hydrophobic additive) is provided. The composition, in a further embodiment, comprises a PEGylated lipid as the amphiphilic agent. However, as noted above, block copolymers as well as surfactants can be used as the amphiphilic component of the composition. The terpene compound (hydrophobic additive), in one embodiment, is a hydrocarbon (e.g., isoprene, squalane or squalene). In another embodiment, the terpene compound is a hemiterpene ($C_5H_8$), monoterpene ($C_{10}H_{16}$), sesquiterpene ($C_{15}H_{24}$), diterpene ($C_{20}H_{32}$) (e.g., cafestol, kahweol, cembrene, taxadiene), sesterterpene ($C_{25}H_{40}$), triterpene ($C_{30}H_{48}$), sesquaterpene ($C_{35}H_{56}$), tetraterpene ($C_{40}H_{64}$), polyterpene (e.g., a polyisoprene with trans double bonds) on a norisoprenoid (e.g., 3-oxo-α-ionol, 7,8-dihydroionone derivatives). The terpene compound, in another embodiment, is selected from one of the compounds provided in Table 1, below. In one embodiment, the hydrophobic additive is squalane.

TABLE 1

Terpene hydrophobic additives amenable for use in the compositions of the present invention.

| Name | Formula |
| --- | --- |
| Isoprene | |
| Limonene | |
| humulene | |
| farnasene | |
| squalene | |
| squalane | |

As provided above, the composition provided herein, in one embodiment, composes a prostacyclin compound and one or more PEGylated lipids. In a further embodiment, the composition comprises a hydrophobic additive, as described above. In one embodiment, the composition provided herein comprises a prostacyclin compound of one of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), a hydrophobic additive and a PEGylated lipid. In a further embodiment, the hydrophobic additive comprises a hydrocarbon e.g. a terpene compound.

In one embodiment, the treprostinil derivative composition provided herein includes the components provided in Table C, below.

TABLE C

| Compound # | Treprostinil compound | Hydrophobic additive | Amphiphilic agent | Additional lipid |
|---|---|---|---|---|
| 1 | Formula (II) where $R_1$ is O, $R_2$ is linear $C_6$—$C_{16}$ | Terpene | PEGylated lipid | n/a |
| 2 | Formula (II) where $R_1$ is O, $R_2$ is linear $C_6$—$C_{16}$ | Terpene | PEGylated lipid | DOPC |
| 3 | Formula (II) where $R_1$ is O, $R_2$ is linear $C_6$—$C_{16}$ | Squalane | Chol-PEG2k | n/a |
| 4 | Formula (II) where $R_1$ is O, $R_2$ is linear $C_6$—$C_{16}$ | Squalane | DSPE-PEG2k | n/a |
| 5 | Formula (II) where $R_1$ is O, $R_2$ is linear $C_{10}$—$C_{16}$ | Terpene | PEGylated lipid | n/a |
| 6 | Formula (II) where $R_1$ is O, $R_2$ is linear $C_{10}$—$C_{16}$ | Terpene | PEGylated lipid | DOPC |
| 7 | Formula (II) where $R_1$ is O, $R_2$ is linear $C_{10}$—$C_{16}$ | Squalane | Chol-PEG2k | n/a |
| 8 | Formula (II) where $R_1$ is O, $R_2$ is linear $C_{10}$—$C_{16}$ | Squalane | DSPE-PEG2k | n/a |
| 9 | Formula (II) where $R_1$ is O, $R_2$ is linear $C_{12}$—$C_{16}$ | Terpene | PEGylated lipid | n/a |
| 10 | Formula (II) where $R_1$ is O, $R_2$ is linear $C_{12}$—$C_{16}$ | Terpene | PEGylated lipid | DOPC |
| 11 | Formula (II) where $R_1$ is O, $R_2$ is linear $C_{12}$—$C_{16}$ | Squalane | Chol-PEG2k | n/a |
| 12 | Formula (II) where $R_1$ is O, $R_2$ is linear $C_{12}$—$C_{16}$ | Squalane | DSPE-PEG2k | n/a |
| 13 | Formula (II) where $R_1$ is O, $R_2$ is linear $C_6$—$C_{16}$ | Terpene | PEGylated lipid | n/a |
| 14 | Formula (II) where $R_1$ is O, $R_2$ is linear $C_6$—$C_{16}$ | Terpene | PEGylated lipid | DOPC |
| 15 | Formula (II) where $R_1$ is O, $R_2$ is linear $C_6$—$C_{16}$ | Squalane | Chol-PEG2k | n/a |
| 16 | Formula (II) where $R_1$ is O, $R_2$ is linear $C_6$—$C_{16}$ | Squalane | DSPE-PEG2k | n/a |
| 17 | Formula (II) where $R_1$ is N, $R_2$ is linear $C_6$—$C_{16}$ | Terpene | PEGylated lipid | n/a |
| 18 | Formula (II) where $R_1$ is N, $R_2$ is linear $C_6$—$C_{16}$ | Terpene | PEGylated lipid | DOPC |
| 19 | Formula (II) where $R_1$ is N, $R_2$ is linear $C_6$—$C_{16}$ | Squalane | Chol-PEG2k | n/a |
| 20 | Formula (II) where $R_1$ is N, $R_2$ is linear $C_6$—$C_{16}$ | Squalane | DSPE-PEG2k | n/a |
| 21 | Formula (II) where $R_1$ is N, $R_2$ is linear $C_6$—$C_{10}$ | Terpene | PEGylated lipid | n/a |
| 22 | Formula (II) where $R_1$ is N, $R_2$ is linear $C_6$—$C_{10}$ | Terpene | PEGylated lipid | DOPC |
| 23 | Formula (II) where $R_1$ is N, $R_2$ is linear $C_6$—$C_{10}$ | Squalan | Chol-PEG2k | n/a |
| 24 | Formula (II) where $R_1$ is N, $R_2$ is linear $C_6$—$C_{10}$ | Squalane | DSPE-PEG2k | n/a |

The present invention also provides methods for treating a patient in need thereof, with one of the prostacyclin compounds or compositions described herein. It is understood that reference to a prostacyclin compound in a treatment method includes the use of a pharmaceutically acceptable salt of the compound. Similarly, administration of a prostacyclin composition comprising a prostacyclin compound includes the use of a pharmaceutically acceptable salt in the composition.

In one aspect, a method for treating pulmonary hypertension (PH) is provided. The method comprises, in one embodiment, administration of a compound, pharmaceutically acceptable salt thereof, or composition provided herein to a patient in need thereof. Administration, in one embodiment, is pulmonary administration and can be, for example, with a metered dose inhaler (MDI), dry powder inhaled (DPI), or a nebulizer. The World Health Organization (WHO) has classified PH into five groups. WHO Group I PH includes pulmonary arterial hypertension (PAH), idiopathic pulmonary arterial hypertension (IPAH), familial pulmonary arterial hypertension (FPAH), and pulmonary arterial hypertension associated with other diseases (APAH). For example, pulmonary arterial hypertension associated with collagen vascular disease (e.g., scleroderma), congenital shunts between the systemic and pulmonary circulation, portal hypertension and/or HIV infection are included in group I PH. The methods provided herein, in one embodiment, are provided to treat a WHO Group I PH patient in need thereof, for example a PAH patient, an IPAH patient, a FPAH patient or an APAH patient. WHO Group II PH includes pulmonary hypertension associated with left heart disease, e.g., atrial or ventricular disease, or valvular disease (e.g., mitral stenosis). The methods provided herein, in one embodiment, are provided to treat a WHO Group II patient in need thereof. WHO group III pulmonary hypertension is characterized as pulmonary hypertension associated with lung diseases, e.g., chronic obstructive pulmonary disease (COPD), interstitial lung disease (ILD), and/or hypoxemia. The methods provided herein, in one embodiment, are provided to treat a WHO Group III patient in need thereof. WHO Group IV pulmonary hypertension is pulmonary hypertension due to chronic thrombotic and/or embolic disease. Group IV PH is also referred to as chronic thromboembolic pulmonary hypertension Group IV PH patients experience blocked or narrowed blood vessels due to blood clots. The methods provided herein, in one embodiment, are provided to treat a WHO Group IV patient in need thereof. WHO categorizes Group V PH as the "miscellaneous" category, and includes PH caused by blood disorders (e.g., polycythemia vera, essential thrombocythemia), systemic disorders (e.g., sarcoidosis, vasculitis) and/or metabolic disorders (e.g., thyroid disease, glycogen storage disease). The methods provided herein, in one embodiment, are provided to treat a WHO Group V patient in need thereof.

The methods provided herein can be used to treat a WHO Group I (i.e., pulmonary arterial hypertension or PAH). Group II, Group III, Group IV or Group V PH patient. In one embodiment of the method for treating PH, a method of treating pulmonary arterial hypertension (PAH) is provided. In another embodiment, a method for treating chronic thromboembolic pulmonary hypertension patient is provided. In one embodiment, the method for treating PH (e.g., PAH) comprises administering an effective amount of one of the compounds described herein via a pulmonary (inhalation, e.g., via an MDI or nebulizer or dry powder inhaler), a subcutaneous, oral, nasal or an intravenous route of administration, to a patient in need thereof. In one embodiment, administration is via inhalation via an MDI or nebulizer. In one embodiment, where compound delivery is via a nebulizer, the compound is provided to the patient as a composition, for example, as a lipid nanoparticle composition, as described above.

In another aspect of the invention, a method for treating portopulmonary hypertension (PPH) is provided. In one embodiment the method comprises administering an effective amount of one of the compounds described herein (or a pharmaceutically acceptable salt thereof), via a pulmonary (inhalation), a subcutaneous, oral, nasal or an intravenous route of administration, to a patient in need thereof. In one embodiment, administration is via inhalation via an MDI or nebulizer. In one embodiment, where compound delivery is via a nebulizer, the compound is provided to the patient as a composition, for example, as a lipid nanoparticle composition, as described above.

Methods for administering treprostinil and analogs thereof for treatment of pulmonary hypertension have been described in U.S. Pat. Nos. 5,153,222; 6,521,212; 7,544,713 and U.S. Patent Application Publication No 2010/0076083, the disclosure of each are incorporated by reference in their entireties for all purposes.

The method for treating a patient for PH (e.g., PAH) or PPH comprises in one embodiment, administering to a patient in need thereof, one of the prostacyclin compounds or compositions provided herein, for example, a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), a pharmaceutically acceptable salt thereof, or a composition comprising a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or a pharmaceutically acceptable salt thereof. In one embodiment, the method for treating PH (e.g., PAH) or PPH comprises administering to a patient in need thereof, one of the prostacyclin compounds or compositions provided herein, for example, a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or a composition comprising a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc), (IId), or (III), or a composition comprising a deuterated compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III). Routes of administration to the patient include pulmonary (inhalation), subcutaneous, oral, nasal and intravenous. In one embodiment, administration of a compound of Formula (I), (Ia) (Ib), (Ic), (Id), (Ia'), (Ib'), (Ic'), (Id'), (Ia"), (Ib"), (Ic"), (Id"), (II), (IIa), (IIb), (IIc) (IId), or (III), or a pharmaceutically acceptable salt thereof, is via inhalation via an MDI or nebulizer. In one embodiment, where compound delivery is via a nebulizer, the compound is provided to the patient as a composition, for example, as a lipid nanoparticle composition, as described above.

In one embodiment, the method for treating PH, PAH or PPH comprises administering to a patient in need thereof, an effective amount of the prostacyclin compound or prostacyclin composition described herein. In a further embodiment, the compound, or a pharmaceutically acceptable salt of the compound, is administered to the patient via a pulmonary (inhalation), a subcutaneous, oral, nasal or an intravenous route of administration. In a further embodiment, administration is via inhalation and the prostacyclin compound or composition is administered with a nebulizer, dry powder inhaler, or MDI. In even a further embodiment the prostacyclin composition or composition comprises a prostacyclin compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or a deuterated version thereof or a pharmaceutically acceptable salt of the compound.

In one embodiment, administration of an effective amount of a prostacyclin compound or composition of the present invention for the treatment of PH, PAH or PPH via inhalation, oral, nasal, subcutaneous or intravenous administration results in a decreased number of side effects, or a reduced severity of one or more side effects (also referred to herein as "adverse events"), compared to the administration of an effective amount of treprostinil, when an effective amount of treprostinil is administered via inhalation, oral, nasal, subcutaneous, or intravenous administration. For example, in one embodiment, a PH, PAH or PPH patient experiences a reduced severity and/or frequency in cough or a reduced cough response when administered a prostacylin compound or composition of the invention via inhalation (e.g., nebulization, dry powder inhaler, or via a metered dose inhaler), compared to the severity and/or frequency of cough or cough response elicited by inhalation administration of treprostinil to the patient.

In another embodiment, oral, nasal, intravenous, subcutaneous or inhalation administration of an effective amount of the prostacyclin compound or composition of the invention, compared to oral, nasal, subcutaneous, intravenous or inhalation administration of treprostinil, results in a reduced severity of one or more of the following adverse events, or a decreased occurrence of one or more of the following adverse events headache, throat irritation/pharyngolaryngeal pain, nausea, flushing and/or syncope.

In another embodiment, oral, nasal, intravenous, subcutaneous or inhalation administration of an effective amount of the prostacyclin compound or composition of the invention, for the treatment of PH, PAH or PPH, compared to oral, nasal, subcutaneous, intravenous or inhalation administration of treprostinil, results in a reduced severity of a systemic adverse event, or a decreased occurrence of a systemic adverse event.

Without wishing to be bound by theory, it is believed that the improved adverse event profile of the prostacylin compounds and compositions of the invention exhibited patients, as compared to treprostinil, results in improved compliance of the patients.

In one embodiment, the prostacyclin compounds and compositions of the present invention are administered on a less frequent basis, as compared to currently approved therapies for PH, PAH (e.g., Tyvaso®, Remodulin®) or PPH, while still achieving a substantially equivalent or better therapeutic response. Routes of administration to the patient include pulmonary (inhalation), subcutaneous, oral, nasal and intravenous. The therapeutic response of the patient, in one embodiment, is a reduction in the pulmonary vascular resistance index (PVRI) from pretreatment value, a reduction in mean pulmonary artery pressure from pretreatment value, an increase in the hypoxemia score from pretreatment value, a decrease in the oxygenation index from pretreatment values, improved right heart function, as compared to pretreatment or improved exercise capacity (e.g., as measured by the six-minute walk test) compared to pretreatment. The therapeutic response, in one embodiment, is an improvement of at least 10%, at least 20%, at least 30%, at least 40% or at least 50%, as compared to pretreatment values. In another embodiment, the therapeutic response is an improvement of about 105 to about 70%, about 10% to about 60%, about 10% to about 50%, about 10% to about 40%, about 10% to about 30%, about 10% to about 20%, about 20% to about 70%, about 20% to about 60% or about 10% to about 50%, as compared to pretreatment levels.

Without wishing to be bound by theory, the less frequent administration of the compounds and compositions of the invention allows for improved patient compliance, as compared to the compliance of patients being administered a different PH, PAH or PPH treatment (e.g., treprostinil—Tyvaso®, Remodulin®).

In one embodiment, a composition or compound of the present invention is administered via a metered dose inhaler (MDI) to a patient in need of PH, PAH or PPH treatment. The composition or compound, in one embodiment, is delivered via a MDI by the use of a propellant, for example, a chloro-fluorocarbon (CFC) or a fluorocarbon. In one embodiment, where delivery is via an MDI, the compound is not formulated as a lipid nanoparticle composition, and instead, is suspended or dissolved directly in a propellant solution. The patient, in one embodiment, is administered the prostacyclin compound or composition of the invention once daily, twice daily or three limes daily. In one embodiment, the administration is with food. In one embodiment, each administration comprises 1 to 5 doses (puffs) from an MDI, for example 1 dose (1 puff), 2 dose (2 puffs), 3 doses (3 puffs), 4 doses (4 puffs) or 5 doses (5 puffs). The MDI, in one embodiment is small and transportable by the patient.

In another embodiment the prostacyclin compound or prostacyclin composition is administered via a nebulizer to a patient in need of PH, PAH or PPH treatment. The administration occurs in one embodiment, once daily, twice daily, three times daily or once every other day.

In one embodiment, a composition or compound of the present invention is administered via a dry powder inhaler (DPI) to a patient in need of PH, PAH or PPH treatment. The patient, in one embodiment, is administered the prostacyclin compound or composition of the invention once daily, twice daily or three times daily. In one embodiment, the administration is with food. In one embodiment, each administration comprises 1 to 5 doses (puffs) from a DPI, for example 1 dose (1 puff), 2 dose (2 puffs), 3 doses (3 puffs), 4 doses (4 puffs) or 5 doses (5 puffs). The DPI, in one embodiment, is small and transportable by the patient.

In another embodiment, the prostacyclin compound administered to a patient in need thereof via a pulmonary route by the PH, PAH or PAH treatment methods described herein provides a greater pulmonary elimination half-life ($t_{1/2}$) of the prostacyclin compound or its treprostinil metabolite, compared to the pulmonary elimination half-life ($t_{1/2}$) of treprostinil, when treprostinil is administered via a pulmonary route (e.g., by nebulization, dry powder inhaler, or a metered dose inhaler) to the patient in need of PH, PAH or PPH treatment.

In another embodiment, the prostacyclin compound administered to a patient in need thereof, via the PH, PAH or PPH treatment methods described herein provides a greater systemic half-life ($t_{1/2}$) of the prostacyclin compound or its treprostinil metabolite, compared to the systemic elimination half-life ($t_{1/2}$) of treprostinil, when treprostinil is administered to the patient. In a further embodiment, administration of the prostacyclin compound and treprostinil comprises oral, nasal, subcutaneous or intravenous administration.

In another embodiment, the prostacyclin compound administered to a patient in need of PH, PAH or PPH treatment provides a greater mean pulmonary $C_{max}$ and/or lower plasma $C_{max}$ of treprostinil for the patient, compared to the respective pulmonary or plasma $C_{max}$ of treprostinil, when treprostinil is administered to the patient. In a further embodiment, administration of the prostacyclin compound and treprostinil comprises intravenous administration.

In another embodiment, the prostacyclin compound administered to a patient in need of PH, PAH or PPH treatment provides a sweater mean pulmonary or plasma area under the curve ($AUC_{0-t}$) of the prostacyclin compound or its treprostinil metabolite, compared to the mean pulmonary or plasma area under the curve ($AUC_{0-t}$) of treprostinil, when treprostinil is administered to the patient. In yet another embodiment, the prostacyclin compound administered to a patient in need thereof provides a greater pulmonary or plasma time to peak concentration ($t_{max}$) of treprostinil, compared to the pulmonary or plasma time to peak concentration ($t_{max}$) of treprostinil, when treprostinil is administered to the patient.

In another aspect of the invention, a method of treating a disease, disorder or condition other than PH, PAH or PPH is provided U.S. Pat. No. 5,153,222, incorporated by reference herein in its entirety, describes use of treprostinil for treatment of pulmonary hypertension. Treprostinil is approved for the intravenous as welt as subcutaneous route, the latter avoiding potential septic events associated with continuous intravenous catheters. U.S. Pat. Nos. 6,521,212 and 6,756,033, each incorporated by reference herein in their entireties, describe administration of treprostinil by inhalation for treatment of pulmonary hypertension, peripheral vascular disease and other diseases and conditions. U.S. Pat. No. 6,803,386, incorporated by reference herein in its entirely, discloses administration of treprostinil for treating cancer such lung, liver, brain, pancreatic, kidney, prostate, breast, colon and head-neck cancer. U.S. Patent Application Publication No. 2005/0165111, incorporated by reference herein in its entirety, discloses treprostinil treatment of ischemic lesions. U.S. Pat. No. 7,199,157, incorporated by reference herein in its entirety, discloses that treprostinil treatment improves kidney functions. U.S. Pat. No. 7,879,909, incorporated by reference herein in its entirety, discloses treprostinil treatment of neuropathic foot ulcers U.S. Patent Application Publication No. 2008/0280986, incorporated by reference herein in its entirety, discloses treprostinil treatment of pulmonary fibrosis, interstitial lung disease with treprostinil and asthma. U.S. Pat. No. 6,054,486, incorporated by reference herein in its entirety, discloses treatment of peripheral vascular disease with treprostinil U.S. patent application publication no. 2009/0036465, incorporated by reference herein in its entirety, discloses combination therapies comprising treprostinil. U.S. Patent Application Publication No 2003/0200449 discloses delivery of treprostinil using a metered dose inhaler. U.S. Pat. Nos. 7,417,070, 7,384,978 and 7,544,713 as well as U.S. Patent Application Publication Nos 2007/0078095, 2005/0282901, and 2008/0249167, each incorporated by reference herein in their entireties, describe oral formulations of treprostinil and other prostacyclin analogs as well as their use for treatment of a variety of conditions. U.S. Patent Application Publication No. 2012/0004507, incorporated by reference herein, discloses the use of orally administered treprostinil for treatment of Raynaud's phenomenon, systemic sclerosis and digital ischemic lesions. Each of the indications recited above can be treated with the compounds and compositions provided herein. Routes of administration to a patient in need of treatment include pulmonary (inhalation), subcutaneous, oral, nasal and intravenous.

Additionally, the following references are incorporated by reference in their entireties for all purposes for practicing the embodiments of the present invention: J. Org. Chem. 2004, 69, 1890-1902, Drug of the Future, 2001, 26(4), 364-374, U.S. Pat. Nos. 5,153,222, 6,054,486, 6,521,212, 6,756,033, 6,803,386, and 7,199,157, U.S. Patent Application Publication Nos. 2005/0165111, 2005/0282903, 2008/0200449, 2008/0280986, 2009/0036465 and 2012/0010159.

In one embodiment, a method is provided for treating a patient in need thereof for congestive heart failure, peripheral vascular disease, asthma, severe intermittent claudication, immunosuppression, proliferative diseases, e.g., cancer such as lung, liver, brain, pancreatic, kidney, prostate, breast, colon and head-neck cancer, ischemic lesions, neuropathic foot ulcers, and pulmonary fibrosis, kidney function and/or interstitial lung disease. In one embodiment, the method comprises administering an effective amount of one of the prostacyclin compounds or compositions provided herein, for example, a compound of Formula (I), (Ia), (Ib), (Ic), (Id), (Ia'), (Ib'), (Ic'), (Id'), (Ia"), (Ib"), (Ic"), (Id"), (II) (IIa), (IIb), (IIc) (IId), or (III), or a deuterated version thereof, or a composition comprising a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or a composition comprising a deuterated compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III) to the patient. Administration, in one embodiment, is via inhalation (e.g., with a nebulizer or metered dose inhaler), subcutaneous, oral, nasal or intravenous. In some embodiments, the pharmaceutical formulation may comprise one or more active ingredients in addition to treprostinil monohydrate.

In one embodiment, a method is provided for treating and/or preventing interstitial lung disease (e.g., pulmonary fibrosis) or asthma, or a condition associated with interstitial lung disease or asthma in a patient in need of such treatment. In a further embodiment, the method comprises administering to the patient an effective amount of one of the prostacyclin compounds or compositions provided herein, for example, a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or a deuterated version thereof, or a composition comprising a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or a composition comprising a deuterated compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III). The composition or compound, in one embodiment, is delivered via a MDI by the use of a propellant, for example, a chloro-fluorocarbon (CFC) or a fluorocarbon. The patient, in one embodiment, is administered the prostacyclin compound or composition of the invention once daily, twice daily or three times daily. In one embodiment, the administration is with food. In one embodiment, each administration comprises 1 to 5 doses (puffs) from an MDI, for example 1 dose (1 puff), 2 dose (2 puffs), 3 doses (3 puffs), 4 doses (4 puffs) or 5 doses (5 puffs). The MDI, in one embodiment, is small and transportable by the patient. In another embodiment, administration is oral, nasal, subcutaneous or intravenous. In another embodiment, oral, nasal, intravenous, subcutaneous or inhalation administration of the effective amount of the prostacyclin compound or composition of the invention, for the treatment of interstitial lung disease (e.g., pulmonary fibrosis) or asthma, or a condition associated with interstitial lung disease or asthma, compared to oral, nasal, subcutaneous, intravenous at inhalation administration of treprostinil, results in a reduced severity of a systemic adverse events, or a decreased occurrence of a systemic adverse event.

In one embodiment, a method for treating an ischemic disease or condition, such as scleroderma, including systemic sclerosis, or Raynaud's Phenomenon in a patient in need of such treatment is provided. In a further embodiment, the method comprises administering an effective amount of one of the prostacyclin compounds or compositions provided herein, for example, a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or a deuterated version thereof, or a composition comprising a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or a composition comprising a deuterated compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), to the patient. Administration, in one embodiment, is via inhalation (e.g., with a nebulizer or metered dose inhaler), oral, nasal subcutaneous or intravenous administration. In another embodiment, oral, nasal, intravenous, subcutaneous or inhalation administration of an effective amount of the prostacyclin compound or composition of the invention, for the treatment of ischemic disease or condition, such as scleroderma, including systemic sclerosis, or Raynaud's Phenomenon, compared to oral, nasal, subcutaneous, intravenous or inhalation administration of treprostinil, results in a reduced severity of a systemic adverse events, or a decreased occurrence of a systemic adverse event.

The prostacyclin compounds or compositions provided herein, for example, a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or a deuterated version thereof, or a composition comprising a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or a composition comprising a deuterated compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), in one embodiment, are used for treating a patient for a digital ischemic lesion, such as a digital ulcer or a necrotic lesion, or for ameliorating a symptom or functional deficit and/or reducing the number of symptoms and/or functional deficit(s) associated with a digital ischemic lesion. The term "digital ischemic lesion" refers to a lesion on a digit, i.e., a toe or a finger, of a subject, such as a human being. In one embodiment, the digital ischemic lesion may be caused by or associated with an ischemic disease or condition, such as scleroderma, including systemic sclerosis, or Raynaud's Phenomenon. The symptom that may be ameliorated and/or reduced may be, for example, a pain associated with a digital ischemic ulcer and/or scleroderma. In some embodiments, administering a prostacyclin compound or composition provided herein, upon administration to a patient in need of treatment, provides amelioration or reduction of one or more functional deficits associated with a digital ischemic lesion. For example, in one embodiment, the prostacyclin compound or composition provided herein ameliorates or reduces a hand function deficit, i.e., provides an improvement in the hand function of the treated patient. Administration, in one embodiment, is via inhalation (e.g., with a nebulizer or metered dose inhaler), oral, nasal, subcutaneous or intravenous administration. In another embodiment, oral, nasal intravenous, subcutaneous or inhalation administration of an effective amount of the prostacyclin compound or composition of the invention, for the treatment of digital ischemic lesions, compared to oral, nasal subcutaneous, intravenous or inhalation administration of treprostinil, results in a reduced severity of a systemic adverse events, or a decreased occurrence of a systemic adverse event.

In one embodiment, a method for improving kidney function or treating symptoms associated with kidney malfunction or failure in a patient in need thereof is provided. In a further embodiment, the method comprises administering to a subject in need thereof an effective amount of a prostacyclin compound or composition provided herein, for example, a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or a deuterated version thereof, or a composition comprising a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or a composition comprising a deuterated compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), to the patient. Specific symptoms associated with reduced kidney functions include, for example, abnormally low urination, increased blood levels of creatinine and urea nitrogen, protein leakage in urine and/or pain. Administration, in one embodiment, is via inhalation (e.g., with a nebulizer or metered dose inhaler), oral, nasal, subcutaneous or intravenous administration. In another embodiment, oral, nasal, intravenous, subcutaneous or inhalation administration of an effective amount of the prostacyclin compound or composition of the invention, for improvement of kidney functions or amelioration of symptoms associated with kidney malfunction or failure, compared to oral, nasal, intravenous, subcutaneous or inhalation administration of treprostinil, results in a reduced severity of a systemic adverse events, or a decreased occurrence of a systemic adverse event.

In one embodiment, a method of treating a cardiovascular disease including congestive heart failure comprises is provided. The method, in one embodiment, comprises administering to a patient in need thereof, a prostacyclin compound or composition provided herein, for example, a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or a deuterated version thereof, or a composition comprising a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or a composition comprising a deuterated compound of Formula (I) (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III). Administration, in one embodiment, is via inhalation (e.g., with a nebulizer or metered dose inhaler), subcutaneous, oral, nasal or intravenous administration.

In one embodiment, a method for treating a peripheral vascular disease, including peripheral arterial occlusive disease and intermittent claudication is provided. In one embodiment, the method comprises administering to a patient in need thereof a prostacyclin compound or composition provided herein, for example, a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc), (IId), or (III), or a deuterated version thereof, or a composition comprising a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or a composition comprising a deuterated compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III). In addition to the prostacyclin compounds and compositions provided herein, other pharmacologically active substances may be present in the formulations of the present invention which are known to be useful for treating peripheral vascular disease. For example, the compounds of the invention may be present in combination with trental, a substance known to increase red blood cell deformability. Administration, in one embodiment, is via inhalation (e.g., with a nebulizer or metered dose inhaler), subcutaneous, oral, nasal or intravenous administration.

In one embodiment, a method for treating and/or preventing neuropathic diabetic foot ulcer is provided. In one embodiment, the method comprises administering to a patient in need thereof, a prostacyclin compound or composition provided herein, for example, a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or a deuterated version thereof, or a composition comprising a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or a composition comprising a deuterated compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III). Administration, in one embodiment, is via inhalation (e.g., with a nebulizer or metered dose inhaler), subcutaneous, oral, nasal or intravenous administration. In addition to the prostacyclin compounds and compositions provided herein, oilier pharmacologically active substances may be present in the formulations of the present invention which are known to be useful for treating and/or preventing foot ulcers in patients with diabetic neuropathy. For example, the compounds of the invention may be present in combination with analgesics to treat pain, dressing changes, vasodilator medications, and topical or oral antibiotics.

In one embodiment, admin titration of an effective amount of a prostacyclin compound or composition of the present invention for the treatment of the various diseases and indications described throughout, by inhalation, subcutaneous, oral, nasal or intravenous administration, results in a decreased number of side effects, or a reduced severity of one or more side effects (also referred to herein as "adverse events"), compared to the administration of an effective amount of treprostinil, when an effective amount of treprostinil is administered by inhalation, subcutaneous, oral, nasal or intravenous administration. For example, in one embodiment, a patient treated by the methods provided herein experiences a reduced severity and/or frequency in cough or a reduced cough response when administered a prostacylin compound or composition of the invention via inhalation (e.g., nebulization, dry powder inhaler, or via a metered dose inhaler), compared to the severity and/or frequency of cough or cough response elicited by inhalation administration of treprostinil to the patient.

In another embodiment, the prostacyclin compound administered to a patient in need of treatment provides a greater mean pulmonary Cmax and/or lower plasma $C_{max}$ of treprostinil for the patient, compared to the respective pulmonary or plasma $C_{max}$ of treprostinil, when treprostinil is administered to the patient. In a further embodiment, administration of the prostacyclin compound and treprostinil comprises intravenous administration.

In another embodiment, the prostacyclin compound administered to a patient in need of treatment provides a greater mean pulmonary or plasma area under the curve ($AUC_{0-t}$) of the prostacyclin compound or its treprostinil metabolite, compared to the mean pulmonary or plasma area under the curve ($AUC_{0-t}$) of treprostinil, when treprostinil is administered to the patient. In yet another embodiment, tire prostacyclin compound administered to a patient in need thereof provides a greater pulmonary or plasma time to peak concentration ($t_{max}$) of treprostinil, compared to the pulmonary or plasma time to peak concentration ($t_{max}$) of treprostinil, when treprostinil is administered to the patient.

In one embodiment, a prostacyclin compound or composition provided herein, for example, a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or deuterated version thereof, or a composition comprising a compound of Formula (I), (Ia), (Ib), (Ic), (Id), (Ia'), (Ib'), (Ic'), (Id'), (Ia"), (Ib"), (Ic"), (Id"), (II), (IIa), (IIb), (IIc) (IId), or (III), or a deuterated version thereof, is administered in combination with one or more additional active agents. In some embodiments, such one or more additional active agents can be also administered together with a prostacyclin compound or composition provided herein using a metered dose inhaler. In one embodiment, such one or more additional active agents can be administered separately, i.e., prior to, or subsequent to, the prostacyclin compound or composition provided herein. Particular additional active agents that can be administered in combination with treprotinil may depend on a particular disease or condition for treatment or prevention of which treprostinil is administered. In some cases, the additional active agent can be a cardiovascular agent such as a cox-2 inhibitor, a rho kinase inhibitor, a calcium channel blocker, a phosphodiesterase inhibitor, an endothelial antagonist, or an antiplatelet agent.

As provided above, the prostacyclin compounds and compositions of the present invention can be delivered to a patient in need thereof via an oral, nasal, pulmonary, intravenous or subcutaneous route. With respect to the pulmonary route, the prostacyclin compounds and compositions) of the present invention may be used in any dosage dispensing device adapted for such administration. The device, in one embodiment, is constructed to ascertain optimum metering accuracy and compatibility of its constructive elements, such as container, valve and actuator with the formulation and could be based on a mechanical pump system, e.g., that of a metered-dose nebulizer, dry powder inhaler, soft mist inhaler, or a nebulizer. For example, pulmonary delivery devices include a jet nebulizer, electronic nebulizer, a sort mist inhaler, and a capsule-based dry powder inhaler.

Suitable propellants, e.g., for MDI delivery, may be selected among such gases as fluorocarbons, chlorofluorocarbons (CFCs), hydrocarbons, hydrofluoroalkane propellants (e.g., HFA-134a and HFA-227), nitrogen and dinitrogen oxide or mixtures thereof.

The inhalation delivery device can be a nebulizer, dry powder inhaler, or a metered dose inhaler (MDI), or any other suitable inhalation delivery device known to one of ordinary skill in the art. The device can contain and be used to deliver a single dose of the prostacyclin composition or the device can contain and be used to deliver multi-doses of the composition of the present invention.

A nebulizer type inhalation delivery device can contain the compositions of the present invention as a solution, usually aqueous, or a suspension. For example, the prostacyclin compound or composition can be suspended in saline and loaded into the inhalation delivery device. In generating the nebulized spray of the compositions for inhalation, the nebulizer delivery device may be driven ultrasonically, by compressed air, by other gases, electronically or mechanically (e.g., vibrating mesh or aperture plate). Vibrating mesh nebulizers generate fine particle, low velocity aerosol, and nebulize therapeutic solutions and suspensions at a faster rate than conventional jet or ultrasonic nebulizers. Accordingly, the duration of treatment can be shortened with a vibrating mesh nebulizer, as compared to a jet or ultrasonic nebulizer. Vibrating mesh nebulizers amenable for use with the methods described herein include the Philips Respironics I-Neb®, the Omron MicroAir, the Nektar Aeroneb®, and the Pari eFlow®.

The nebulizer may be portable and hand held in design, and may be equipped with a self contained electrical unit. The nebulizer device may comprise a nozzle that has two coincident outlet channels of defined aperture size through which the liquid formulation can be accelerated. This results in impaction of the two streams and atomization of the formulation. The nebulizer may use a mechanical actuator to force the liquid formulation through a multiorifice nozzle of defined aperture size(s) to produce an aerosol of the formulation for inhalation. In the design of single dose nebulizers, blister packs containing single doses of the formulation may be employed.

In the present invention the nebulizer may be employed to ensure the sizing of particles is optimal for positioning of the particle within, for example, the pulmonary membrane.

Upon nebulization, the nebulized composition (also referred to as "aerosolized composition") is in the form of aerosolized particles. The aerosolized composition can be characterized by the particle size of the aerosol, for example, by measuring the "mass median aerodynamic diameter" or "fine particle fraction" associated with the aerosolized composition. "Mass median aerodynamic diameter" or "MMAD" is normalized regarding the aerodynamic separation of aqua aerosol droplets and is determined by impactor measurements, e.g., the Anderson Cascade Impactor (ACI) or the Next Generation Impactor (NGI). The gas flow rate, in one embodiment, is 28 Liter per minute for the ACI and 15 liter per minute for the NGI.

"Geometric standard deviation" or "GSD" is a measure of the spread of an aerodynamic particle size distribution. Low GSDs characterize a narrow droplet size distribution (homogeneously sized droplets), which is advantageous for targeting aerosol to the respiratory system. The average droplet size of the nebulized composition provided herein, in one embodiment is less than 5 µm or about 1 µm to about and has a GSD in a range of 1.0 to 2.2, or about 1.0 to about 2.2, or 1.5 to 2.2, or about 1.5 to about 2.2.

"Fine particle fraction" or "FPF," as used herein, refers to the fraction of the aerosol having a particle size less than 5 µm in diameter, as measured by cascade impaction. FPF is usually expressed as a percentage.

In one embodiment, the mass median aerodynamic diameter (MMAD) of the nebulized composition is about 1 µm to about 5 µm, or about 1 µm to about 4 µm, or about 1 µm to about 3 µm or about 1 µm to about 2 µm, as measured by the Anderson Cascade Impactor (ACI) or Next Generation Impactor (NGI). In another embodiment, the MMAD of the nebulized composition is about 5 µm or less, about 4 µm or less, about 3 µm or less, about 2 µm or less, or about 1 µm or less, as measured by cascade impaction, for example, by the ACI or NGI.

In one embodiment, the MMAD of the aerosol of the pharmaceutical composition is less than about 4.9 µm, less than about 4.5 µm, less than about 4.3 µm, less than about 4.2 µm, less than about 4.1 µm, less than about 4.0 µm or less than about 3.5 µm, as measured by cascade impaction.

In one embodiment, the MMAD of the aerosol of the pharmaceutical composition is about 1.0 µm to about 5.0 µm, about 2.0 µm to about 4.5 µm, about 2.5 µm to about 4.0 µm, about 3.0 µm to about 4.0 µm or about 3.5 µm to about 4.5 µm, as measured by cascade impaction (e.g., by the ACI or NGI).

In one embodiment, the FPF of the aerosolized composition is greater than or equal to about 50%, as measured by the ACI or NGI, greater than or equal to about 60%, as measured by the ACI or NGI or greater than or equal to about 70%, as measured by the ACI or NGI. In another embodiment, the FPF of the aerosolized composition is about 50% to about 80%, or about 50% to about 70% or about 50% to about 60%, as measured by the NGI or ACI.

In one embodiment, a metered dose inhalator (MDI) is employed as the inhalation delivery device for the compositions of the present invention. In a further embodiment, the prostacyclin compound is suspended in a propellant (e.g., hydroflourocarbon) prior to loading into the MDI. The basic structure of the MDI comprises a metering valve, an actuator and a container. A propellant is used to discharge the formulation from the device. The composition may consist of particles of a defined size suspended in the pressurized propellant(s) liquid, or the composition can be in a solution or suspension of pressurized liquid propellant(s). The propellants used are primarily atmospheric friendly hydroflourocarbons (HFCs) such as 134a and 227. The device of the inhalation system may deliver a single dose via, e.g., a blister pack, or it may be multi dose in design. The pressurized metered dose inhalator of the inhalation system can be breath actuated to deliver an accurate dose of the lipid-containing formulation. To insure accuracy of dosing, the delivery of the formulation may be programmed via a microprocessor to occur at a certain point in the inhalation cycle. The MDI may be portable and hand held.

In one embodiment, a dry powder inhaler (DPI) is employed as the inhalation delivery device for the compositions of the present invention. In one embodiment, the DPI generates particles having an MMAD of from about 1 µm to about 10 µm, or about 1 µm to about 9 µm, or about 1 µm to about 8 µm, or about 1 µm to about 7 µm, or about 1 µm to about 6 µm, or about 1 µm to about 5 µm, or about 1 µm to about 4 µm, or about 1 µm to about 3 µm, or about 1 µm to about 1 µm in diameter, as measured by the NGI or ACI. In another embodiment, the DPI generates a particles having an MMAD of from about 1 µm to about 10 µm, or about 2 µm to about 10 µm, or about 3 µm to about 10 µm, or about 4 µm to about 10 µm, or about 5 µm to about 10 µm, or about 6 µm to about 10 µm, or about 7 µm to about 10 µm, or about 8 µm to about 10 µm, or about 9 µm to about 10 µm, as measured by the NGI or ACI.

In one embodiment, the MMAD of the particles generated by the DPI is about 1 µm or less, about 9 µm or less, about 8 µm or less, about 7 µm or less, 6 µm or less, 5 µm or less, about 4 µm or less, about 3 µm or less, about 2 µm or less, or about 1 µm or less, as measured by the NGI or ACI.

In one embodiment, the MMAD of the particles generated by the DPI is less than about 9.9 µm, less than about 9.5 µm, less than about 0.3 µm, less than about 9.2 µm, less than about 9.1 µm, less than about 9.0 µm, less than about 8.5 µm, less than about 8.3 µm, less than about 8.2 µm, less than about 8.1 µm, less than about 8.0 µm, less than about 7.5 µm, less than about 7.3 µm, less than about 7.2 µm, less than about 7.1 µm, less than about 7.0 µm, less than about 6.5 µm, less than about 6.3 µm, less than about 6.2 µm, less than about 6.1 µm, less than about 6.0 µm, less than about 5.5 µm, less than about 5.3 µm, less than about 5.2 µm, less than about 5.1 µm, less than about 5.0 µm, less than about 4.5 µm, less than about 4.3 µm, less than about 4.2 µm, less than about 4.1 µm, less than about 4.0 µm or less than about 3.5 µm, as measured by the NGI or ACI.

In one embodiment, the MMAD of the particles generated by the DPI is about 1.0 urn to about 10.0 µm, about 2.0 µm to about 9.5 µm, about 2.5 µm to about 9.0 µm, about 3.0 µm to about 9.0 µm, about 3.5 µm to about 8.5 µm of about 4.0 µm to about 8.0 µm.

In one embodiment, the FPF of the prostacyclin particulate composition generated by the DPI is greater than or equal to about 40% as measured by the ACI or NGI, greater than or equal to about 50%, as measured by the ACI or NGI, greater than or equal to about 60%, as measured by the ACI or NGI, or greater than or equal to about 70%, as measured by the ACI or NGI. In another embodiment, the FPF of the aerosolized composition is about 40% to about 70% or about 50% to about 70% or about 40% to about 60%, as measured by the NGI or ACI.

EXAMPLES

The present invention is further illustrated by reference to the following Examples. However, it should be noted that these Examples, like the embodiments described above, are illustrative and are not to be construed as restricting the scope of the invention in any way.

Example 1—Synthesis of Treprostinil Alkyl Esters

Treprostinil compounds derivatized with alkyl groups at the carboxylic acid moiety were prepared. Specifically, treprostinil was derivatized at the carboxylic acid moiety with $C_2$, $C_3$, $C_4$, $C_5$, $C_6$, $C_8$, $C_{10}$, $C_{12}$, $C_{16}$, and $C_{18}$ alkyl chains (i.e., $R_2$ in Formula (A), below, is $C_2$, $C_3$, $C_4$, $C_5$, $C_6$, $C_8$, $C_{10}$, $C_{12}$, $C_{16}$ or $C_{18}$ alkyl) to make treprostinil alkyl esters of various ester chain lengths. Treprostinil can be synthesized, for example, by the methods disclosed in U.S. Pat. Nos. 6,765,117 and 8,497,393. Synthesis of prostaglandin derivatives is described in U.S. Pat. No. 4,668,814. The disclosures of U.S. Pat. Nos. 6,765,117, 8,497,393 and 4,668,814 are each incorporated by reference in their entireties for all purposes.

Scheme 1:

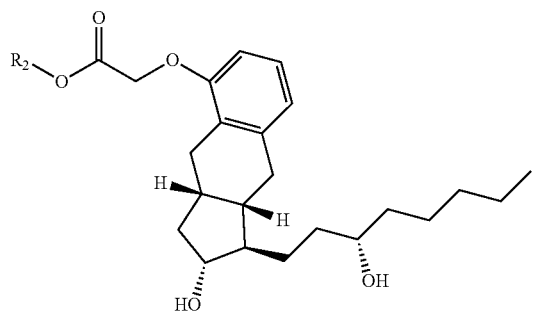

Formula (A)

Treprostinil esterification was catalyzed by strongly acidic resin Amberlyst® 15 (Rohm and Haas). Treprostinil acid was dissolved in anhydrous dioxane/alcohol at a concentration 10 mg/mL (typically 4 mL). Alcohol ($R_2$—OH) added was appropriate to make corresponding chain length at the $R_2$ group. By way of example, for the $C_2$ (ethyl ester) compound, the alcohol was ethanol. The molar amount of alcohol in the solvent was ten times the molar amount of treprostinil.

Treprostinil in dioxane/alcohol solution was added to washed and dry Amberlyst resin. Per each 40 mg treprostinil, 1 g resin in a glass vial was added. The mixture was placed on a shaker and incubated overnight at 40° C. Next, the liquid portion was taken out of the vial, washed twice with 3 mL dioxane. All recovered solvent was then collected. The solvent was dried by nitrogen stream until the evaporation stopped. The remaining treprostinil alkyl ester and nonvolatile alcohol (if long chain alcohol used) was dissolved in 2 mL hexane/ethyl acetate 1:1, and cleaned by liquid-liquid extraction vs. equal volume of phosphate buffer, and then water. Next, the organic layer was separated and dried by nitrogen stream and further in vacuum. If a long chain alcohol used, an additional purification step was required to separate alcohol by liquid chromatography, ACE CN, 5 μm, Ultra-Inert HPLC Column, 100×21.2 mm was used, with mobile phase of hexane/propanol 98.2%.

Scheme 2:

To a rotation of (1R,2R,3aS,9aS)-[[2,3,3a,4,9,9a-hexahydro-2-hydroxy-1-[(3S)-3-hydroxyoctyl]-1H-benz[f]inden-5-yl]oxy]acetic acid (treprostinil) (78.1 mg, 200 μmoles) dissolved in 1,4-dioxane (2.0 mL) was added Amberlyst® 15 resin (2.0 g) and alcohol $R_2$—OH (2.0 mmoles, 10 equivalents). The reaction mixture was heated to 40° C. and allowed to shake at approximately 100 rpm for 18-196 hours. Solvent was removed and the resin was washed with acetonitrile (MeCN) (3×3 mL). The 1,4-dioxane and MeCN extracts were combined and dried using a gentle stream of warmed $N_2$ gas and gentle heat to yield a thick waxy solid. The crude material was dissolved in 20% "PrOH/Hexanes and admitted to preparatory HPLC purification. Solvent was removed from the purified material using a gentle stream of warmed $N_2$ gas and gentle heat to yield an off-white waxy solid. The pure material was suspended in ethyl lactate for storage and was submitted to analytical HPLC for concentration determination.

By way of example, the following compounds of Formula (A) were synthesized by the method of scheme 2.

| $R_2$ group | | Compound abbreviation |
|---|---|---|
| $R_2$ = ~~~~~~~~~~~~~~~~ ($C_{16}$) | | $C_{16}$-TR |
| $R_2$ = ~~~~~~~~~~~~~~ ($C_{14}$) | | $C_{14}$-TR |
| $R_2$ = ~~~~~~~~~~~~ ($C_{12}$) | | $C_{12}$-TR |
| $R_2$ = ~~~~~~~~~~ ($C_{10}$) | | $C_{10}$-TR |
| $R_2$ = ~~~~~~~~~ (2$C_9$) | | $C_9$-TR |
| $R_2$ = ~~~~~~~ (5$C_9$) | | 5$C_9$-TR |
| $R_2$ = ~~~~~~~~~ ($C_9$) | | 2$C_9$-TR |

| R₂ group | Compound abbreviation |
|---|---|
| R₂ = 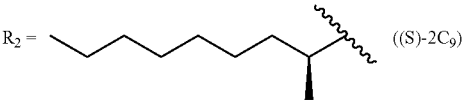 ((S)-2C₉) | (S)-2C₉-TR |
| R₂ = 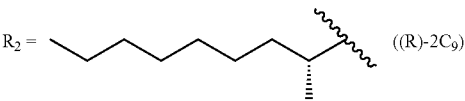 ((R)-2C₉) | (R)-2C₉-TR |
| R₂ = 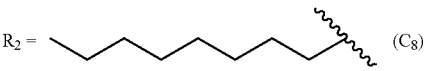 (C₈) | C₈-TR |
| R₂ = 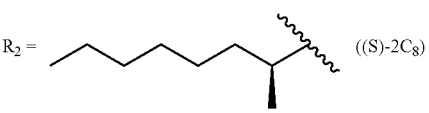 ((S)-2C₈) | (S)-2C₈-TR |
| R₂ = 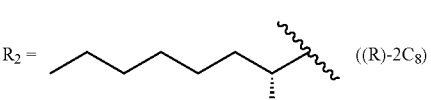 ((R)-2C₈) | (R)-2C₈-TR |
| R₂ = 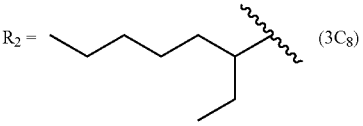 (3C₈) | 3C₈-TR |
| R₂ = 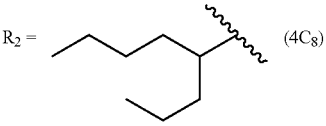 (4C₈) | 4C₈-TR |
| R₂ = 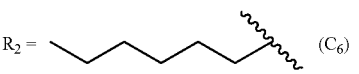 (C₆) | C₆-TR |
| R₂ = 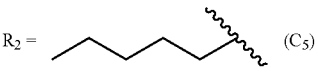 (C₅) | C₅-TR |
| R₂ = 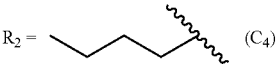 (C₄) | C₄-TR |
| R₂ = 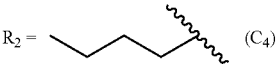 (C₃) | C₃-TR |
| R₂ = 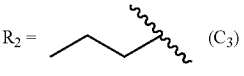 (C₂) | C₂-TR |

A general diagram for synthesis of the ethyl ester of treprostinil is shown in Scheme 1, below. The alcohol can be modified based on the desired alkyl ester chain length (e.g., $C_5$-$C_{18}$ alkyl esters of even or odd chain length, straight chain or branched).

Scheme 1: Esterification Mechanism for alkyl ester-TR Compounds

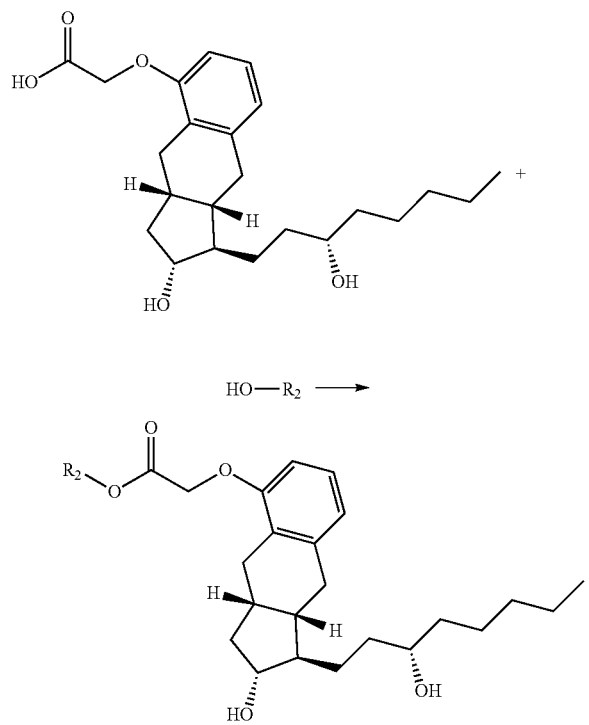

Example 2—Spontaneous and Esterase-Mediated Hydrolysis of Treprostinil Alkyl Esters Spontaneous and/or esterase-mediated hydrolysis was measured for the prostacyclin alkyl ester compositions provided in Table 2. Cx indicates the alkyl chain length at position $R_2$ of the compound of Formula (A), provided above Additionally, spontaneous hydrolysis was measured for 200 μM of treprostinil compounds derivatized at the carboxylic acid group with either a $C_3$, $C_4$, $C_5$, $C_6$, $C_8$ or $C_{10}$ alkyl group in 20% ethanol at 40° C. at six time points (0 hr., 1 hr., 2 hr., 4 hr., 6 hr., 24 hr.).

Each sample was prepared as a 200 μM solution in 20% ethanol. At each time point, an aliquot was removed for HPLC analysis to resolve remaining reactants ($C_3$, $C_4$, $C_5$, $C_6$, $C_8$, $C_{10}$) or their degradation product (treprostinil). For each sample, hydrolysis was calculated from the measured reactant and product peak areas:

% hydrolysis=(product peak area/(reactant peak area+product peak area)*100).

Figure 1A:
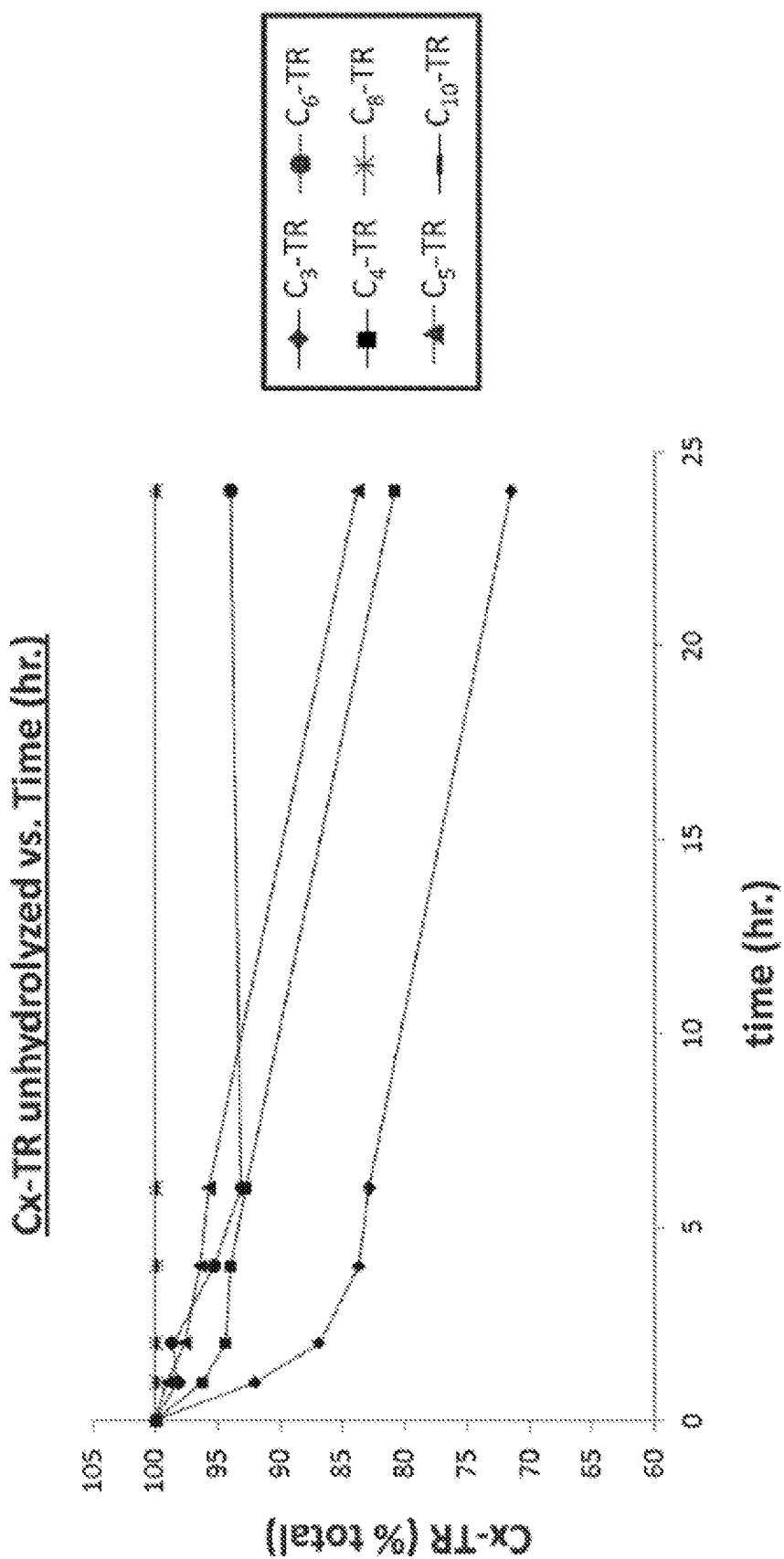
FIG. 1A is a graph showing the spontaneous hydrolysis of treprostinil compounds vs. time. (C3: propyl ester, C4: butyl ester, C5: pentyl ester, C6: hexyl ester, C8: octyl ester and C10: decyl ester).

The results of the time course experiment are provided at FIG. 1A. The results indicate that hydrolysis rate is correlated with the length of the alkyl ester moiety.

Esterase mediated hydrolysis of treprostinil compounds and compositions was measured for compounds derivatized at the carboxylic acid group with $C_3$, $C_4$, $C_6$, $C_8$ and $C_{10}$ alkyl groups and compositions comprising the same. Experiments were conducted at 37° C., and hydrolysis was measured at 15 min., 30 min., and 1 hour after addition of the esterase to the compound solution. The reaction mixture for each sample was prepared at a final volume of 500 μL containing, 200 μM treprostinil compound, 0.05 U esterase, 20% ethanol, and PBS. Hydrolysis was measured as described above.

Figure 1B:
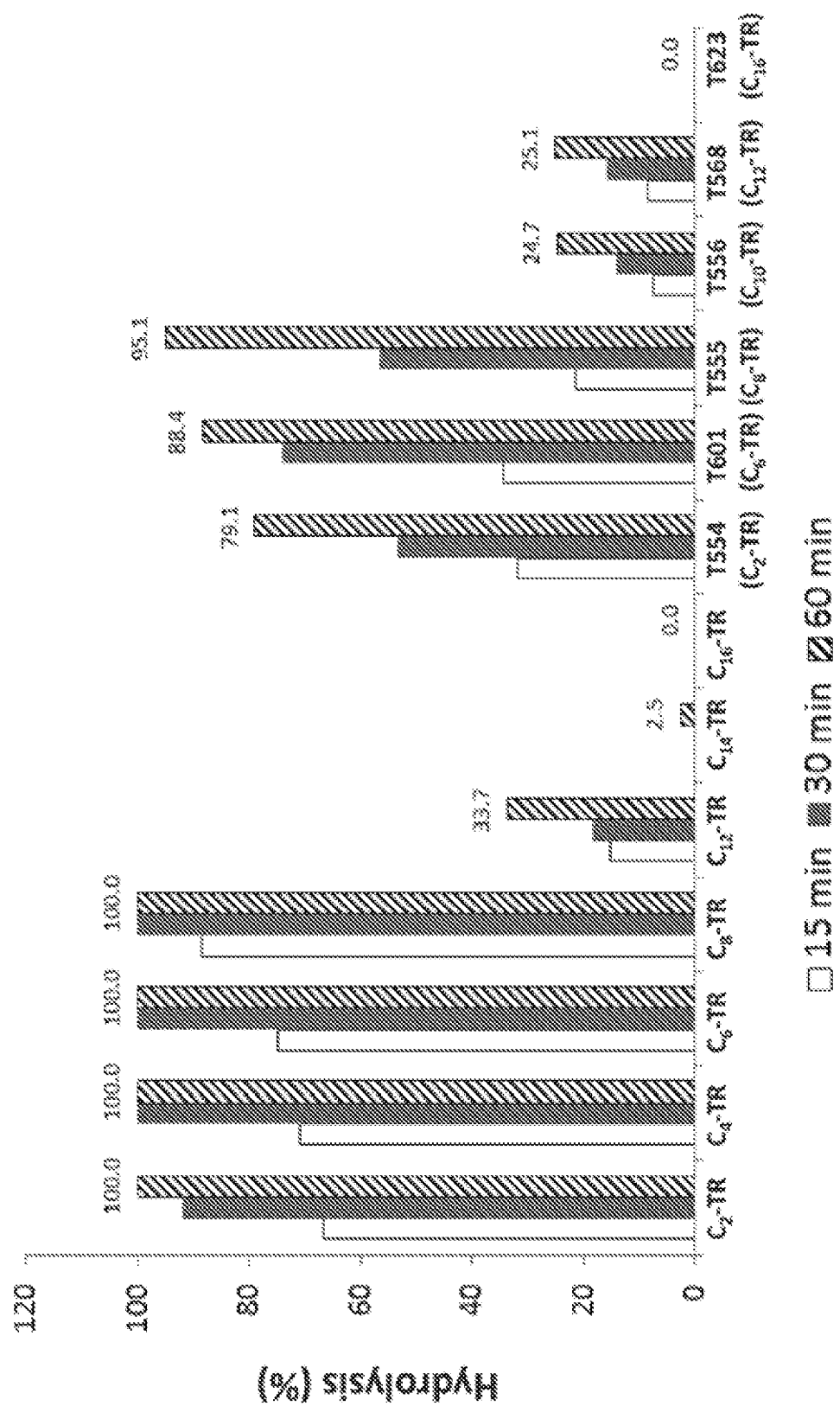
FIG. 1B is a graph showing esterase-mediated hydrolysis of the alkyl chains at various timepoints (15 min., 50 min., 60 min.) of treprostinil compounds dissolved in aqueous buffer, and treprostinil compositions comprising PEGylated lipids.

The results of this experiment are provided at FIG. 1B. The results indicate that compound degradation rate decreases with increasing alkyl ester chain length.

Treprostinil alkyl ester conversion to treprostinil was also measured in the presence of rat, dog and monkey lung tissue homogenate at 37° C. Here, data were calculated based on fit of exponential increase to the maximum (experiments performed in duplicate). The results of this study are provided below in Table 2A and FIG. 37. Specifically, FIG. 37 left, shows that conversion to treprostinil depends on alkyl chain length. In this experiment, treprostinil alkyl esters were incubated for 4 hours at a final concentration of 200

TABLE 2

Components of prostacyclin alkyl ester compositions

| Composition | Cx-TR | Hydrophobic Additive | PEGylated lipid | Cx-TR mol % | Hydrophobic Additive mol % | PEG-lipid mol % | DOPC mol % |
|---|---|---|---|---|---|---|---|
| T493 | $C_2$-TR | Squalene | Chol-PEG2K | 40 | 40 | 20 | 0 |
| T500 | $C_4$-TR | Squalene | Chol-PEG2K | 40 | 40 | 20 | 0 |
| T507 | $C_6$-TR | Squalene | Chol-PEG2K | 40 | 40 | 20 | 0 |
| T508 | $C_8$-TR | Squalene | Chol-PEG2K | 40 | 40 | 20 | 0 |
| T509 | $C_{10}$-TR | Squalene | Chol-PEG2K | 40 | 40 | 20 | 0 |
| T554 | $C_2$-TR | Squalene | Chol-PEG2K | 40 | 40 | 10 | 10 |
| T555 | $C_8$-TR | Squalene | Chol-PEG2K | 40 | 40 | 10 | 10 |
| T556 | $C_{10}$-TR | Squalene | Chol-PEG2K | 40 | 40 | 10 | 10 |
| T568 | $C_{12}$-TR | Squalene | Chol-PEG2K | 40 | 40 | 10 | 10 |
| T623 | $C_{16}$-TR | Squalene | Chol-PEG2K | 40 | 40 | 10 | 10 |
| T637 | $C_{18}$-TR | Squalene | Chol-PEG2K | 40 | 40 | 10 | 10 | nM in 1 mL of tissue homogenate prepared in water and normalized to 10 mg/mL of protein.

FIG. 37 right, shows conversion of $C_{12}$-TR to treprostinil (percentage) in the presence of rat, dog or monkey lung tissue homogenate $C_{12}$-TR was incubated for 4 hours at a final concentration of 200 nM in 1 mL of tissue homogenate prepared in water and normalized to 10 mg/mL of protein. Both FIG. 37 experiments (left and right graphs) were performed in duplicate and the lines represent nonlinear exponential regression assuming 1 phase decay.

TABLE 2A

Rate of treprostinil alkyl ester conversion in the presence of rat, dog or monkey lung tissue homeogenate.

| Rate of treprostinil alkyl ester conversion (nmOL/h * g of protein) | $C_8$-TR | $C_{10}$-TR | $C_{12}$-TR | $C_{14}$-TR |
|---|---|---|---|---|
| Rat | 32.5 | 7.3 | 1.1 | 0.4 |
| Dog | 49.8 | 10.5 | 2.2 | — |
| Monkey | 17.3 | 4.6 | 0.6 | — |

Example 3—Particle Size Characterization of Treprostinil Compositions

The compositions in Table 3 were subject to particle size characterization. Cx indicates the alkyl chain length at position $R_2$ of Formula (A), provided above.

TABLE 3

Compositions subject to particle size characterization

| Composition | Cx-TR | Hydrophobic Additive | PEGylated lipid | Cx-TR mol % | Hydrophobic Additive mol % | PEGylated lipid mol % | DOPC mol % |
|---|---|---|---|---|---|---|---|
| T554 ($C_2$) | $C_2$-TR | Squalene | Chol-PEG2K | 40 | 40 | 10 | 10 |
| T499 ($C_3$) | $C_3$-TR | Squalene | Chol-PEG2K | 40 | 40 | 20 | 0 |
| T500 ($C_4$) | $C_4$-TR | Squalene | Chol-PEG2K | 40 | 40 | 20 | 0 |
| T501 ($C_5$) | $C_5$-TR | Squalene | Chol-PEG2K | 40 | 40 | 20 | 0 |
| T601 ($C_6$) | $C_6$-TR | Squalene | Chol-PEG2K | 40 | 40 | 10 | 10 |
| T555 ($C_8$) | $C_8$-TR | Squalene | Chol-PEG2K | 40 | 40 | 10 | 10 |
| T556 ($C_{10}$) | $C_{10}$-TR | Squalene | Chol-PEG2K | 40 | 40 | 10 | 10 |
| T568 ($C_{12}$) | $C_{12}$-TR | Squalene | Chol-PEG2K | 40 | 40 | 10 | 10 |
| T623 ($C_{16}$) | $C_{16}$-TR | Squalene | Chol-PEG2K | 40 | 40 | 10 | 10 |
| T637 ($C_{18}$) | $C_{18}$-TR | Squalene | Chol-PEG2K | 40 | 40 | 10 | 10 |

All particle size measurements were performed using a Wyatt Technology Mobius™ Zeta Potential/Particle Sizing Instrument in Quasi-elastic light scattering (QELS) mode. Composition aliquots were diluted 10-fold in pre-filtered (0.02 μm pore filter) ultrapure of deionized $H_2O$. Light scattering data was collected and converted into particle size and size distribution using Dynamics® v. 7.2.4 instrument software. Reported average particle size diameter is based on the cumulants model, which mathematically fits particle diffusion constants (determined by the raw scattering intensities of particles in a suspension) to obtain the particle size mean and a distribution of particle sizes around the mean diameter.

Figure 2:
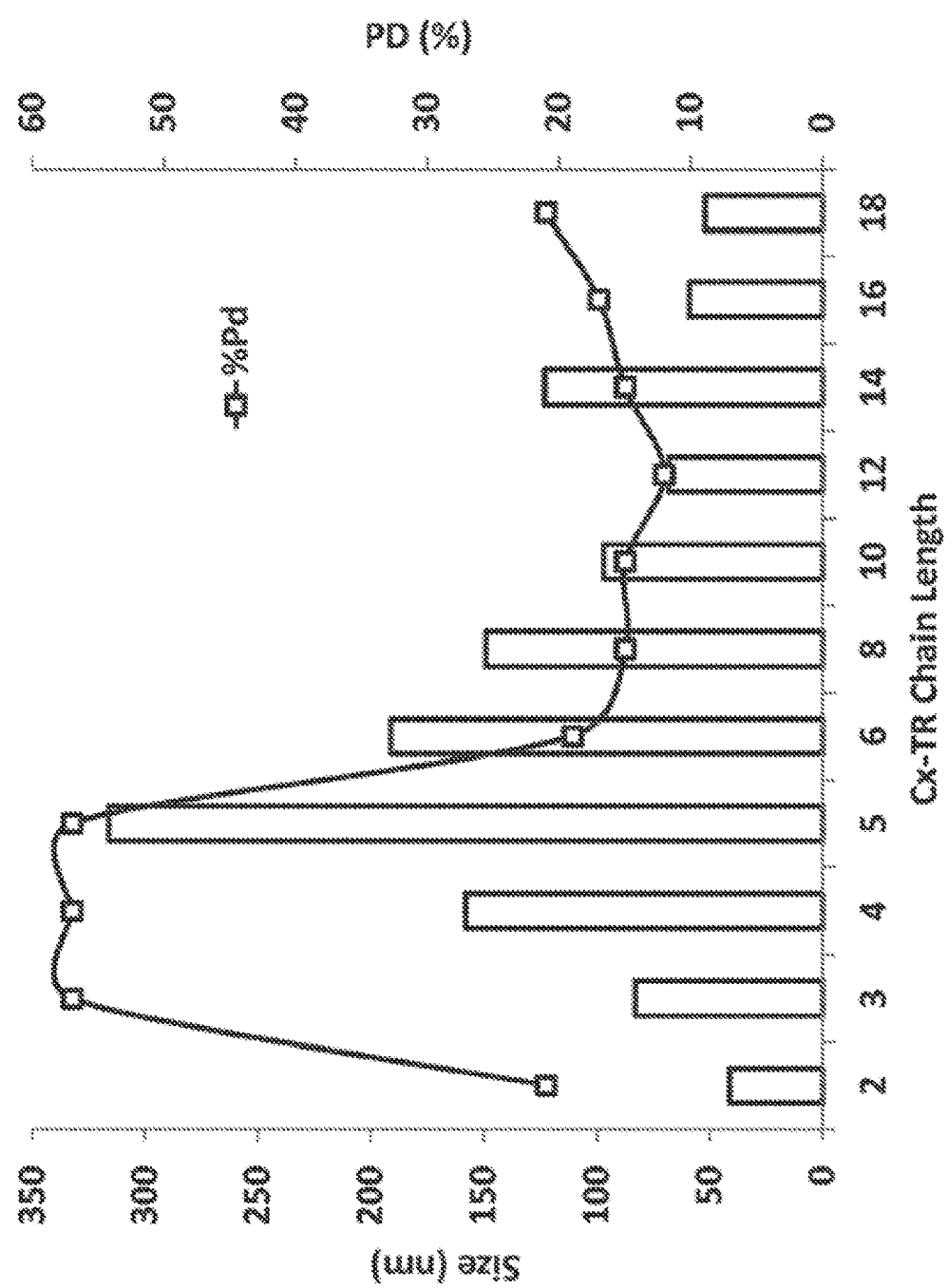
FIG. 2 is a graph of the average particle diameter for various treprostinil alkyl esters in formulations comprising PEGylated lipids as a function of alkyl ester chain length. The alkyl chain is present at the carboxylic acid moiety of treprostinil. PD is polydispersity.

It was found that the particle size (average particle diameter) of treprostinil compositions increases in size in compositions comprising $C_2$-$C_5$ alkyl ester derivatized treprostinil, and decreases in size in compositions comprising $C_6$-$C_{12}$ alkyl ester derivatized treprostinil. These results are provided in FIG. 2. The largest average particle diameter was found for compositions comprising treprostinil pentyl ester (i.e., treprostinil derivatized with a $C_5$ alkyl ester) (316 nm). Compositions comprising treprostinil ethyl ester had an average particle diameter of 41 nm. It should be recognized that through manipulation of processing parameters the same compositions could be produced with different mean diameters and size distributions. Manipulations of composition in combination with manipulation of processing parameters could also be performed to produce particles of various sizes.

Under the conditions utilized here it was also found that longer chain derivatized treprostinil compounds formed more uniform particles than compounds having shorter alkyl ester chains. Particle uniformity was determined using the software-calculated polydispersity (% PD). Polydispersity is defined as the standard deviation of the particle size distribution from the mean particle size value. % PD normalizes the polydispersity to the mean diameter by dividing by the mean size and multiplying by 100. These parameters indicate whether a particle suspension has one or more size populations of particles (monomodal versus multimodal). It also gives insight into the width of particle size distribution (or degree particle uniformity) around the mean for the respective particle populations.

Dynamics® polydispersity parameter represents a monodisperse population of particles if % PD≤15. A calculated % PD≥57% represents a polydisperse population of particles. For instance, the % PD data plotted in FIG. 2 yields information about the uniformity of particle size populations from the treprostinil compounds tested $C_8$-TR (TR=treprostinil), $C_{10}$-TR, $C_{12}$-TR, and $C_{14}$-TR alkyl esters yielded near monodisperse particles with % PD at or around 15. $C_2$-TR, $C_6$-TR, $C_{16}$-TR, and $C_{18}$-TR alkyl esters yielded particles that have % PD slightly above the 15, suggesting that there is one population of particles. However, these particles possessed a wider distribution of particles sizes around the mean particle size when compared to $C_8$-TR, $C_{10}$-TR, $C_{12}$-TR, and $C_{14}$-TR. $C_3$-TR, $C_4$-TR, and $C_5$-TR showed much greater than 15% PD and some ≥57. These values indicate that there are multiple populations of particles that possess wide particle size distributions.

Example 4—Measurement of Cyclic Adenosine Monophosphate (cAMP) Levels in CHO-K1 Cells in Response to Treprostinil Compositions A cell based Chinese hamster ovary-K1 (CHO-K1) assay based on the GloSensor™ cAMP assay (Promega) was used to characterize the effect of treprostinil alkyl ester compounds on cAMP levels.

cAMP is a second messenger involved in signal transduction of G-protein coupled receptors (GPCRs) acting through Gα-s and Gα-i proteins. Because the treprostinil receptor is a GPCR, the assay provides an indication of whether the respective prostacyclin compound (or metabolite thereof) binds its receptor and activates the GPCR cell signaling cascade.

The GloSensor™ assay harnesses a genetically modified form of firefly luciferase into which a cAMP-binding protein moiety has been inserted. Upon binding of cAMP, a conformational change is induced leading to increased light output.

The EP2 prostanoid receptor was co-transfected with the GloSensor™ plasmid (Promega) into CHO-K1 cells as follows. CHO-K1 cells were harvested when the monolayer was at 50-90% confluence. First, cells were washed with 5 mL PBS. Two mL of pre-warmed (37° C.) 0.05% trypsin-EDTA (Life Technologies, Cat #: 25300054) was added, and cells were dislodged by tapping the flask on the side. Next, 10 mL of antibiotic free growth media (Life Tech, Cat #: 31765092) containing 10% fetal bovine serum (FBS; Hyclone, Cat #: SH30071.03) was added, and cells were centrifuged at 250×g for 5 minutes at room temperature. The media was aspirated, and the cell pellet was resuspended in 10 mL of growth media. Cell number was determined using a hemacytometer. Each well of a culture treated 96 well flat bottom plate (Costar, Cat #: 3917) was seeded with $1 \times 10^4$ cells per 100 μL antibiotic-free growth media. The cells were incubated overnight at 37° C. and 5% $CO_2$ in a water-jacketed incubator.

For small scale transfections of up to 20 wells, the pGLoSensor-22F cAMP plasmid (Promega, Cat #: E2301) (2 μg): (EP2) (10 ng) (Origene, Cat #: SC126559): pGEM-3Zf(+) (10 ng) (Promega, Cat #: P2271) ratio was diluted to a final concentration of 12.6 ng/μL (total plasmid) in Opti-MEM I reduced-serum medium (Life Technologies, Cat #: 1985062). Next, 6 μL of FuGENE HD transfection reagent (Promega, Cat #: E2311) was added to 160 μL of diluted plasmid and mixed carefully by gentle pipetting. The complex was incubated at room temperature for 0 to 10 minutes, and then 8 μL of the complex was added per well of a 96 well white assay plate (Costar, Cat : 3917) and gently mixed without disturbing the cell monolayer. The plates were incubated for 20-24 hours at 31° C. and 5% $CO_2$ in a water-jacketed incubator. Following incubation, cells were treated and analyzed.

For larger scale transfections, the aforementioned steps were scaled up accordingly, and cells were frozen following the last incubation. In order to prepare frown transfected CHO-K1 cells, the media was aspirated from failure flasks and cells were rinsed with 5 mL PBS. As above, 2 mL of pre-warmed (37° C.) 0.05% trypsin-EDTA (Life Technologies, Cat #: 25300054) was added, and cells were dislodged by tapping the flask on the side. Next, 10 mL of antibiotic free growth media (Life Technologies, Cat #: 31765092) containing 10% FBS (Hyclone, Cat #: SH30071.03) was added, and cells were centrifuged at 250×g for 5 minutes at room temperature. Cell number was determined using a hemacytometer. The media was aspirated, and the cell pellet was resuspended in freezing media (Millipore, cat #: S-002-5F) at $2.5 \times 10^6$ cells/vial. Transfected cells were incubated overnight at −80° C. before transfer to liquid nitrogen for long term storage. The frozen stocks were then thawed one day prior to use for assays, and cells were seeded at $2.5 \times 10^4$ cells per well in 100 μL of antibiotic-free complete media (F12 (Life Technologies, Cat #: 31765092)+10% FBS (Hyclone, Cat #: SH30071.03)). Following an overnight incubation at 37° C. and 5% $CO_2$ in a water-jacketed incubator, the cells were ready for use in cAMP response assays.

In preparation for cAMP measurement, the cells were equilibrated with the GloSensor cAMP reagent prior to treatment. For equilibration, the medium was carefully removed from the individual well. Next, 100 μL of equilibration medium (6% v/v of Glosensor Reagent stock solution (Promega, Cat #: E291), 10% FBS (Hyclone, Cat #: SH30071.03) and 88% $CO_2$ independent medium (Life Technologies, Cat #: 18045088)) was added per well of the 96-well plate, and added to the side of each well. The plate was then incubated for 2 hours at room temperature. A first pre-read measurement was taken using a microplate reader (MicroLumat Plus). Plates were incubated for an additional 10 minutes at room temperature, followed by a second pre-read measurement.

Working solutions of free treprostinil and treprostinil alkyl ester compounds were prepared at 10× concentration so that the final concentration was 1× once added to the cells. Following treatment, each plate was read every 5 minutes for the duration of the assay using a microplate reader (MicroLumat Plus). In order to determine the fold change in cAMP relative to she control the transfection efficiency was first determined by dividing the second pre-read measurement by the average of the corresponding pre-read measurements. Next, the normalized relative light units (RLUs) of the samples were determined by dividing the plate read measurement by the transfection efficiency. The fold change in cAMP relative to the control was then determined by dividing the normalized RLU of the samples by the normalized RLU of the control.

Validation of cAMP Assay Using Free Treprostinil

The cAMP assay was validated using free treprostinil. Treprostinil (10 μM, 1 μM, 0.1 μM, 0.01 μM, 0.001 μM, 0.0001 μM, 0.00001 μM, and 0.000001 μM) was added to equilibrated CHO-K1 cells, and the cells were then incubated for 30 minutes. Luminescence was then measured at room temperature.

Alkyl Ester Treprostinil Compositions

CHO-K1 cells co-transfected with the EP2 receptor and GloSensor™ plasmid were challenged with free treprostinil (10 μM, 1 μM, 0.1 μM, 0.01 μM, 0.001 μM, 0.0001 μM, 0.00001 μM, 0.000001 μM) and treprostinil alkyl ester compounds, i.e., compounds having either a $C_6$, $C_8$ or $C_{10}$ straight chain alkyl group at the $R_2$ position of the compound of Formula (A), shown above.

Figure 3A:
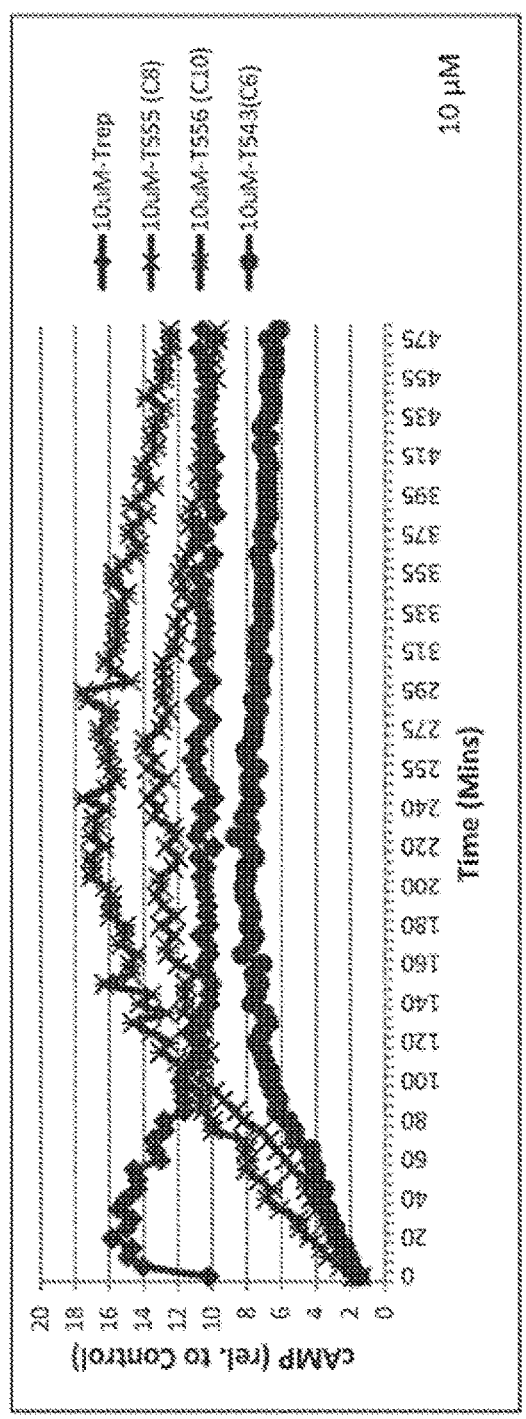
FIGS. 3A, 3B and 3C are graphs of relative cAMP response of CHO-K1-P4 cells ($2.5 \times 10^4$ cells/well) vs. time, in response to 10 µM (FIG. 3A), 1 µM (FIG. 3B) or 0.1 µM (FIG. 3C) treprostinil and treprostinil alkyl ester compositions. (C6: hexyl ester, C8: octyl ester, C10: decyl ester).
Figure 3B:
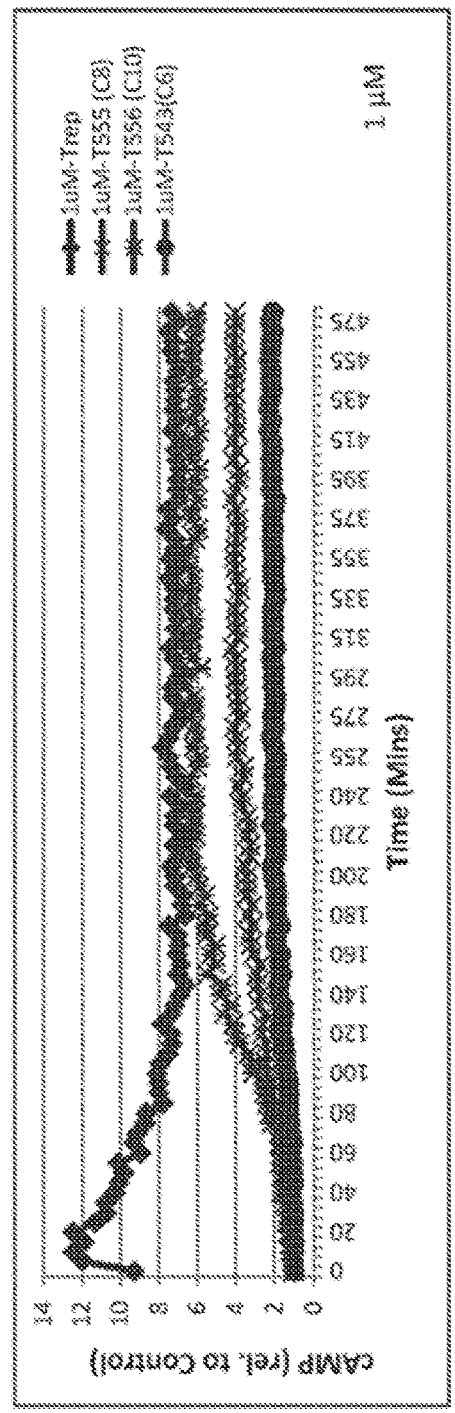
Figure 3C:
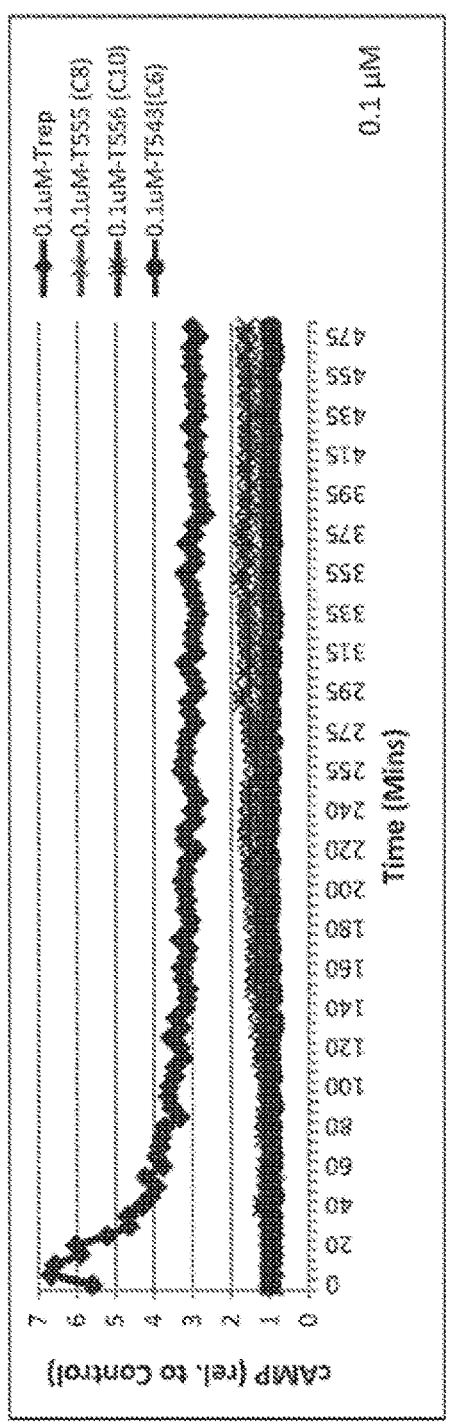

The following concentrations of compounds were measured: 10 μM, 1 μM, 0.1 μM, 0.01 μM, 0.001 μM, 0.0001 μM, 0.00001 μM, 0.000001 μM cAMP levels were then measured every 5 minutes over a time course of 8 hours. Results from the three highest concentrations are provided at FIG. 3A (10 µM), FIG. 3B (1 µM) and FIG. 3C (0.1 µM). The components of the treprostinil compositions set forth in FIGS. 3A, 3B and 3C are shown in Table 4 below.

cAMP levels in response to the treprostinil decyl ester ($C_{10}$-TR) (10 µM) were equivalent to free treprostinil and the levels were sustained for at least 6 hours. The sustained cAMP level was not exhibited in response to free treprostinil.

CHO-K1 cells co-transfected with the EP2 receptor and GloSensor™ plasmid were challenged with free treprostinil (5 µM) and treprostinil compositions having either a treprostinil derivatized at the $R_2$ position of the above compound with a $C_2$, $C_6$, $C_8$, $C_{10}$, or $C_{12}$ straight chain group (5 µM). The components of the treprostinil compositions are provided in Table 5, below. cAMP levels were then measured every 5 minutes over a time course of 8 hours.

Figure 4:
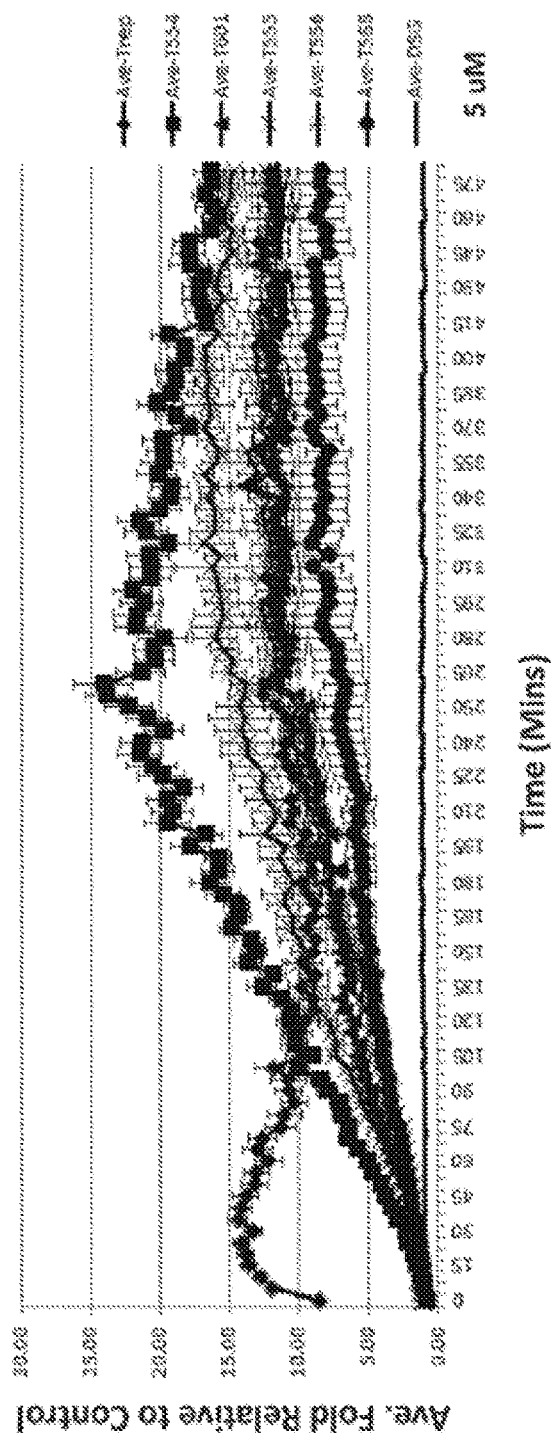
FIG. 4 is a graph of relative cAMP response of CHO-K1-P4 cells ($2.5 \times 10^4$ cells/well) vs. time, in response to 5 µM treprostinil and treprostinil alkyl ester compositions. (C6: hexyl ester, C8: octyl ester, C10: decyl ester, C12: dodecyl ester).
Figures 5, 6:
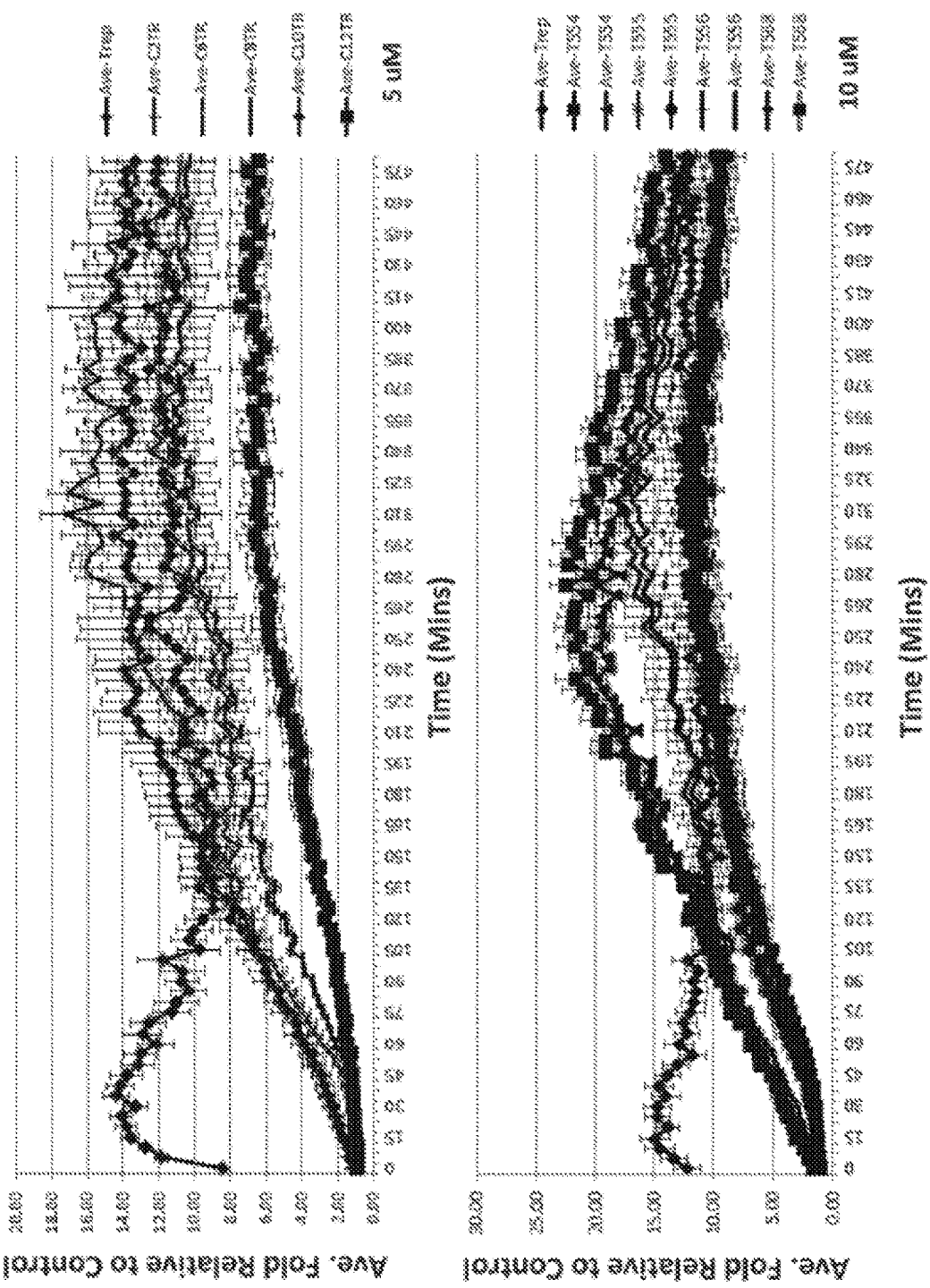
FIG. 5 is a graph of relative cAMP response of CHO-K1-P4 cells ($2.5 \times 10^4$ cells/well) vs time, in response to challenge with treprostinil and various treprostinil alkyl ester compounds at 5 µM.
FIG. 6 is graph of relative cAMP activity of CHO-K1-P4 cells ($2.5 \times 10^4$ cells/well) vs. time, in response to challenge with treprostinil and nebulized and non-nebulized treprostinil alkyl ester compositions, as measured by a modified GloSensor assay. "(N)" indicates nebulized compositions.
Figure 7:
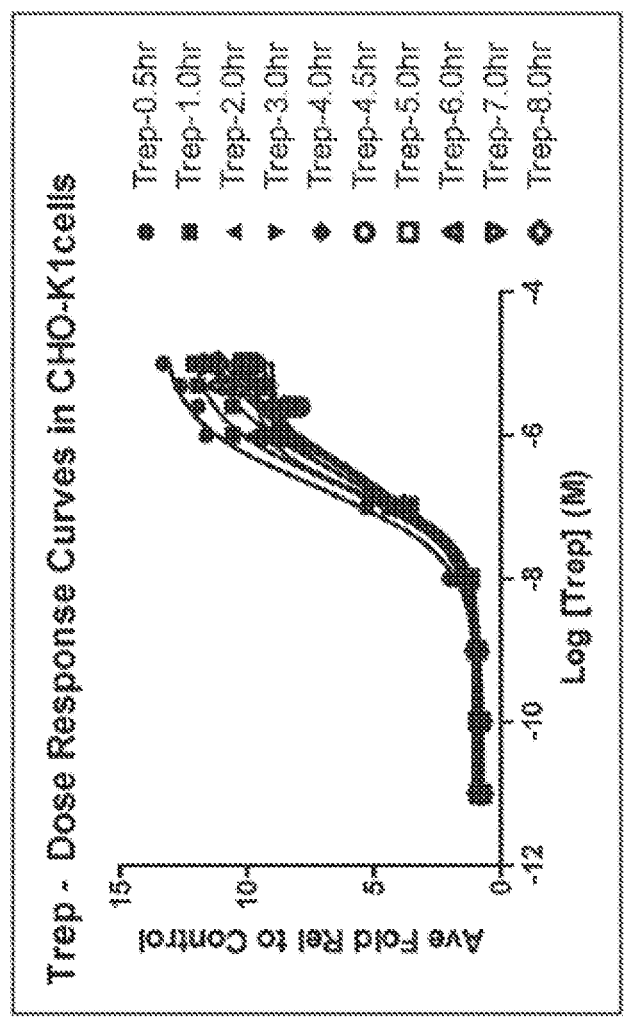
FIG. 7 is a graph of relative cAMP response of CHO-K1-P4 cells ($2.5 \times 10^4$ cells/well) vs. free treprostinil, at various dosages and time points.
Figure 8:
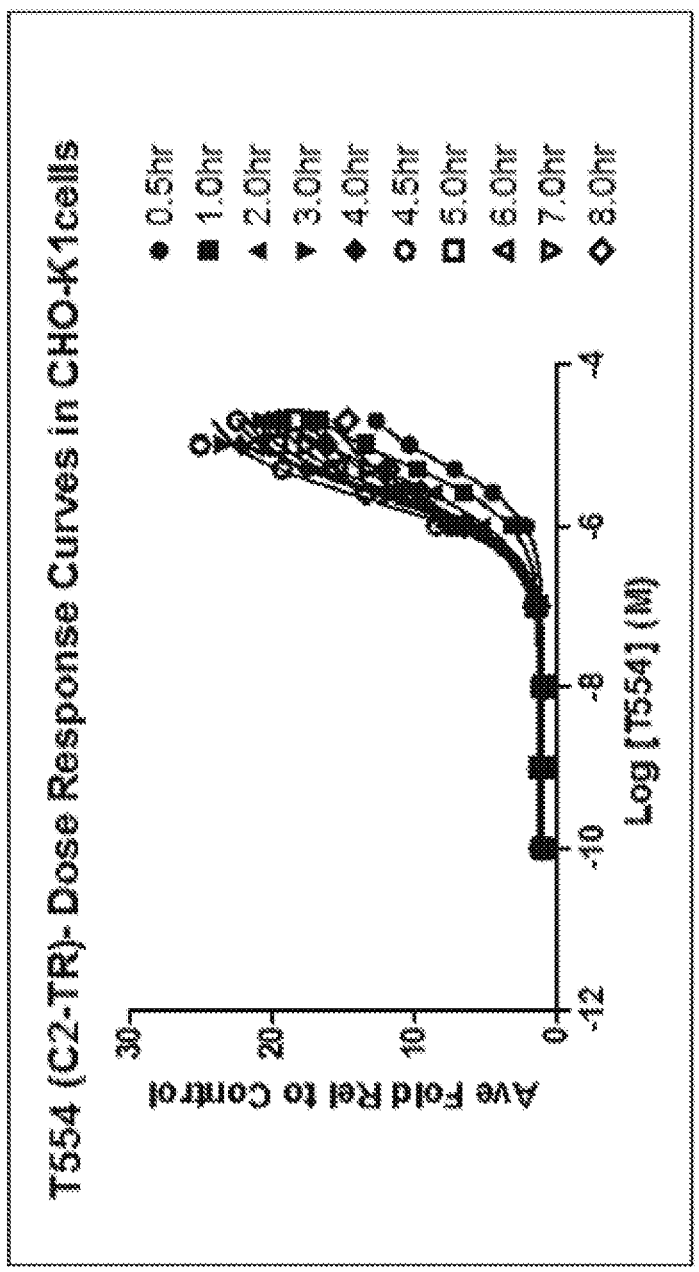
FIG. 8 is a graph of relative cAMP response of CHO-K1-P4 cells ($2.5 \times 10^4$ cells/well) vs. T554 ($C_2$-TR) treprostinil alkyl ester composition challenge, at various dosages and time points.
Figure 9:
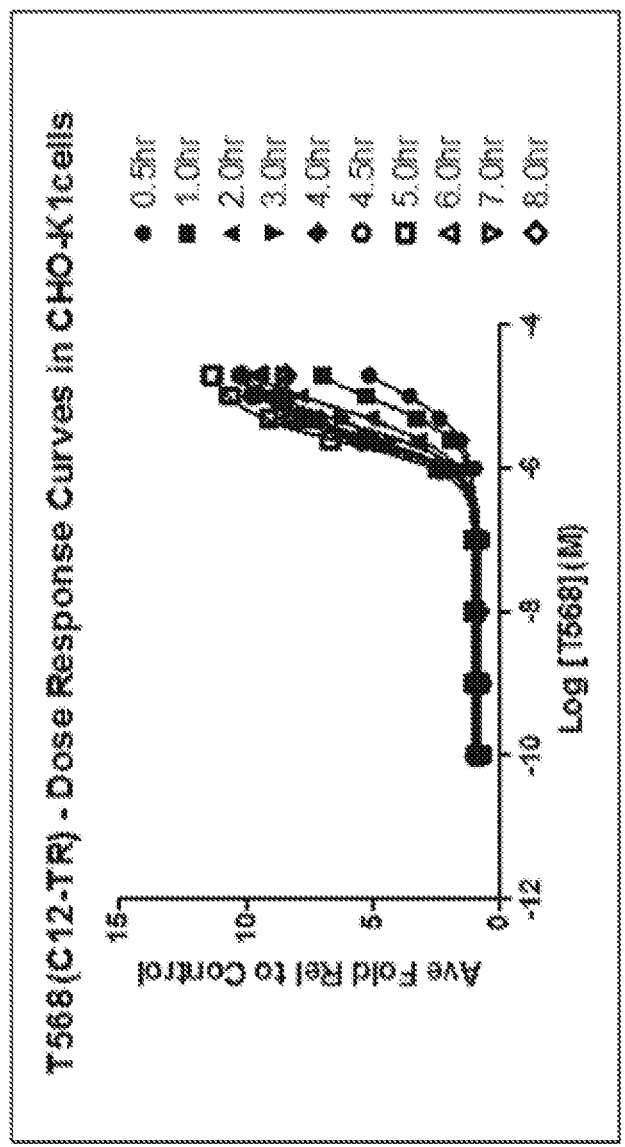
FIG. 9 is a graph of relative cAMP response of CHO-K1-P4 cells ($2.5 \times 10^4$ cells/well) vs. T568 ($C_{12}$-TR) treprostinil alkyl ester composition challenge, at various dosages and time points.
Figure 10:
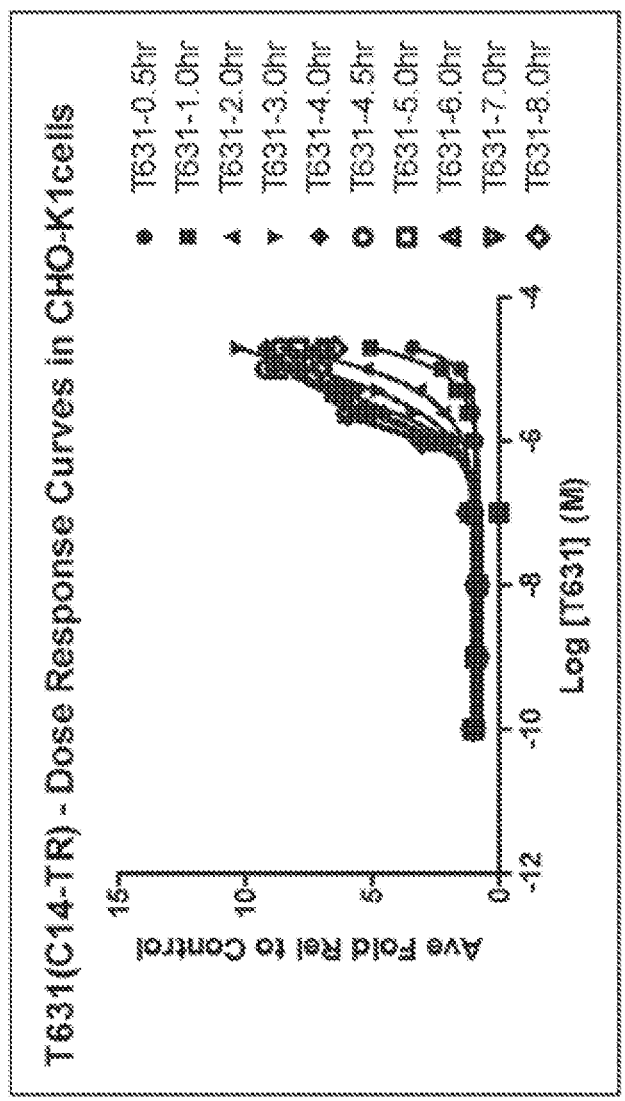
FIG. 10 is a graph of relative cAMP response of CHO-K1-P4 cells ($2.5 \times 10^4$ cells/well) vs. T631 ($C_{14}$-TR) treprostinil alkyl ester composition challenge, at various dosages and time points.
Figure 11:
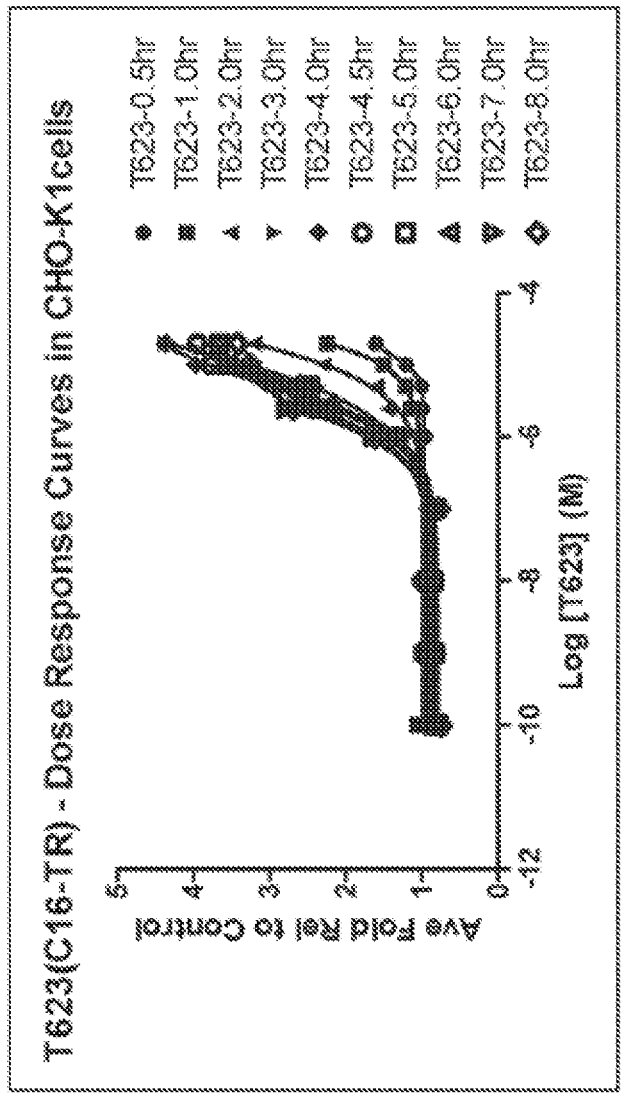
FIG. 11 is a graph of relative cAMP response of CHO-K1-P4 cells ($2.5 \times 10^4$ cells/well) vs. T623 ($C_{16}$-TR) treprostinil alkyl ester composition challenge, at various dosages and time points.
Figure 12:
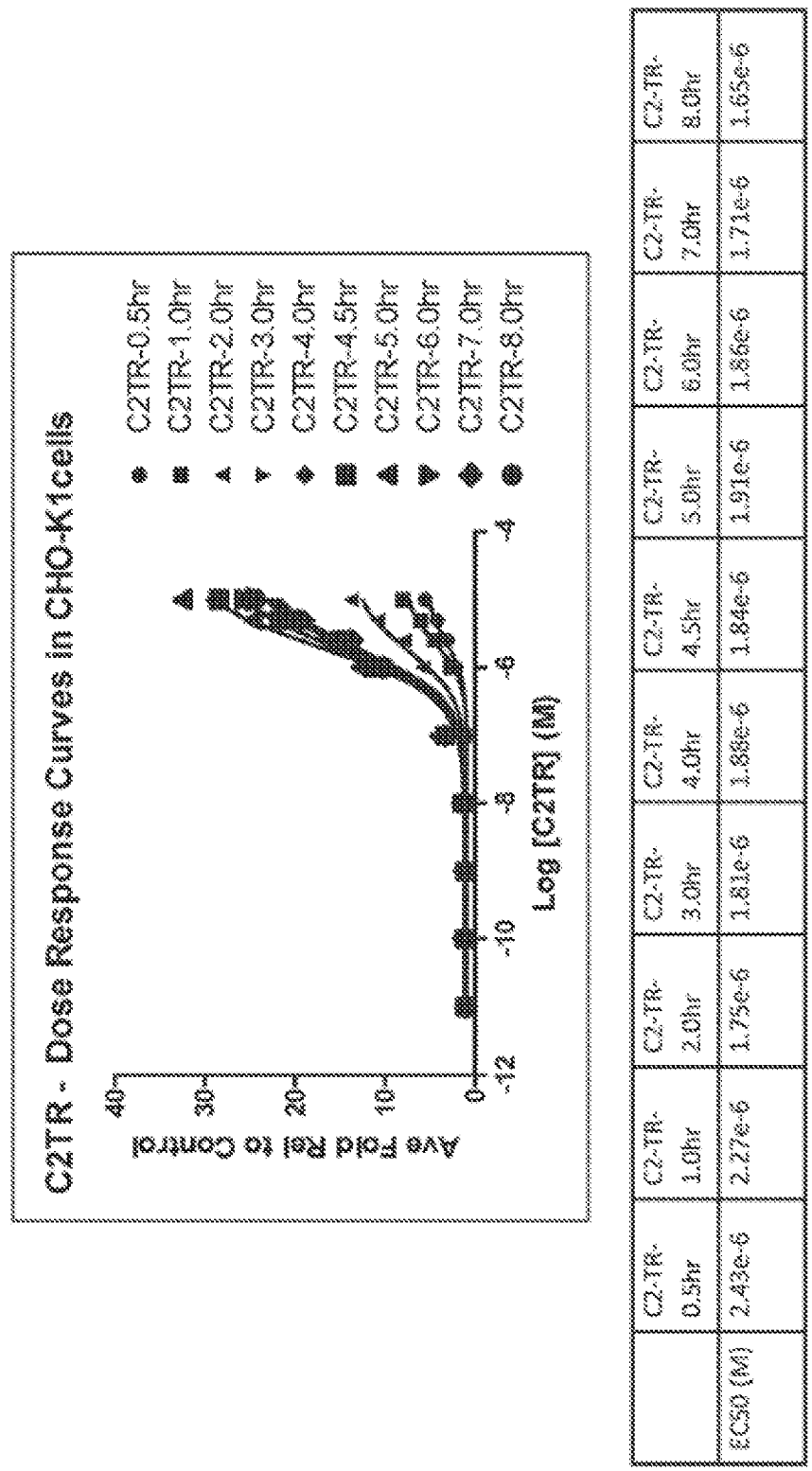
FIG. 12 is a graph of relative cAMP response of CHO-K1-P4 cells ($2.5 \times 10^4$ cells/well) vs. treprostinil ethyl ester ($C_2$)) compound challenge, at various dosages and time points.
Figure 13:
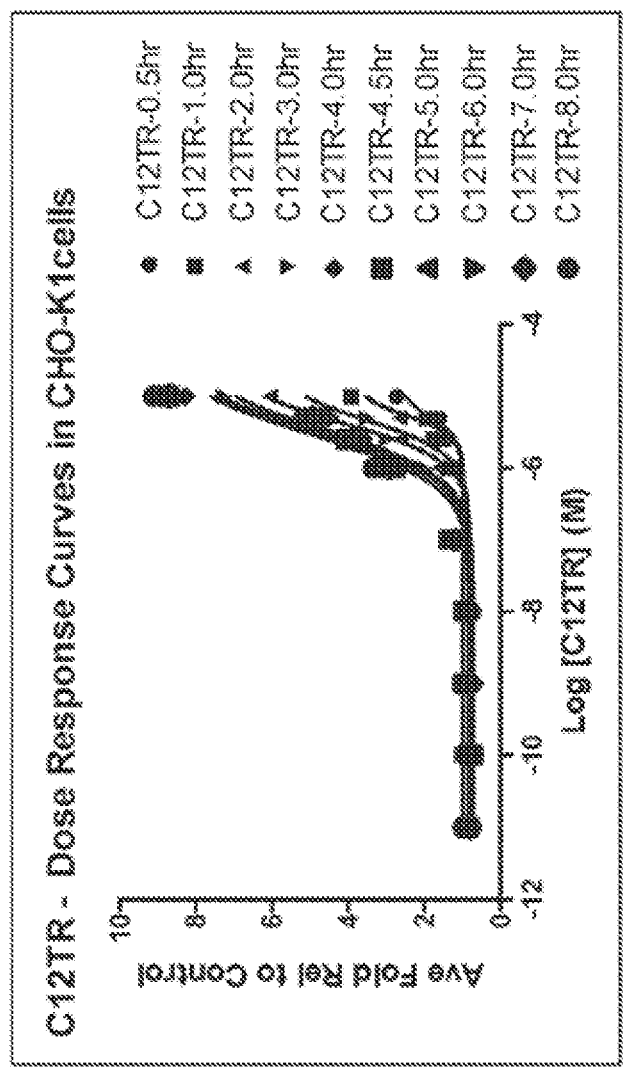
FIG. 13 is a graph of relative cAMP response of CHO-K1-P4 cells ($2.5 \times 10^4$ cells/well) vs. treprostinil ethyl ester ($C_{12}$) compound challenge, at various dosages and time points.
Figure 14:
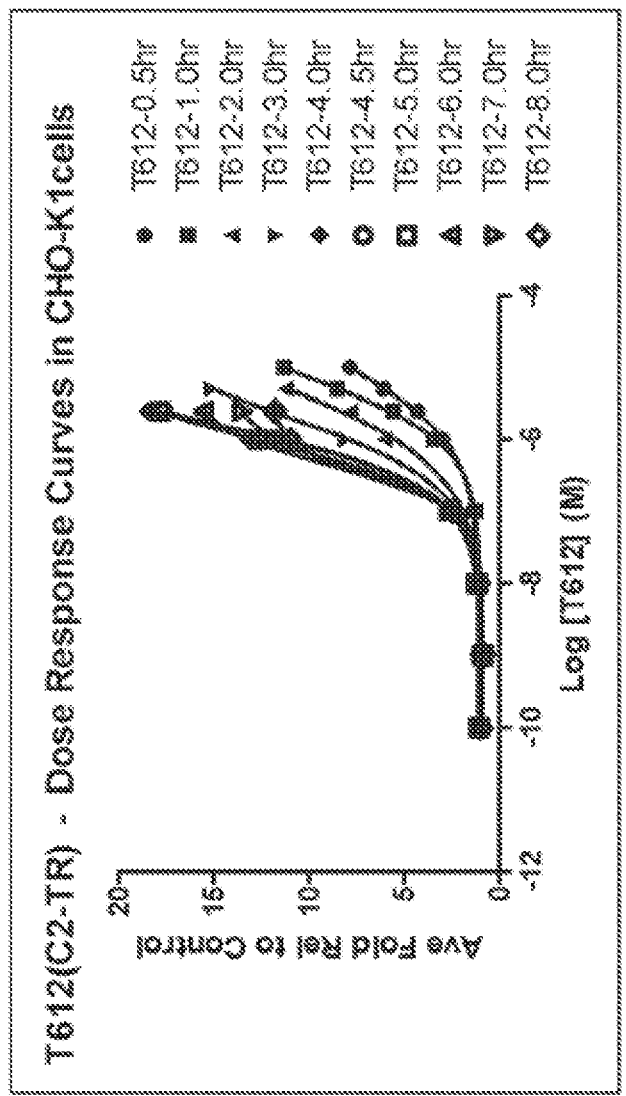
FIG. 14 is a graph of relative cAMP response of CHO-K1-P4 cells ($2.5 \times 10^4$ cells/well) vs. treprostinil ethyl ester ($C_2$) compositions, at various dosages and time points.

Results of these experiments using the 5 µM dose are provided at FIG. 4 and FIG. 5. cAMP response to the $C_2$ and $C_{10}$ treprostinil alkyl esters (5 µM) was greater than or equivalent to the response induced by free treprostinil (FIG. 4). The cAMP levels in response to the $C_2$ and $C_{10}$ treprostinil alkyl ester compounds were sustained significantly longer than free treprostinil and the $C_6$, $C_8$, and $C_{12}$ treprostinil derivatives.

levels equivalent to free treprostinil. The $C_{12}$ derivatized treprostinil compound was found to induce the smallest cAMP response.

Nebulized Treprostinil Ester Compositions

The cell based (CHO-K1) cAMP assay described above was also used to characterize the effect of nebulization of various treprostinil compositions on cAMP levels.

CHO-K1 cells co-transfected with the EP2 receptor and GloSensor™ plasmid were challenged with 10 µM free treprostinil (control or nebulized) and 10 µM treprostinil compositions comprising a compound derivatized with either a $C_2$, $C_8$, $C_{10}$, or $C_{12}$ straight chain alkyl group at position $R_2$ of the compound of Formula (A), provided above (control or nebulized).

The compositions tested in this experiment are provided in Table 6 below (results in FIG. 6) cAMP levels were then measured every 5 minutes over a time course of 8 hours.

Nebulizer Aeroneb Pro (Aerogen) was used to nebulize treprostinil derivative compositions. Desired volume of the formulation (usually 3 mL) was loaded to the mesh head of the nebulizer. The head was connected directly to the glass impinger with air-tight seal. Nebulization was carried out using factory settings until the entire sample was nebulized. After nebulization was complete, the head was disconnected; impinger capped and centrifuged 5 min at 600×g to settle the aerosol inside the impinger. The procedure provided nearly 100% yield in collecting the nebulized sample.

As shown in FIG. 6, nebulization of the derivatized treprostinil compositions did not have a deleterious effect on cAMP response levels, or duration of the response.

TABLE 4

Treprostinil alkyl ester compositions shown in FIG. 3.

| Composition (Cx-TR) | Cx-TR mol % | Tocoacetate mol % | Chol-PEG2000 mol % | Squalene mol % | DOPC mol % | Max cAMP level (Fold) |
|---|---|---|---|---|---|---|
| Treprostinil | 100 | | | | | ~16 |
| T543 ($C_6$-TR) | 40 | 40 | 20 | 0 | | ~8 |
| T555 ($C_8$-TR) | 40 | | 10 | 40 | 10 | ~14 |
| T556 ($C_{10}$-TR) | 40 | | 10 | 40 | 10 | ~16 |

TABLE 5

Treprostinil alkyl ester compositions shown in FIG. 4.

| Composition (Cx-TR) (concentration) | Cx-TR mol % | Chol-PEG2000 mol % | Squalane mol % | DOPC mol % | Max cAMP level (Fold) |
|---|---|---|---|---|---|
| Treprostinil | 100 | | | | ~14 |
| T554 ($C_2$-TR) (5 µM) | 40 | 10 | 40 | 10 | ~24 |
| T601 ($C_6$-TR) (5 µM) | 40 | 10 | 40 | 10 | |
| T555 ($C_8$-TR) (5 µM) | 40 | 10 | 40 | 10 | ~13 |
| T556 ($C_{10}$-TR) (5 µM) | 40 | 10 | 40 | 10 | ~17 |
| T568 ($C_{12}$-TR) (5 µM) | 40 | 10 | 40 | 10 | ~9 |

Treprostinil Compounds

The cell based (CHO-K1) cAMP assay was also used to characterize the effect of unformulated treprostinil compounds (i.e., compounds without a hydrophobic additive and/or an amphiphilic agent such as a PEGylated lipid) on cAMP levels.

CHO-K1 cells co-transfected with the EP2 receptor and GloSensor™ plasmid were challenged with free treprostinil (5 µM) and treprostinil derivatives having either a $C_2$, $C_3$, $C_4$, $C_5$, $C_6$, $C_8$, $C_{10}$, or $C_{12}$ straight chain alkyl ester moiety (5 µM) cAMP levels were then measured every 5 minutes over a time course of 8 hours.

Results of these experiments are provided at FIG. 5. $C_2$ and $C_{10}$ treprostinil alkyl esters induced cAMP response

TABLE 6

Treprostinil Alkyl Ester compositions shown in FIG. 4.

| (5 µM) Cx-TR | Cx-TR mol % | Chol-PEG2000 mol % | Squalane mol % | DOPC mol % | Max cAMP level (Fold) |
|---|---|---|---|---|---|
| Treprostinil | 100 | | | | ~15 |
| T554 ($C_2$-TR) | 40 | 10 | 40 | 10 | ~22 |
| T555 ($C_8$-TR) | 40 | 10 | 40 | 10 | ~13 |
| T556 ($C_{10}$-TR) | 40 | 10 | 40 | 10 | ~18 |
| T568 ($C_{12}$-TR) | 40 | 10 | 40 | 10 | ~13 |

Comparison of Treprostinil Compounds and Compositions Comprising the Same

The half maximal effective concentrations ($EC_{50}$) of the various treprostinil compounds were determined using the results from the cAMP assays. Table 7 (below) summarizes the $EC_{50}$ data for cAMP response in CHO-K1 cells for the following compositions and compounds:
T554 ($C_2$-TR 40 mol %, squalane 40 mol %, Chol-PEG2k 10 mol %, DOPC 10 mol %), T612 ($C_2$-TR 10 mol %, DMPE-P1K 90 mol %),
T501 ($C_5$-TR 40 mol %, squalane 40 mol %, Chol-PEG2k 20 mol %),
T601 ($C_6$-TR 40 mol %, squalane 40 mol %, Chol-PEG2k 10 mol %, DOPC 10 mol %),
T555 ($C_8$-TR 40 mol %, squalane 40 mol %, Chol-PEG2k 10 mol %, DOPC 10 mol %),
T556 ($C_{10}$-TR 40 mol %, squalane 40 mol %, Chol-PEG2k 10 mol %, DOPC 10 mol %),
T568 ($C_{12}$-TR 40 mol %, squalane 40 mol %, Chol-PEG2k 10 mol %, DOPC 10 mol %),
T621 ($C_{12}$-TR 10 mol %, DPPE-P2K 90 mol %),
T623 ($C_{16}$-TR 40 mol %, squalane 40 mol %, Chol-PEG2k 10 mol %, DOPC 10 mol %),
T622 ($C_{16}$-TR 10 mol %, DPPE-P2K 90 mol %),
$C_2$-TR (100 mol %),
$C_8$-TR (100 mol %),
$C_{12}$-TR (100 mol %) and
free treprostinil.

A subset of the dose response curves for selected treprostinil compounds and compositions are provided in FIGS. 7-14. With free treprostinil, the potency decreases with increasing incubation time (supporting an immediate response), while all the various treprostinil compositions exhibit an increasing potency with incubation time (suggestive of a delay-release profile).

Pen-Strep (Life Technologies, cat #15140-122) was then added at a volume of 10 mL. Cells were centrifuged at 250 g for 5 minutes at room temperature and the media was aspirated. The cell pellet was resuspended in 10 mL complete growth media. Cell number was determined using a hemacytometer. Cells were then seeded at 2000 cells per well of a 96-well plate in 100 μL of complete growth media. The plate was incubated overnight at 37° C. and 5% $CO_2$ in a water-jacketed incubator.

The next day, 80 μL of fresh complete media was added to each well, and CHO-K1 cells were challenged with treprostinil compound and composition treatments. The working solutions were prepared at 10× concentration, and following 2 fold serial dilutions, 20 μL aliquots were added per well to arrive at a final 1× concentration. Following a 48 hour incubation at 37° C. and 5% $CO_2$ in a water-jacketed incubator, the inhibitory effect on cell proliferation was determined. Plates were analyzed using 20 μL of Presto Blue reagent (Life Technologies, cat #: A13262) per well. The reagent was mixed, and plates were incubated for 1 hour at 37° C. and 5% $CO_2$ in a water-jacketed incubator. Plates were read using either a CytoFluor Series 4000 (PerSeptive BioSystems) or Synergy Neo microplate reader (BioTek) with emission λ: 590 nm and excitation λ: 560 nm. The percent inhibition was determined using the following formula: % inhibition=100%−(treated samples/control×100%).

TABLE 7

$EC_{50}$ values for treprostinil compositions.

| | $EC_{50}$ (μM) | | | | | | | | | |
|---|---|---|---|---|---|---|---|---|---|---|
| Samples | 0.5 hr | 1.0 hr | 2.0 hr | 3.0 hr | 4.0hr | 4.5 hr | 5.0 hr | 6.0 hr | 7.0 hr | 8.0 hr |
| Treprostinil | 0.18 | 0.28 | 0.15 | 0.16 | 0.19 | 0.2 | 0.26 | 0.29 | 0.46 | 0.44 |
| T554 ($C_2$-TR) | 5.96 | 6.05 | 5.25 | 2.43 | 2.14 | 2.12 | 2.22 | 2.31 | 2.28 | 1.96 |
| T501 ($C_5$-TR) | 15.4 | 15.4 | 10.9 | 5.98 | 5.07 | 5.07 | 4.46 | 4.11 | 3.92 | |
| T601 ($C_6$-TR) | ~0.0093 | 45.2 | 14.4 | 75.0 | 22.0 | 21.3 | 24.56 | 9.35 | 6.17 | 4.94 |
| T555 ($C_8$-TR) | 20.8 | 15.1 | 5.65 | 4.10 | 2.99 | 2.66 | 2.41 | 2.03 | 1.71 | 1.48 |
| T556 ($C_{10}$-TR) | ~6.83 | 4.94 | 1.69 | 1.80 | 2.20 | 2.09 | 2.34 | 1.78 | 1.51 | 2.20 |
| T568 ($C_{12}$-TR) | 12.2 | 8.07 | 6.54 | 4.12 | 3.21 | 3.06 | 2.37 | 2.33 | 2.24 | 2.03 |
| T631 ($C_{14}$-TR) | ~0.0015 | ~0.0088 | 34.1 | 12.4 | 3.97 | 2.79 | 2.17 | 1.88 | 1.45 | 1.23 |
| T623 ($C_{16}$-TR) | 13.7 | ~0.0090 | 42.9 | 24.8 | 5.10 | 4.59 | 3.87 | 2.78 | 1.97 | 1.77 |
| $C_2$-TR (constrain) | 2.43 | 2.27 | 1.75 | 1.81 | 1.88 | 1.84 | 1.91 | 1.68 | 1.71 | 1.65 |
| $C_8$-TR (constrain) | 3.69 | 3.39 | 1.69 | 1.42 | 1.53 | 1.41 | 1.4 | 1.4 | 1.34 | 1.09 |
| $C_{12}$-TR (constrain) | 4.98 | 5.35 | 4.54 | 4.07 | 3.13 | 3.17 | 2.94 | 3.25 | 3.17 | 2.9 |
| T612 ($C_2$-TR) | 10.0 | 7.08 | 7.9 | 2.23 | 2.76 | 1.54 | 0.88 | 0.44 | 0.41 | 0.28 |
| T622 ($C_{20}$-TR) | ~0.012 | 24.6 | 3.53 | 2.2 | 8.29 | 25.2 | 16.3 | 3.9 | 1.90 | 1.14 |

Constrain: All $EC_{50}$ values were generated using GraphPad Prism 5 software. For samples, $C_7$-TR, $C_8$-TR and $C_{12}$-TR, the data were analyzed by constraining the top and bottom parameter to a constant number corresponding to the highest and lowest value respectively, generated from the cAMP assay.
*For samples T612 ($C_2$-TR); T622 ($C_{36}$-TR), because of toxicity at higher concentrations, those values were excluded from the analyses in order to generate an $EC_{50}$ value.

Example 5—Determination of the Effect of Treprostinil Compounds on Cell Proliferation In order to determine any effect of treprostinil compounds on cell proliferation, cell based assays using CHO-K1 cells and rat alveolar cells (NR8383 cells) were performed.

CHO-K1 Cells

CHO-K1 cells were harvested when the cell monolayer was 50-90% confluent (use passage 4-11). Media was aspirated out of the flask, and cells were rinsed with 2 mL of F12 media. Next, 1 mL of pre-warmed (37° C.) 0.25% trypsin-EDTA (Life Technologies, Cat#: 25300054) was added, and cells were dislodged front the flask by tapping it on the side. Complete growth media (F12 (Life Technologies, Cat #: 31765092)+10% FBS (Hyclone, Cat #: SH30071.03)+1×

NR8383 Cells

Rat alveolar NR8383 cells were harvested when the monolayer was 50-90% confluent (use passage 5-11) Because the NR8383 cells include both adherent and non-adherent cells, media was transferred to a 50 mL Falcon tube. To obtain the cells remaining in the flask, 2 mL of plain media was added, and the remaining cells were scraped out of the 75 $cm^2$ flask with a cell scraper and added to the 50 mL tube. Cells were centrifuged at 200×g for 5 minutes at room temperature, and the media was aspirated. The cell pellet was resuspended in 10 mL complete growth media (F12 (Life Technologies, Cat #: 31765092)+15% FBS—heat inactivated (Hyclone, Cat #: SH30071.03)+1×Pen-Strep (Life Technologies, cat #: 15410-122)). Cell number was determined using a hemacytometer. Cells were then seeded at 4000 cells per well of a 90-well plate in 100 μL of complete growth media. The plate was incubated overnight at 37° C. and 5% $CO_2$ in a water-jacketed incubator.

The next day, 80 μL of fresh complete media was added to each well, and the NR8383 cells were challenged with treprostinil compound treatments. Following a 72 hour incubation at 37° C. and 5% $CO_2$ in a water-jacketed incubator, the inhibitory effect on cell proliferation was determined. Measurements and calculations were made as described above for the CHO-K1 cells.

Effect of Treprostinil Alkyl Ester Compositions on CHO-K1 Cell Proliferation

CHO-K1 cells were challenged with compositions comprising treprostinil alkyl ester derivatives: T554 ($C_2$-TR 40 mol %, squalane 40 mol %, Chol-PEG2k 10 mol %, DOPC 10 mol %), T543 ($C_6$-TR 40 mol %, Toco Acet 40 mol %, Chol-PEG2k 10 mol %), T555 ($C_8$-TR 40 mol %, squalane 40 mol %, Chol-PEG2k 10 mol %, DOPC 10 mol %), T556 ($C_{10}$-TR 40 mol %, squalane 40 mol %, Chol-PEG2k 10 mol %, DOPC 10 mol %), T568 ($C_{12}$-TR 40 mol %, squalane 40 mol %, Chol-PEG2k 10 mol %, DOPC 10 mol %), T623 ($C_{16}$-TR 40 mol %, squalane 40 mol %, Chol-PEG2k 10 mol %, DOPC 10 mol %), at concentrations ranging from 0.55 μM to 125 μM following a 48 hour incubation period, the inhibitors effect of the treprostinil derivative compositions on cell proliferation was determined.

Table 8 below summarizes the effect of the above treprostinil compositions on CHO-K1 cell proliferations. At the highest concentration of 100 μM, only T543 ($C_6$-TR) and T623 ($C_{16}$-TR) exhibited a significant inhibitory effect on cell proliferation.

TABLE 8

Effect of Treprostinil Compositions on cell proliferation.

| Samples | CHO-K1 Cells (<100 μM-0.78 μM) | NR8383 Cells (≤100 μM-0.78 μM) |
|---|---|---|
| T543 ($C_6$-TR) | Detectable cell inhibition only at 100 μM concentration | Detectable cell proliferation inhibition only at concentration > 25 μM |
| T554 ($C_2$-TR) | No detectable cell proliferation inhibition | Detectable cell proliferation inhibition at 70 μM |
| T555 ($C_8$-TR) | No detectable cell proliferation inhibition | Detectable cell proliferation inhibition only at concentration > 50 μM |
| T556 ($C_{10}$-TR) | No detectable cell proliferation inhibition | Detectable cell proliferation inhibition only at concentration > 50 μM |
| T568 ($C_{12}$-TR) | No detectable cell proliferation inhibition | Detectable cell proliferation inhibition only at concentration > 100 μM |
| T623 ($C_{16}$-TR) | Detectable cell proliferation inhibition only at 100 μM concentration | Detectable cell proliferation inhibition only at 100 μM concentration |

Effect of Treprostinil Compositions on NR8383 Cell Proliferation

Rat alveolar NR8383 cells were challenged with the same treprostinil derivative compositions: T543 ($C_6$-TR 40 mol %, Toco Ace 40 mol %, Chol-PEG2k 20 mol %), T554 ($C_2$-TR 40 mol %, squalane 40 mol %, Chol-PEG2k 10 mol %, DPPC 10 mol %), T555 ($C_8$-TR 40 mol %, squalane 40 mol %, Chol-PEG2k 10 mol %, DOPC 10 mol %), T556 ($C_{10}$-TR 40 mol %, squalane 40 mol %, Chol-PEG2k 10 mol %, DOPC 10 mol %), T568 ($C_{12}$-TR 40 mol %, squalane 40 mol %, Chol-PEG2k 10 mol %, DOPC 10 mol %), and T623 ($C_{16}$-TR 40 mol %, squalane 40 mol %, Chol-PEG2k 10 mol %, DOPC 10 mol %), at the same concentrations (0.55 μM to 125 μM) as the CHO-K1 cells above. Following a 72 hour incubation period, the inhibitory effect of the treprostinil derivative compositions on cell proliferation was determined.

Table 3 above summarizes the effect of the above treprostinil compositions on NR8383 cell proliferation. At the highest dose of 100 μM, all of the treprostinil derivative compositions demonstrated some inhibition of cell proliferation, and T543 ($C_6$-TR) exhibited the greatest inhibitory effect.

Effect of Treprostinil Alkyl Ester Compounds on Cell Proliferation

In order to determine any effect of treprostinil derivative compounds (unformulated) on cell proliferation, the cell based assays described above, using CHO-K1 cells and rat alveolar cells (NR8383 cells) were performed.

CHO-K1 Cell Proliferation Assay

CHO-K1 cells were challenged with treprostinil alkyl esters, i.e., TR compounds of Formula (A), having the following $R_2$ groups:

$C_2$, $C_3$, $C_4$, $C_5$, $C_6$, $C_8$, $C_{10}$ or $C_{12}$ straight chain alkyl, at dosages ranging from 0.098 μM to 25 μM Following a 48 hour incubation period, the inhibitory effect on cell proliferation was determined.

Table 9 below summarizes the effect of the above treprostinil alkyl esters on CHO-K1 and NR8383 cell proliferation. At the highest concentration, only the treprostinil octyl ester compound showed inhibition of cell proliferation.

TABLE 9

Effect of treprostinil alkyl esters on cell proliferation

| Samples | CHO-K1 Cells (0.195 μM-25 μM) | NR8383 Cells (0.195 μM-25 μM) |
|---|---|---|
| $C_2$-TR | No detectable cell inhibition | No detectable cell inhibition |
| $C_3$-TR | No detectable cell inhibition | No detectable cell inhibition |
| $C_4$-TR | No detectable cell inhibition | No detectable cell inhibition |
| $C_5$-TR | No detectable cell inhibition | No detectable cell inhibition |
| $C_6$-TR | No detectable cell inhibition | No detectable cell inhibition |
| $C_8$-TR | Detectable cell inhibition at 25 μM | Some detectable cell inhibition |
| $C_{10}$-TR | No detectable cell inhibition | No detectable cell inhibition |
| $C_{12}$-TR | No detectable cell inhibition | No detectable cell inhibition |

NR8383 Cell Proliferation Assay

Rat alveolar NR8383 cells were challenged with treprostinil compounds derivatized at the $R_2$ position of Formula (A) with a $C_2$, $C_3$, $C_4$, $C_5$, $C_6$, $C_8$, $C_{10}$ or $C_{12}$ straight chain alkyl moiety at concentrations ranging from 0.195 μM to 25 μM. Following a 72 hour incubation period, the inhibitory effect on cell proliferation was determined.

Table 11 above summarizes the effect of the above treprostinil alkyl esters on NR8383 cell proliferation. Similar to the CHO-K1 cell assay, only the treprostinil octyl ester showed some inhibition of cell proliferation at the highest concentration.

Treprostinil Derivative Compositions—Effect on Cell Proliferation

In order to determine the effect of treprostinil derivative compositions on cell proliferation, cell based assays using CHO-K1 cells and rat alveolar cells (NR8383 cells) were performed.

Effect of Treprostinil Compositions on CHO Cell Proliferation

CHO-K1 cells were challenged with treprostinil derivative compositions: T596 ($C_2$-TR 45 mol %, DSG-P2K 55 mol %), T597 ($C_6$-TR 45 mol %, DSG-P2K 55 mol %), T598 ($C_8$-TR 45 mol %, DSG-P2K 55 mol %), T599 ($C_{10}$-TR 45 mol %, DSG-P2K 55 mol %), and T600 ($C_{12}$-TR 45 mol %, D5G-P2K 55 mol %), T612 ($C_2$-TR 10 mol %, DMPE-P1K 90 mol %), T613 ($C_8$-TR 10 mol %, DMPE-P1K 90 mol %), at concentrations ranging from 0.23 µM to 29 µM. Following a 72 hour incubation period, the inhibitory effect on cell proliferation was determined. Following a 48 hour incubation period, the inhibitory effect on cell proliferation was determined.

Table 10 below summarizes the effect of the treprostinil compositions on CHO-K1 cell proliferation. None of the compositions tested exhibited a significant inhibitory effect on CHO-K1 cell proliferation.

Effect of treprostinil compositions on cell proliferation.

| Samples | CHO-K1 Cells | NR8383 Cells |
|---|---|---|
| Sample concentration | (29 µM-0.23 µM) | (29 µM-0.23 µM) |
| T596 ($C_2$) | No detectable cell proliferation inhibition | Some detectable cell proliferation inhibition only at concentration > 25 uM |
| T597 ($C_6$) | No detectable cell proliferation inhibition | Some detectable cell proliferation inhibition at 70 uM |
| T598 ($C_8$) | No detectable cell proliferation inhibition | Some detectable cell proliferation inhibition only at concentration > 50 uM |
| T599 ($C_{10}$) | No detectable cell proliferation inhibition | Some detectable cell proliferation inhibition at ≥ 14.5 uM concentration |
| T600 ($C_{12}$) | No detectable cell proliferation inhibition | Some detectable cell proliferation inhibition at ≥ 14.5 uM concentration |
| Sample concentration | (180 µM-1.41 µM) | (180 µM-1.41 µM) |
| T612 ($C_2$) | Detectable cell proliferation inhibition at ≥ 90 µM concentration | Detectable cell proliferation inhibition only at 180 µM concentration |
| T613 ($C_8$) | Detectable cell proliferation inhibition at ≥ 90 µM concentration | Detectable cell proliferation inhibition only at 180 µM concentration |

Similarly, CHO-K1 cells were challenged with the treprostinil compositions T612 ($R_2$=$C_2$), T613 ($R_2$=$C_8$) at concentrations ranging from 1.41 µM to 180 µM. After 48 hours, the inhibitory effect on cell proliferation was determined, and all four of the treprostinil compositions exhibited 100% inhibition of cell proliferation at the higher concentrations.
Effect of Treprostinil Compositions on NR8383 Cell Proliferation Rat alveolar NR8383 cells were challenged with the same treprostinil compositions (above) as well as T596 ($C_2$-TR 45 mol %, DSG-P2K 55 mol %), T612 ($C_2$-TR 10 mol %, DMPE-P1K 90 mol %), T597 ($C_6$-TR 45 mol %, DSG-P2K 55 mol %), T598 ($C_8$-TR 45 mol %, DSG-P2K 55 mol %), T613 ($C_8$-TR 10 mol %, DMPE-P1K 90 mol %), T599 ($C_{10}$-TR 45 mol %, DSG-P2K 55 mol %), T600 ($C_{12}$-TR 45 mol %, DSG-P2K 55 mol %), and at the same concentrations (0.23 µM to 29 µM) as the CHO-K1 cells above, following a 72 hour incubation period, the inhibitory effect on cell proliferation was determined.

Table 10 above summarizes the effect of the treprostinil composition on NR8383 cell proliferation. All of the treprostinil compositions demonstrated some (≤10%) inhibition of NR8383 cell proliferation.

Example 6—Treprostinil Compounds In Vivo

The effect of treprostinil derivative compounds in vivo was determined by using rat models. Young male rats Sprague Dawley (Charles River) were used for the study. Rats anesthetized with ketamine/xylazine, placed on a heating pad and after surgical isolation and catheterization of the trachea, mechanically ventilated throughout the study.

A catheter was placed in the femoral artery for measurement of systolic (sys) and diastolic (dias) blood pressures. A thoracotomy was performed and a catheter inserted into the right ventricle and positioned in the pulmonary artery for the measurement of pulmonary arterial systolic and diastolic blood pressures. Oxygen saturation ($SaO_2$) was measured with a pulse oximeter placed on the paw.

With the rats ventilated on room air ($FIO_2$=0.21), cardiovascular measurements were made under these normoxic conditions. In order to induce hypoxia the FIO2 was reduced over a 30 min period until SaO2 fell to values between 50-60%, and a baseline hypoxia value for each of the parameters was determined.

Groups of four rats each received either PBS, free treprostinil (1.7 µg/kg and 10 µg/kg), or a composition comprising $C_2$-TR (T554); $C_8$-TR (T555: $C_8$-TR 40 mol %, squalane 40 mol %, Chol-PEG2k 10 mol %, DOPC 10 mol %) (38.6 µg/kg), $C_{10}$-TR (T556: $C_{10}$-TR 40 mol %, squalane 40 mol %, Chol-PEG2k 10 mol %, DOPC 10 mol %) (40.8 µg/kg)), $C_{12}$-TR (T568).

The target dose varied slightly by weight due to the differences in molecular weight of the treprostinil derivative compositions as shown in Table 11 below. The actual achieved lung dose was about 5× lower than provided in Table 11 (e.g., administration of 10 µg/kg yielded about 2 µg/kg in the lungs). The various treatments were delivered (via inhalation of nebulized drug to the lungs of the rats. The pulmonary arterial pressure (PAP), systemic arterial pressure (SAP), and heart rate of the rats were measured continuously for 180 minutes. The PAP signal was collected at 200 points per second.

TABLE 11

| Target Doses in Acute Hypoxia Rat Model | | | |
|---|---|---|---|
| | | Target Dose (µg/kg) | Target Dose (nmole/kg) |
| Treprostinil | | 1.7 | 4.35 |
| | | 10 | 25.6 |
| | | 30 | 76.8 |
| Treprostinil derivative compound | $C_2$* | 32.1 | 76.8 |
| | $C_6$* | 36.4 | 76.8 |
| | $C_8$* | 38.6 | 76.8 |
| | $C_{10}$* | 40.8 | 76.8 |
| | $C_{12}$* | 42.9 | 76.8 |
| | $C_{16}$* | 47.2 | 76.8 |

*Indicates alkyl chain length at position $R_2$ of the compound of Formula (A).

Figure 15A:
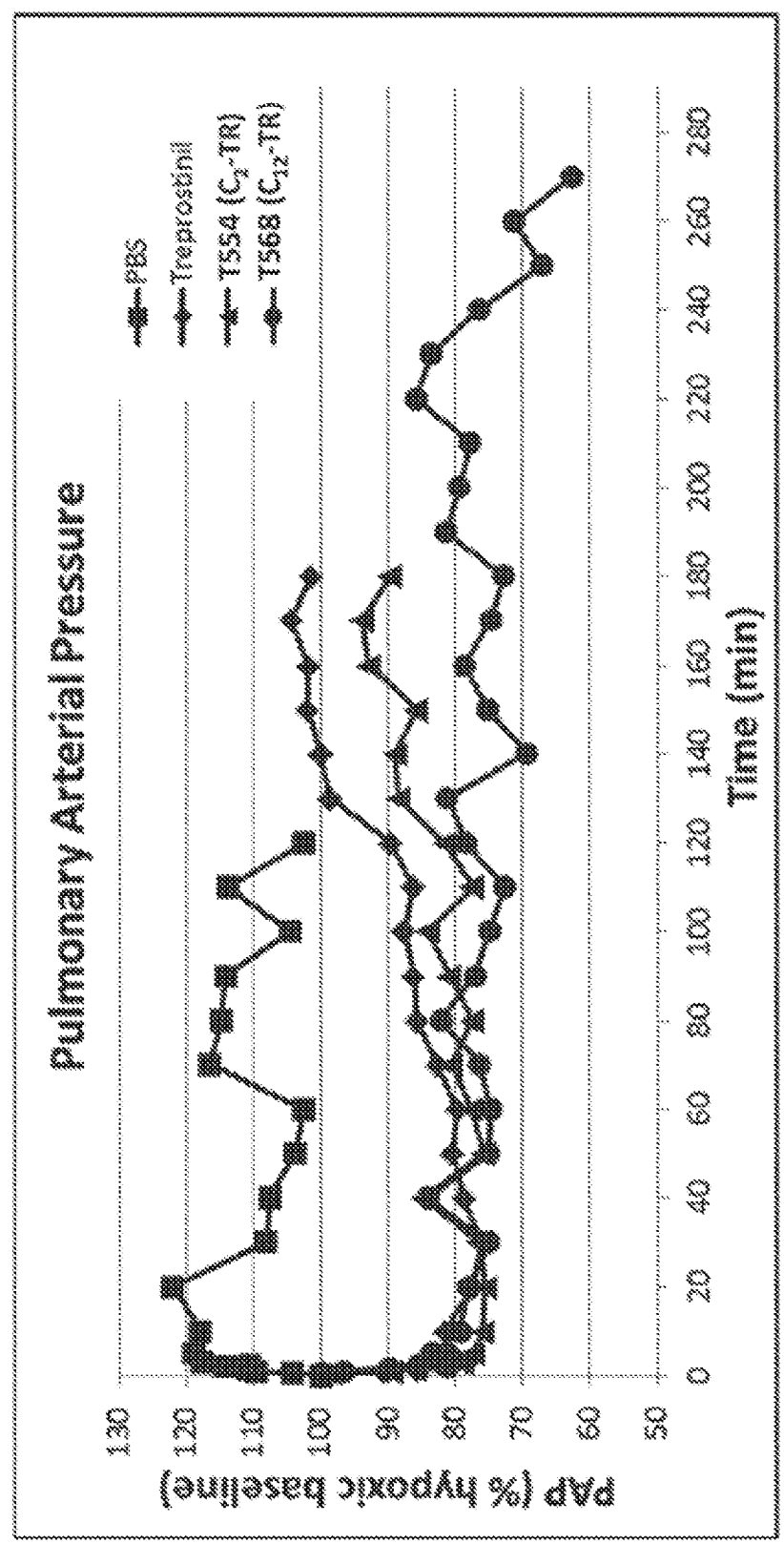
FIG. 15A is a graph of pulmonary arterial pressure (expressed as a percent of the starting hypoxia value) vs. time, in response to animal challenge with phosphate buffered saline (PBS), treprostinil, and prostacyclin compositions (T554 ($C_2$) and T-568 ($C_{12}$)). The target dose for treprostinil and prostacyclin alkyl esters was 76.8 nmole/kg; the achieved deposited dose may be 5× lower than these target values.
Figure 15B:
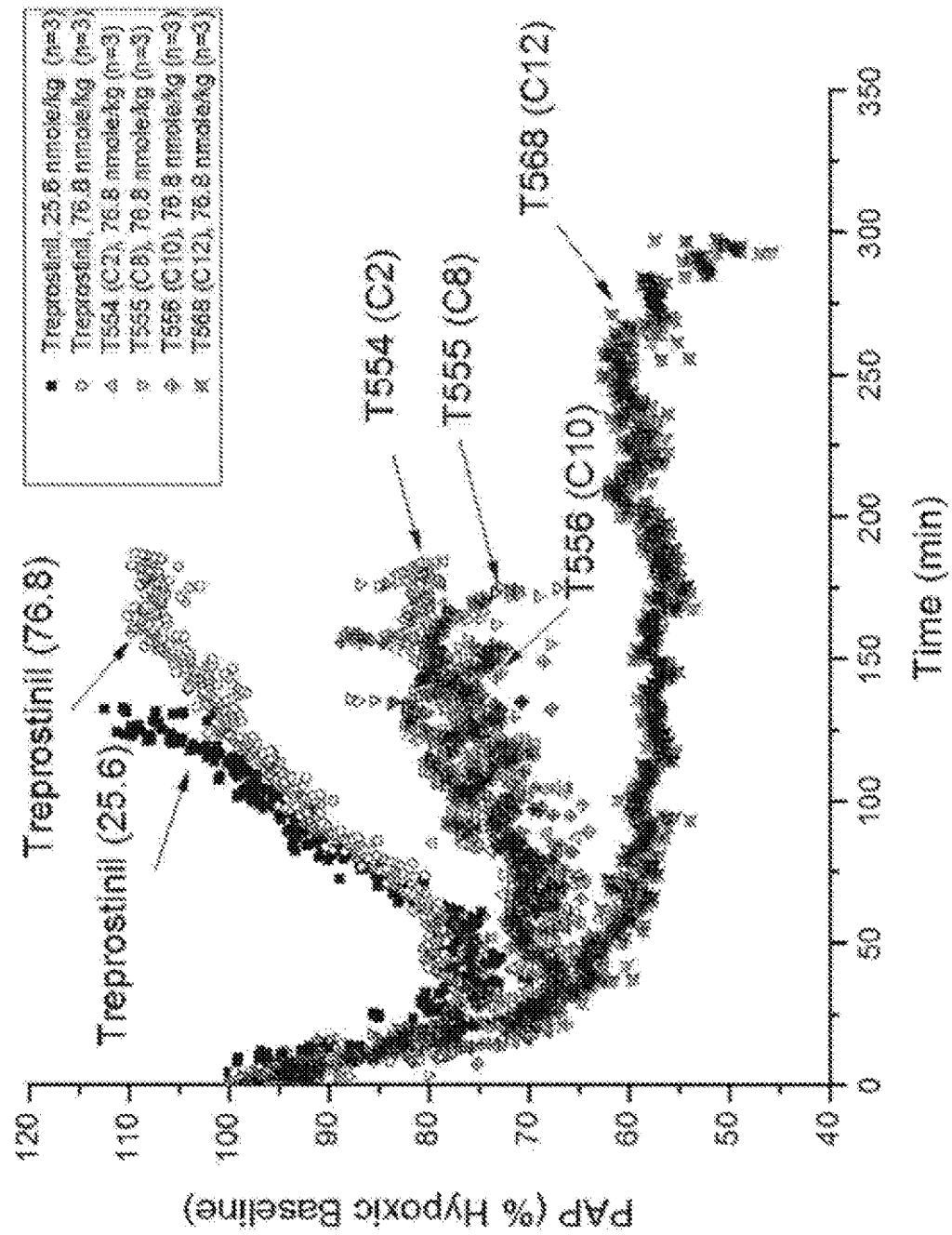
FIG. 15B is a dot plot drawing the effect of treprostinil and $C_2$, $C_8$, $C_{10}$, and $C_{12}$ treprostinil alkyl ester compositions on PAP (expressed as a percent of the starting hypoxia value) in an in vivo acute hypoxia rat model of PAH. Doses were target values and actual achieved lung doses may be approximately 5× lower.
Figure 16:
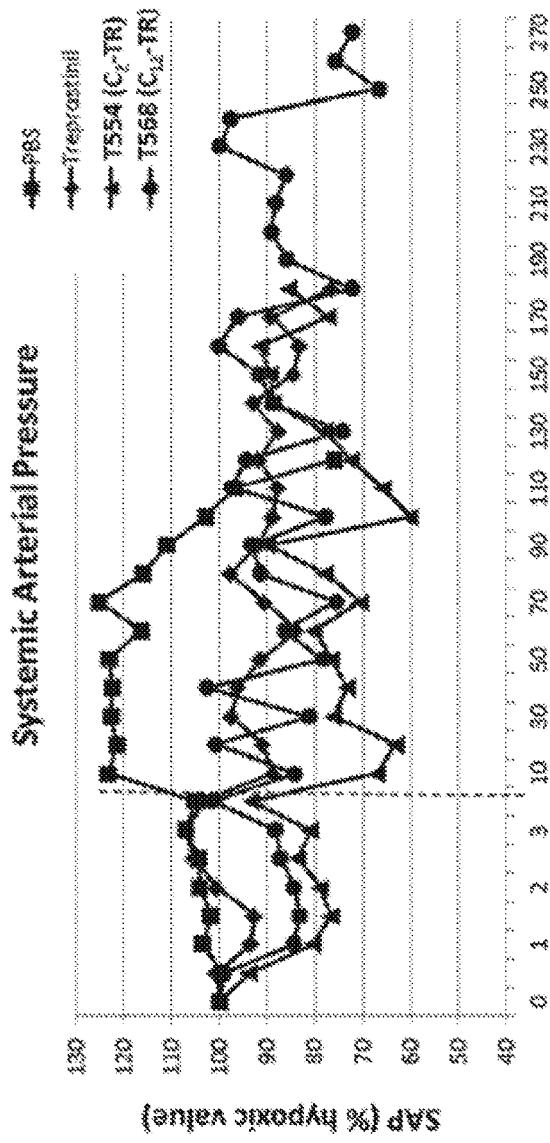
FIG. 16 is a graph of systemic arterial pressure (expressed as a percent of the starting hypoxia value) vs. time, in response to animal challenge with PBS, treprostinil, and treprostinil alkyl ester compositions (T554 ($C_2$-TR) and T-568 ($C_{12}$-TR)) in an in vivo acute hypoxia rat model of PAH. The vertical dotted line marks change in x-axis time increments. The target dose for treprostinil and prostacyclin alkyl esters was 768 nmole/kg; the achieved deposited dose may be 5× lower than these target values.
Figure 17:
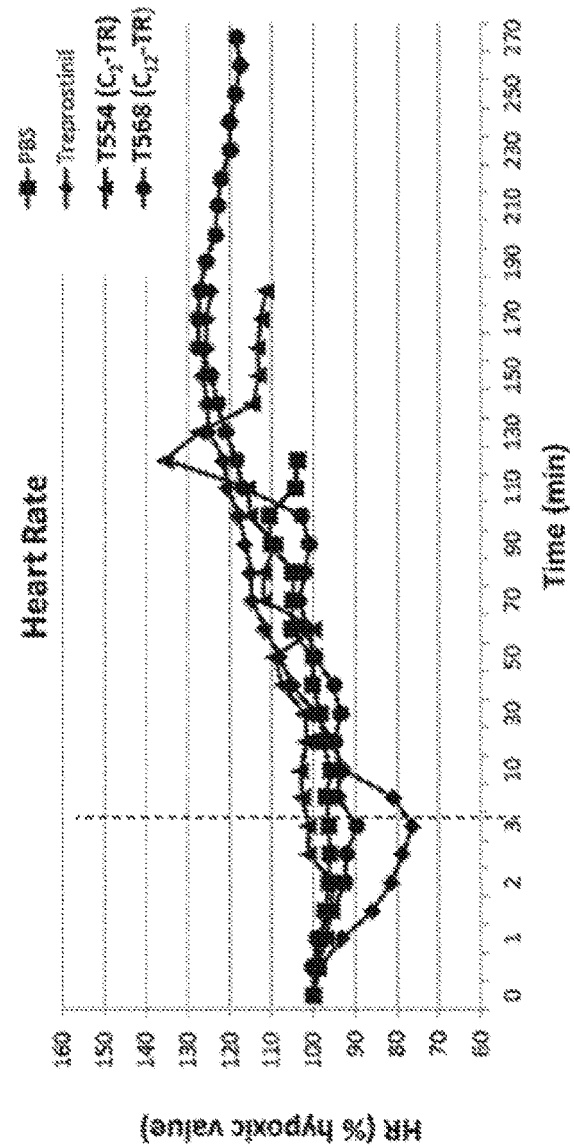
FIG. 17 is a graph of in vivo heart rate (expressed as a percent of the starting hypoxia value) vs. time, in response to animal challenge with PBS, treprostinil and treprostinil alkyl ester compositions (T554 ($C_2$) and T-568 ($C_{12}$)) in an in vivo acute hypoxia rat model of PAH. The vertical dashed line marks change in x-axis time increments. The target dose for treprostinil and prostacyclin alkyl esters was 76.8 nmole/kg; the achieved deposited dose may be 5× lower than these target values.

The normalized variation of mean PAP (mPAP) is shown as a percentage from the hypoxic baseline value at (T=0) in FIG. 15. The hypoxic baseline PAP value was 100%, and the changes in pressure were measured in comparison to the hypoxic baseline. The normalized variation of mean SAP (mSAP) is shown as a percentage from the hypoxic baseline value in FIG. 16. Heart rate is shown in FIG. 17 as a percentage of the hypoxic baseline value over time.

Example 7—Measurement of Cyclic Adenosine Monophosphate (cAMP) Levels in CHO-K1 Cells in Response to 5-nonanyl-TR A cell based Chinese hamster ovary-K1 (CHO-K1) assay based on the GloSensor™ cAMP assay (Promega) was used as described above in Example 4 to characterize the effect of the following compounds on cAMP levels.

5-nonanyl-TR, i.e., the compound of Formula (A) wherein $R_2$=5-nonanyl

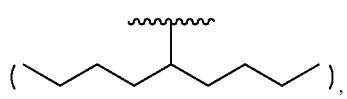

$C_{12}$-TR i.e., i.e., the compound of Formula (A) wherein $R_2$=$C_{12}$ alkyl

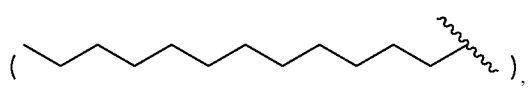

$C_{14}$-TR, i.e., the compound of Formula (A) wherein $R_2$=$C_{14}$ alkyl

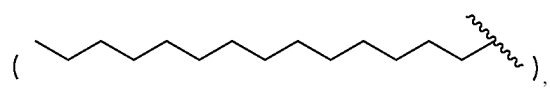

$C_{16}$-TR, i.e., the compound of Formula (A) wherein $R_2$=$C_{16}$ alkyl

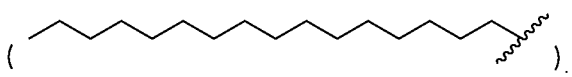

Figure 18:
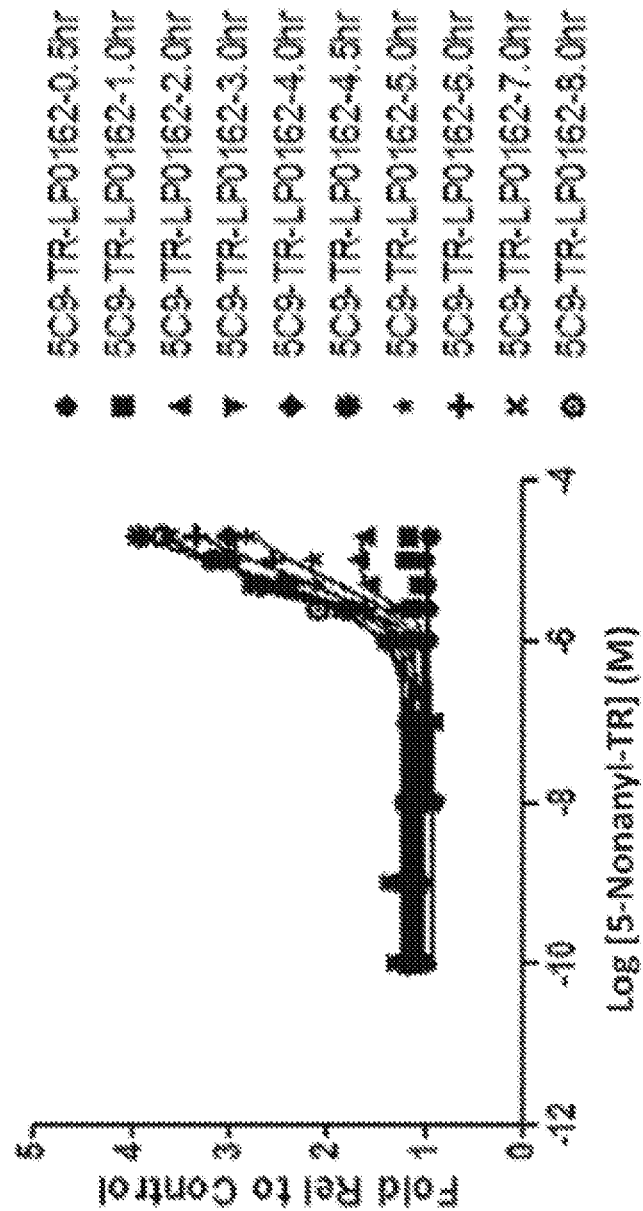
FIG. 18, top panel, is a graph of relative cAMP response of CHO-K1 cells as a function of 5C9-TR (5-nonanyl-treprostinil alkyl ester composition) challenge, at various dosages and time points.
Figure 19:
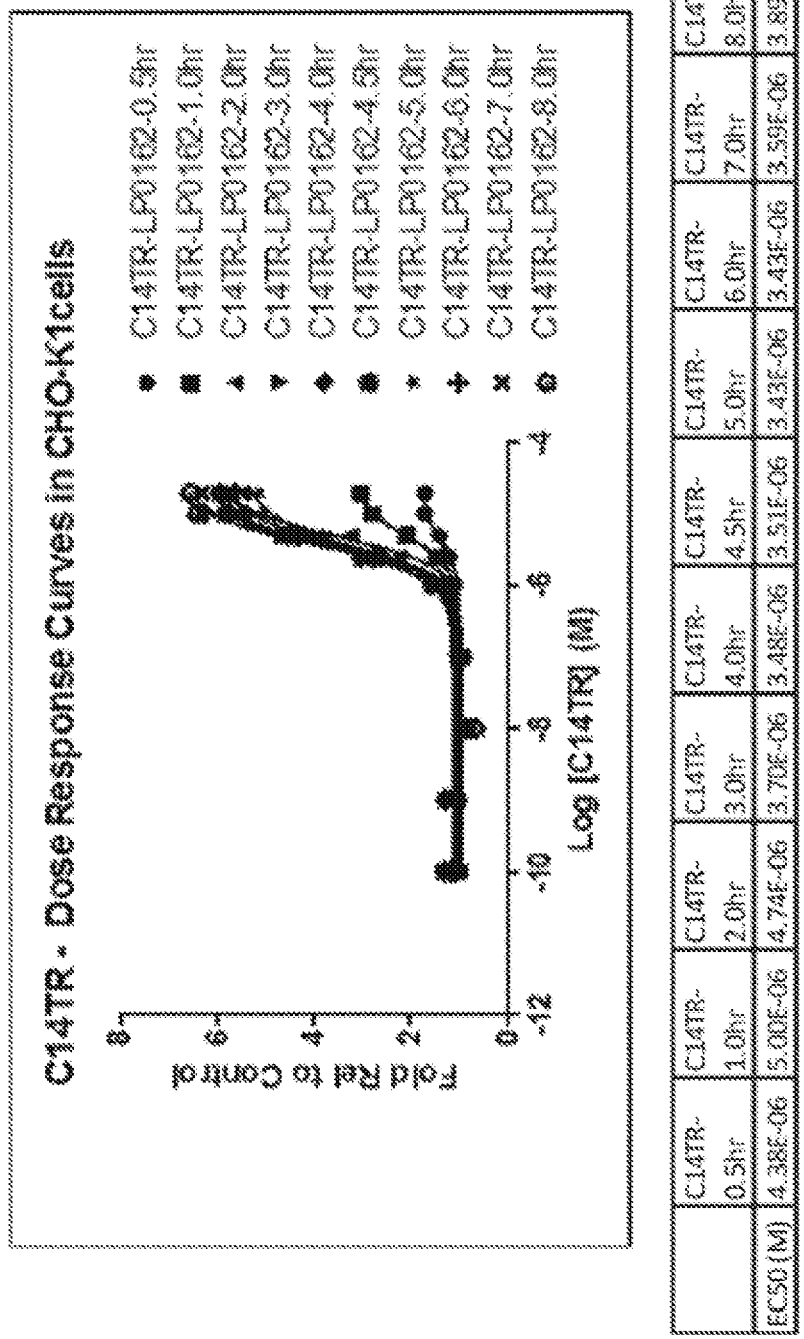
FIG. 19, top panel, is a graph of relative cAMP response of CHO-K1 cells vs. $C_{14}$-TR ($C_{14}$ treprostinil alkyl ester composition) challenge, at various dosages and time points.
Figure 20:
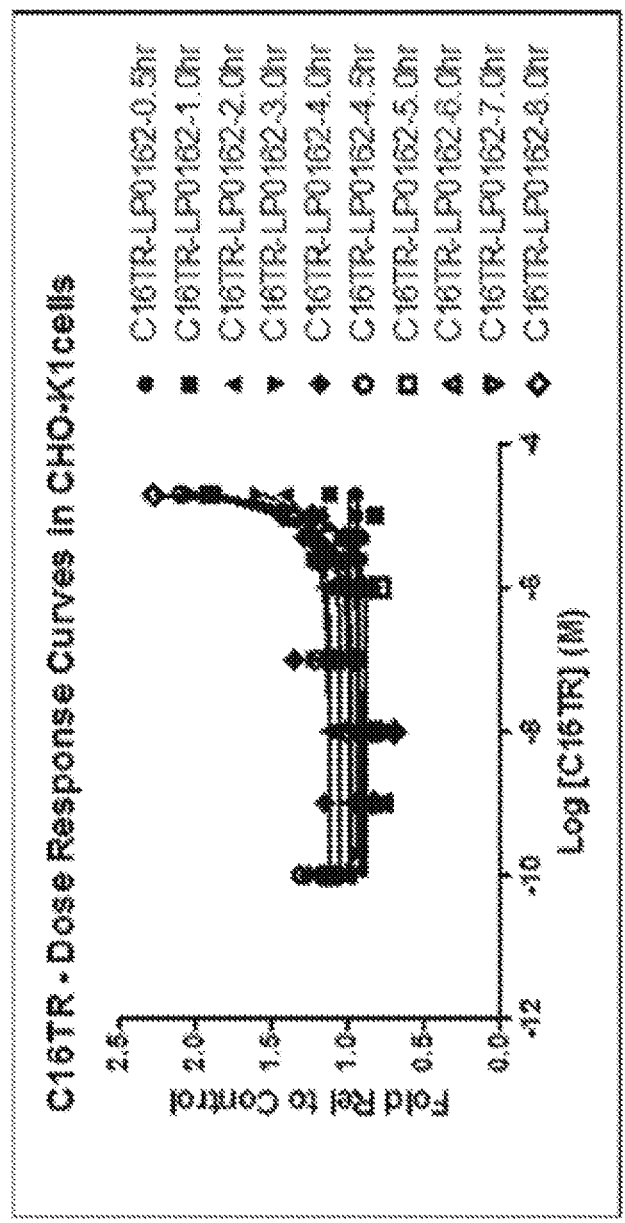
FIG. 20, top panel, is a graph of relative cAMP response of CHO-K1 cells vs. $C_{16}$-TR ($C_{16}$ treprostinil alkyl ester composition) challenge, at various dosages and time points.

CHO-K1 cells co-transfected with the EP2 receptor and GloSensor™ plasmid were challenged with 5-nonanyl-treprostinil (branched chain, 5C9-TR) or treprostinil alkyl ester compounds having either a $C_{12}$, $C_{14}$ or $C_{16}$ straight chain alkyl group at the $R_2$ position of the above compound. cAMP levels were then measured every 5 minutes over a time course of 8 hours. Dose response curves at 0.5 hr, 1 hr, 2 hr, 3 hr, 4 hr, 5 hr, 6 hr, 7 hr, and 8 hr incubation time for 5-nonanyl-TR, $C_{14}$-TR, and $C_{16}$-TR are provided in FIGS. 18, 19, and 20, respectively Like $C_{14}$-TR and $C_{16}$-TR, the potency of 5-nonanyl-TR increases with incubation time, indicating a delay-release profile. The half maximal effective concentrations ($EC_{50}$) of the treprostinil compounds were determined using the results from the cAMP assays. EC50 for 5-Nonanyl-TR, $C_{14}$-TR, and $C_{16}$-TR are shown in FIGS. 18, 19, and 20, respectively.

Figure 21:
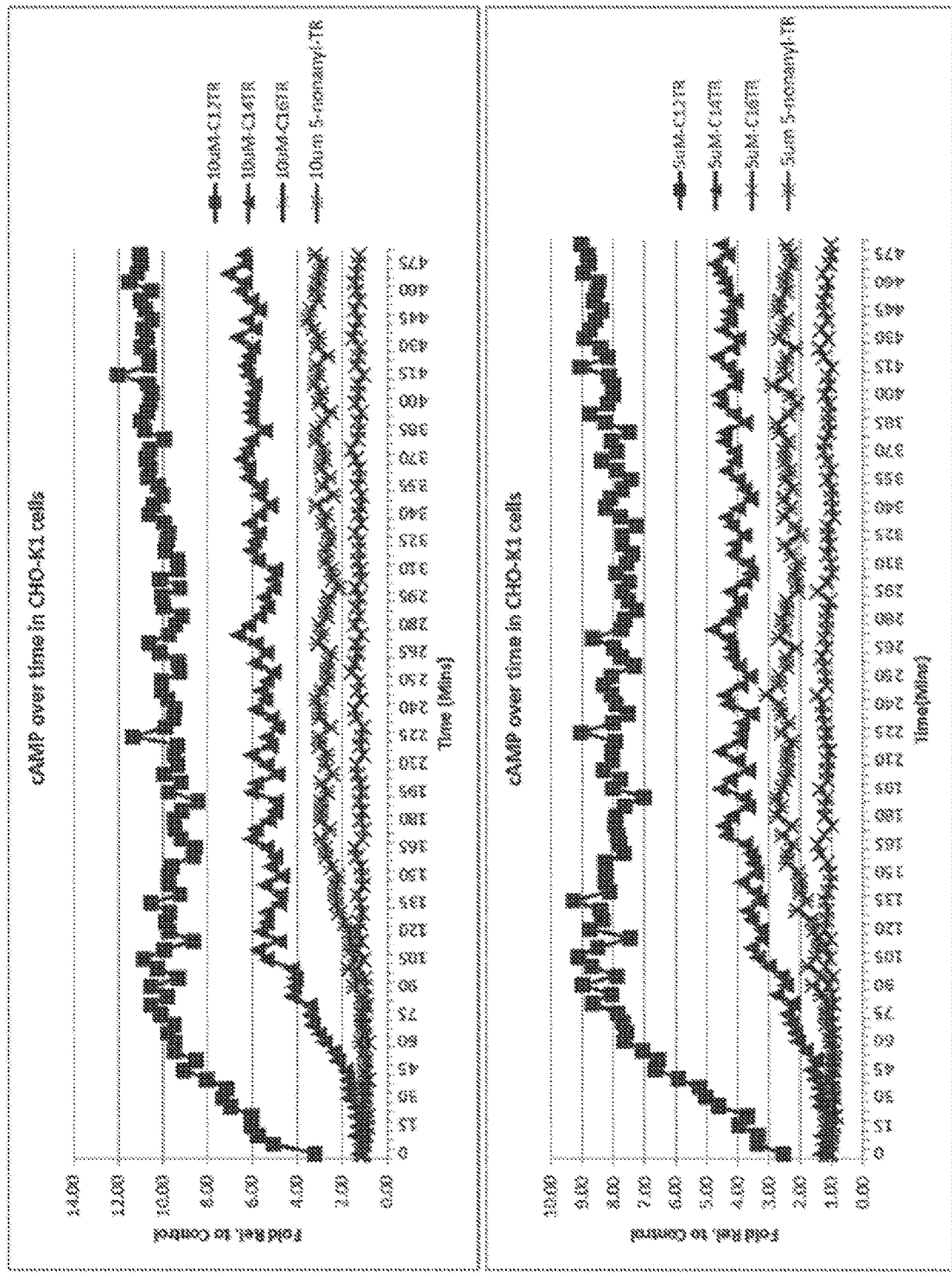
FIG. 21 are graphs of relative cAMP response of CHO-K1 cells vs. time, in response to challenge with $C_{12}$-TR, $C_{14}$-TR, $C_{16}$-TR, or 5-nonanyl-TR ($5C_9$-TR) at 10 µM (top panel) or 5 µM (bottom panel).

Kinetic profile results from the 10 µM (top panel) and 5 µM (bottom panel) concentrations of $C_{12}$-TR, $C_{14}$-TR, $C_{16}$-TR, or 5-nonanyl-TR are provided at FIG. 21. cAMP levels in response to $C_{12}$-TR, $C_{14}$-TR and 5-nonanyl-TR at both concentrations increased over the first 1-1.5 hours and were sustained for at least 8 hours. The ranking of activity of the treprostinil compounds was $C_{12}$-TR>$C_{14}$-TR>5-nonanyl-TR>$C_{16}$-TR.

The results of the study showed that like the treprostinil alkyl ester compounds having a $C_{12}$, $C_{14}$ or $C_{16}$ straight chain alkyl ester group, 5-nonanyl-TR, is functional and exhibits sustained cAMP activity. Thus, unlike free treprostinil (see Example 4), 5-nonanyl-TR has a delayed release profile.

Example 8—Comparison of Cyclic Adenosine Monophosphate (cAMP) Activation in CHO-K1 Cells in Response to $C_{14}$-TR Formulations A cell based Chinese hamster ovary-K1 (CHO-K1) assay based on the GloSensor™ cAMP assay (Promega) was used as described above in Example 4 to characterize the effect of different $C_{14}$-TR formulations on cAMP levels. The $C_{14}$-TR formulations are shown below in Table 12. Composition T679 does not comprise DOPC; composition T647 does not comprise DOPC or squalane.

The structure of $C_{14}$-TR is as follows:

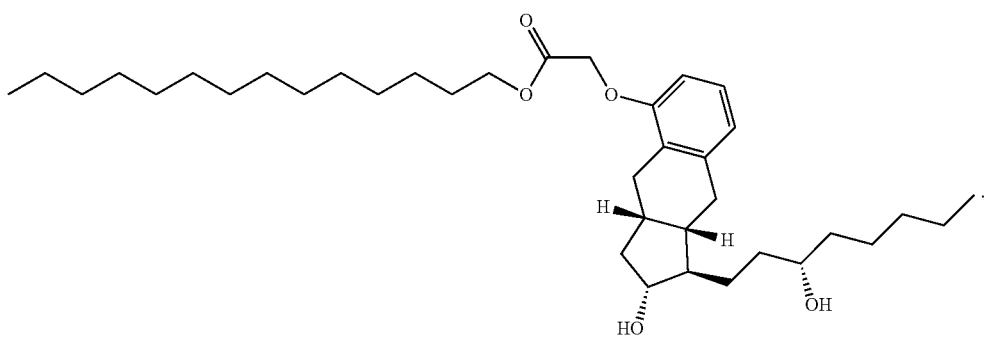 [SMILES: CCCCCCCCCCCCCCOC(=O)COc1cccc2c1C[C@H]1C[C@@H](O)[C@H](CC[C@@H](O)CCCCC)[C@H]1C2]

TABLE 12

Components of C14-TR formulations

| Composition | Cx-TR (mol %) | Hydrophobic Additive (mol %) | PEGylated lipid (mol %) | DOPC mol % |
|---|---|---|---|---|
| T631 | $C_{14}$-TR (40%) | Squalane (40%) | Chol-PEG2k (10%) | 10% |
| T679 | $C_{14}$-TR (45%) | Squalane (45%) | Chol-PEG2k (10%) | 0 |
| T647 | $C_{14}$-TR (90%) | (none) | Chol-PEG2k (10%) | 0 |

CHO-K1 cells co-transfected with the EP2 receptor and GloSensor™ plasmid were challenged with treprostinil alkyl ester formulations having a $C_{14}$ straight chain alkyl ester group at the carboxylic acid position and having the components as indicated in Table 12. cAMP levels were then measured every 5 minutes over a time course of 8 hours.

Figure 22:
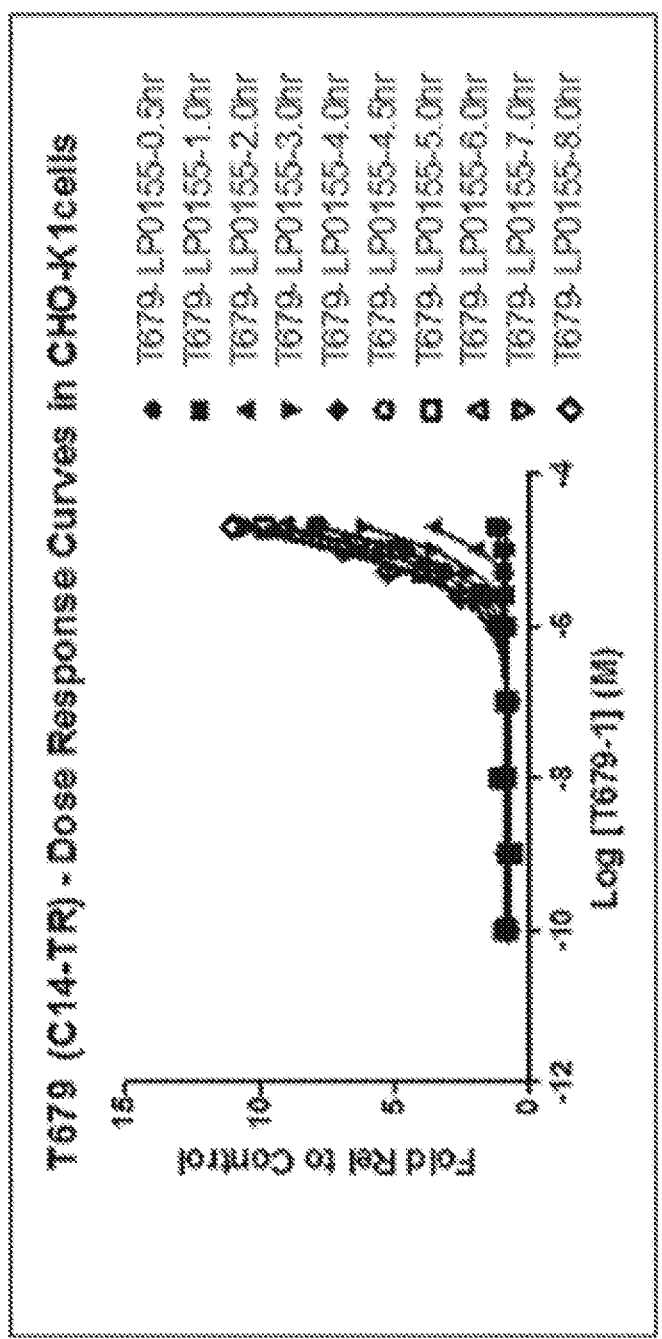
FIG. 22 (top panel) is a graph of relative cAMP response of CHO-K1 cells vs. T679 ($C_{14}$-TR 45 mol %, squalane 45 mol %, chol-PEG2k 10%) treprostinil alkyl ester composition challenge, at various dosages and time points FIG. 22 (bottom panel) shows the EC50 of T679 over time, calculated from the cAMP response of CHO-K1 cells vs. T679.

A dose response curve at 0.5 hr, 1 hr, 2 hr, 3 hr, 4 hr, 5 hr, 6 hr, 7 hr, and 8 hr incubation time for compound T679 is provided in FIG. 22. The potency of T679 increases over the incubation time, indicating a delay-release profile. The half maximal effective concentration ($EC_{50}$) of T679 was determined using the results from the cAMP assays, and is also shown in FIG. 22.

Kinetic profile comparisons for free treprostinil, T631, and T679 at 10 μM (top panel) and 5 μM (bottom panel) are shown in FIG. 23. Both T631 and T679 were less potent compared to free treprostinil. However, unlike free treprostinil, cAMP activation increased over time in response to both T631 and T679 and was sustained for at least 8 hours. The results of the study showed that the T679 formulation, which is a $C_{14}$-TR without DOPC, is functional and exhibits a delayed release profile similar to the profile of the $C_{14}$-TR T631.

A dose response curve at 0.5 hr, 1 hr, 2 hr, 3 hr, 4 hr, 5 hr, 6 hr, 7 hr, and 8 hr incubation time for compound T647 is provided in FIG. 24. Like T679, the potency of T647 increases over the incubation time, indicating a delay-release profile. The half maximal effective concentration ($EC_{50}$) of T647 was determined using the results from the cAMP assay, and is also shown in FIG. 24.

Kinetic profile comparisons for free treprostinil, T631, and T647 at 10 μM (top panel) and 5 μM (bottom panel) are shown in FIG. 25. Both T631 and T647 were less potent compared to free treprostinil. However, unlike free treprostinil, cAMP activation increased over time in response to both T631 and T647 and was sustained for at least 8 hours. The results of the study showed that the T647 formulation, which is a $C_{14}$-TR without DOPC or squalane, is functional and exhibits a delayed release profile similar to the profile of the $C_{14}$-TR T631.

Example 9—Functional cAMP Studies for Treprostinil Alkyl Ester Nanoparticle Formulations A cell based Chinese hamster ovary-K1 (CHO-K1) assay based on the GloSensor™ cAMP assay (Promega) was used as described above in Example 4 to characterize the effect of treprostinil compositions on cAMP levels. The cAMP profiles of the following treprostinil compositions were tested in this study (see also Table 13):

T555: $C_8$-TR (i.e., the compound of Formula (A) wherein

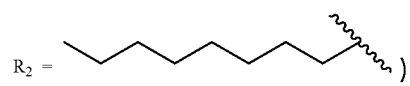

T556: $C_{10}$-TR (i.e., the compound of Formula (A) wherein

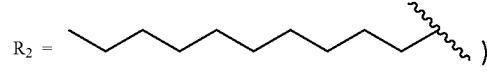

T568: $C_{12}$-TR (i.e., the compound of Formula (A) wherein

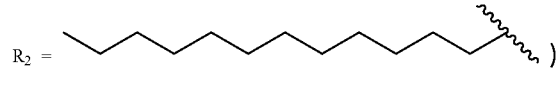

T631: $C_{14}$-TR (i.e., the compound of Formula (A) wherein $R_2 = $ ⟨structure⟩ )

T623: $C_{16}$-TR (i.e., the compound of Formula (A) wherein $R_2 = $ ⟨structure⟩ )

T637: $C_{18}$-TR (i.e., the compound of Formula (A) wherein $R_2 = $ ⟨structure⟩ )

TABLE 13

Treprostinil Alkyl ester formulations used in Example 9.

| Formulation No. | Treprostinil alkyl ester (Cx-TR*) | Treprostinil alkyl ester (mol %) | Squalane (mol %) | DOPC (mol %) | Chol-PEG2k (mol %) |
|---|---|---|---|---|---|
| T555 | $C_8$-TR | 40 | 40 | 10 | 10 |
| T556 | $C_{10}$-TR | 40 | 40 | 10 | 10 |
| T568 | $C_{12}$-TR | 40 | 40 | 10 | 10 |
| T631 | $C_{14}$-TR | 40 | 40 | 10 | 10 |
| T623 | $C_{16}$-TR | 40 | 40 | 10 | 10 |
| T637 | $C_{18}$-TR | 40 | 40 | 10 | 10 |

*Cx indicates alkyl chain length at position $R_2$ of the compound of Formula (A).

CHO-K1 cells co-transfected with the EP2 receptor and GloSensor™ plasmid were challenged with the treprostinil alkyl ester compositions listed above cAMP levels were then measured every 5 minutes over a time course of 8 hours.

A dose response curve at 0.5 hr, 1 hr, 2 hr, 3 hr, 4 hr, 5 hr, 6 hr, 7 hr, and 8 hr incubation time for composition T637 ($C_{18}$-TR) is provided in FIG. 26. The potency of T679 increases over the initial incubation time and then remains at a sustained level for at least 8 hours, indicating a delay-release profile. The half maximal effective concentration ($EC_{50}$) of T637 was determined using the results from the cAMP assays, and is also shown in FIG. 26.

Kinetic profile comparisons for free treprostinil, T555, T556, T568, T631, T623, and T637 at 10 μM (top panel) and 5 μM (bottom panel) are shown in FIG. 27. Each of the treprostinil alkyl ester compounds were less potent compared to free treprostinil. However, unlike free treprostinil, cAMP activation increased and then remained at a sustained level for at least 8 hours in response to each of the treprostinil alkyl ester compounds, indicating that each of these compounds is functional and exhibits a delayed release profile. The ranking order of activity for these compounds was T555/T556>T568>T631>T623>T637.

Example 10—Enzymatic Conversion Kinetics of Branched Treprostinil Compounds

A set of studies was conducted to determine the conversion kinetics to treprostinil of linear treprostinil compounds versus various branched treprostinil compounds. 0.4 mM of linear $C_8$-TR of branched treprostinil compounds 2-dimethyl-1-propanyl-TR, 3,3-dimethyl-1-butanyl-TR, 2-ethyl-1-butanyl-TR, 5-nonanyl-TR, or 3-pentanyl-TR (see below for structures) were incubated with 0.2 U esterase at 37° C. for 1 hour, and the conversion (% of total) was calculated at 0.25, 0.5, 0.75, or 1 hour incubation time.

$C_8$-TR (i.e., the compound of Formula (A) wherein $R_2 = $ ⟨structure⟩ )

2-dimethyl-1-propanyl-TR (i.e., the compound of Formula (A) wherein $R_2 = $ ⟨structure⟩ )

3,3-dimethyl-1-butanyl-TR (i.e., the compound of Formula (A) wherein $R_2 = $ ⟨structure⟩ )

2-ethyl-1-butanyl-TR (i.e., the compound of Formula (A) wherein $R_2 = $ ⟨structure⟩ )

5-nonanyl-TR (i.e., the compound of Formula (A) wherein $R_2 = $ ⟨structure⟩ )

3-pentanyl-TR (i.e., the compound of Formula (A) wherein $R_2 = $ ⟨structure⟩ )

FIG. 28 shows that 5-nonanyl-TR exhibited a slower conversion rate than linear C8-TR.

FIG. 29 shows the esterase mediated conversion of the following treprostinil compounds to treprostinil: $C_8$-TR, $C_9$-TR, $C_{10}$-TR, $C_{12}$-TR, $C_{14}$-TR and $C_{16}$-TR, i.e., where $R_2$ is as follows for the following formula. The conversion is relative to the $C_8$-TR compound and conversion was measured at 1 hr. post esterase incubation.

$C_8$-TR

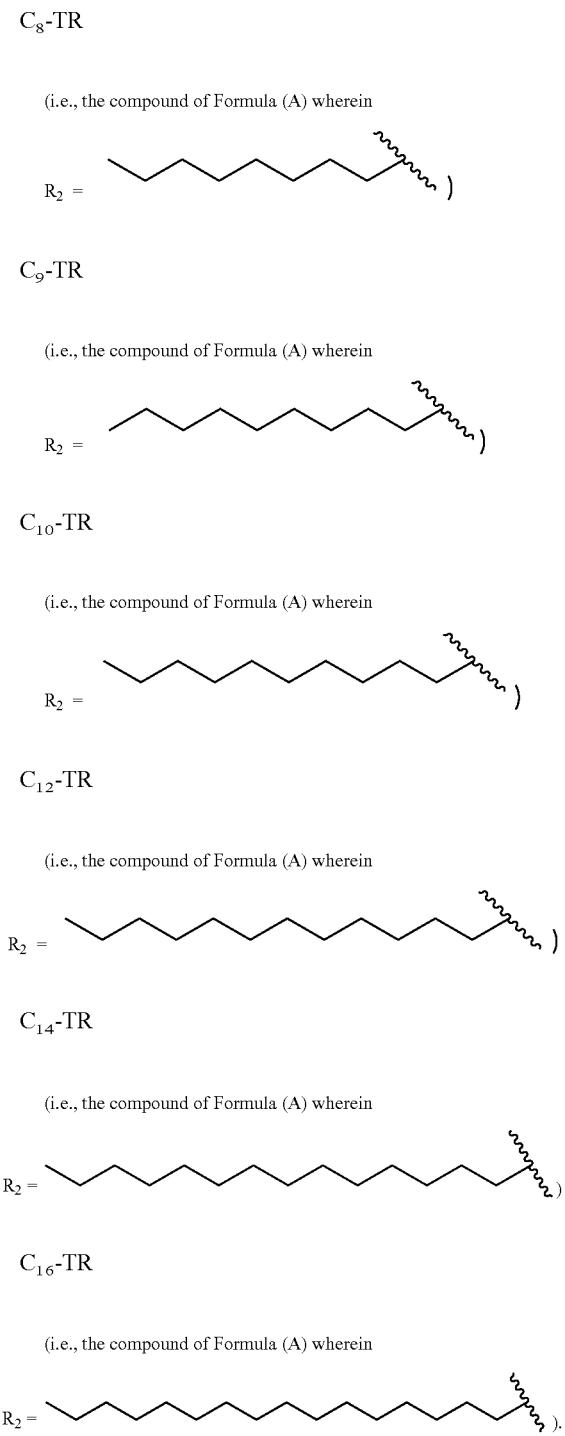

$C_9$-TR $C_{10}$-TR $C_{12}$-TR $C_{14}$-TR $C_{16}$-TR

FIG. 30 shows the esterase mediated conversion of branched treprostinil compounds (below) to treprostinil relative to esterase mediated conversion of $C_8$-TR to treprostinil. Conversion was measured at 1 hr. post esterase incubation.

$4C_7$-TR

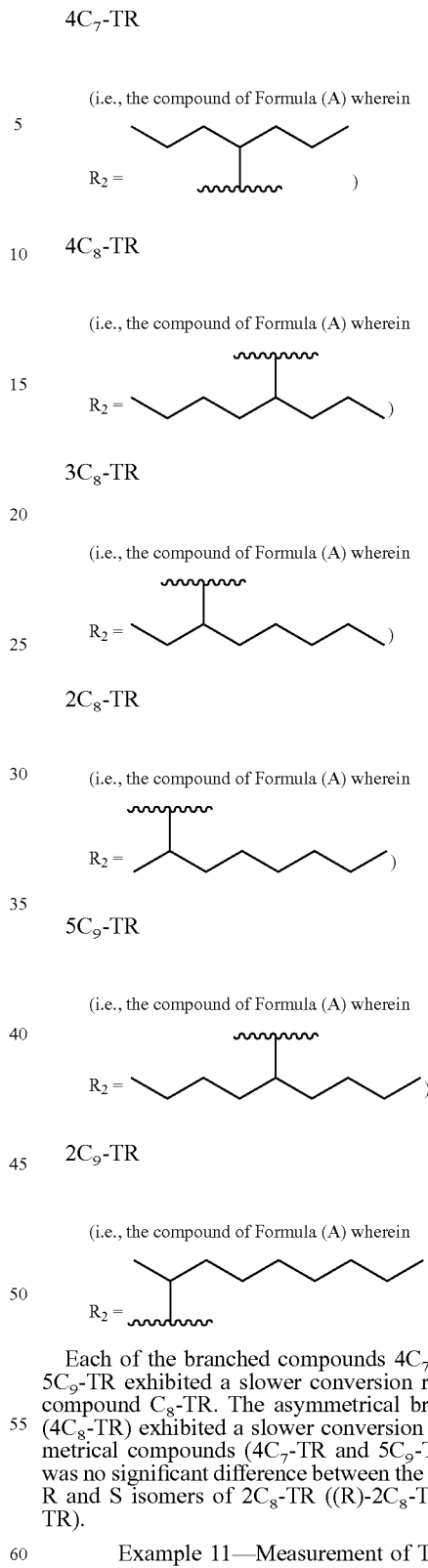

$4C_8$-TR $3C_8$-TR $2C_8$-TR $5C_9$-TR $2C_9$-TR

Each of the branched compounds $4C_7$-TR, $4C_8$-TR, and $5C_9$-TR exhibited a slower conversion rate than the linear compound $C_8$-TR. The asymmetrical branched compound ($4C_8$-TR) exhibited a slower conversion rate than the symmetrical compounds ($4C_7$-TR and $5C_9$-TR). Further, there was no significant difference between the conversion rates of R and S isomers of $2C_8$-TR ((R)-$2C_8$-TR versus (S)-$2C_8$-TR).

Example 11—Measurement of Treprostinil Pharmacokinetics in Rats

Table 14 provides the treprostinil alkyl ester formulations used in this study. The first three compositions (T568, T631 and T623) are believed to form lipid nanoparticles, while the last three compositions (T630, T635 and T636) are believed to form micelles.

TABLE 14

Alkyl ester formulations used in Example 11.

| Formulation No. | Treprostinil alkyl ester | Treprostinil alkyl ester (mol %) | Squalene (mol %) | DOPC (mol %) | Chol-PEG2K (mol %) | DMPE-Peg2K (mol %) |
|---|---|---|---|---|---|---|
| T568 | $C_{12}$-TR | 40 | 40 | 10 | 10 | — |
| T631 | $C_{14}$-TR | 40 | 40 | 10 | 10 | — |
| T623 | $C_{16}$-TR | 40 | 40 | 10 | 10 | — |
| T630 | $C_{12}$-TR | 10 | — | — | — | 90 |
| T635 | $C_{14}$-TR | 5 | — | — | — | 95 |
| T636 | $C_{16}$-TR | 5 | — | — | — | 95 |

T568 and T630: $C_{12}$-TR (i.e., the compound of Formula (A) wherein $R_2 = $ [structure]

T631 and T635: $C_{14}$-TR (i.e., the compound of Formula (A) wherein $R_2 = $ [structure]

T623 and T636: $C_{16}$-TR (i.e., the compound of Formula (A) wherein $R_2 = $ [structure]

Nebulized treprostinil (TRE) solution and treprostinil alkyl ester formulations were administered (at 15 nmol/kg, or 6 mg/kg TRE equivalent) to anaesthetised-ventilated rats (6-hour studies) or to conscious rats by nose-only inhalation (24-hour studies). Blood and lung samples were collected at specified time points. TRE and treprostinil alkyl ester concentrations in blood plasma and lung tissue were measured by HPLC/MS/MS analysis.

Anaesthetized, Ventilated Rats

Male Sprague Dawley rats were anaesthetised and prepared with endotracheal tube for ventilation. The right femoral vein was cannulated to facilitate blood collections. Terminal lung samples were taken for analysis only 6 hours after dosing. Aeroneb® nebulizer and a controller (Aerogen, Galway, Ireland) were used to produce aerosol of a mass median aerodynamic diameter (MMAD) between 2.5 µm and 4 µm and at a rate of 0.1 mL/min to provide an estimated pulmonary dose of 6 µg/kg. A SAR-830/AP Small Animal Ventilator (CWE Inc., Ardmore, Pa.) set up at ventilator tidal volume (VT) of 8 mL/kg, rate of 90 breaths/min, was used to deliver nebulized test articles of volume 250 µL. Systemic blood pressure (mSAP), heart rate (HR), and arterial oxygen saturation (SaO2). Physiologic parameters were measured during normoxia (fraction of inspired oxygen [$FrO_2$]=0.21, $SaO_2$≈90%) and for 2 to 3 hours during hypoxia ($FrO_2$=0.10, $SaO_2$≈50%).

Male Sprague Dawley rats were placed in restraining tubes and exposed to nebulised drugs via the Jaeger-NYU Nose-Only Directed-Flow Inhalation Exposure System (CH Technologies, Westwood, N.J.) (FIG. 31). Test articles (6 mL at specific concentration) were nebulised using the Aeroneb nebuliser to deliver a predetermined estimated pulmonary dose. Blood and lung tissue samples were taken at selected times after nebulization of the drugs over a 24-hour period.

Ventilated rats treated with nebulized TRE solution had the highest blood plasma concentration (Cmax) (3.5 ng/mL), which occurred immediately after dosing (FIG. 32, left). Measurable levels of TRE were not seen beyond 4 hours in the blood plasma and by 6 hours in the lungs. In contrast, ventilated rats treated with nebulized TPD-LNP had lower blood plasma TRE Cmax values, ranging from 0.2 ng/mL to 0.6 ng/mL (Table 15, FIG. 32, left). At 6 hours, treprostinil alkyl ester remained in the lung at levels that ranged from 100 ng/g to 400 ng/g tissue of TRE equivalent (FIG. 33). Treprostinil detected in the lung was speculated to be generated due to treprostinil alkyl ester hydrolysis during sample preparation. When dosing with micellar TPD, blood plasma levels of TRE were higher than with TPD lipid nanoparticle formulations, indicating that nanoparticles play an additional role in slow-release effect (FIG. 32, comparison of left and right graphs). In the 24-hour studies in rats dosed with TPD-lipid nanoparticle formulations (nose-only inhalation), TRE Cmax was higher than in ventilated animals and showed close to first-order exponential decline. Blood plasma concentrations of TRE in rats that received dosing with $C_{14}$- and $C_{16}$-treprostinil alkyl ester lipid nanoparticle formulations were maintained at greater than 0.1 ng/mL for up to 24 hours, (levels corresponding to activity in acute hypoxia studies) (FIG. 34, top). Lung levels of total TRE+TPD were approximately $10^3$ higher than plasma TRE and also exhibited exponential decline in rats administered treprostinil alkyl ester lipid nanoparticle formulations (FIG. 34, bottom). Table 16 further shows the pharmacokinetics of treprostinil in rats after dosing with the nose-only system with the nebulized treprostinil alkyl ester lipid nanoparticle formulations at the estimated pulmonary dose of 6 µg/kg. FIG. 35 further shows that release kinetics of treprostinil from inhaled $C_{16}$-TR formulations over 24 hours is independent of dose (nose only dosing). Time in FIG. 35 corresponds to the tune after beginning of nebulization of a 6 mL suspension (nebulization period was 30 min. to 60 min.). FIG. 38 shows that animals treated with T568 and T623 had a survival benefit (surviving beyond 200 minutes) compared with animals treated with free treprostinil or PBS). Specifically, FIG. 38 shows the pulmonary arterial pressure in animals treated with various lipid nanoparticle formulations, PBS and treprostinil. Furthermore, treatment with T568 and T623 showed little impact on systemic hemodynamics (FIG. 39). Finally, treprostinil alkyl ester nanoparticle formulations were shown to convert sloly to treprostinil, providing consistent blood plasma levels with reduced peak values (FIG. 40).

TABLE 15

Plasma pharmacokinetic of treprostinil in ventilated rats after dosing with nebulized treprostinil solution or formulated treprostinil alkyl ester suspension at an estimated pulmonary dose of 6 µg/kg

|  | Solution ($C_x$-TR) | Lipid Nanoparticles (T568, T631 and T623) | | | Micelles (T630, T635 and T636) | | |
| --- | --- | --- | --- | --- | --- | --- | --- |
|  |  | T568 ($C_{12}$-TR) | T631 ($C_{14}$-TR) | T623 ($C_{16}$-TR) | T630 ($C_{12}$-TR) | T635 ($C_{14}$-TR) | T636 ($C_{16}$-TR) |
| AUC 0-6 h (ng*h/mL) | 2.13 | 4.47 | 3.89 | 1.84 | 9.72 | 9.11 | 5.35 |
| Cmax (ng/mL) | 3.37 | 0.56 | 0.34 | 0.22 | 2.40 | 1.20 | 0.84 |
| Tmax (h) | 0.05 | 0.5 | 0.5 | 1.0 | 0.05 | 0.5 | 1.0 |

TABLE 16

Pharmacokinetics of treprostinil in rats after dosing with the nose-only system with the nebulized treprostinil alkyl ester formulations (T568, T631 and T623) at the estimated pulmonary dose of 6 µg/kg

| Compound | $C_{12}$-TR | $C_{14}$-TR | $C_{16}$-TR |
| --- | --- | --- | --- |
| immediately post dose (IPD) (µg/kg) | 6.2 | 10.4 | 17.9 |
| Lung apparent ellimination rate ($h^{-1}$) | 0.42 | 0.15 | 0.10 |
| Plasma maximum concentration (Cmax) IPD (ng/mL) | 4.03 | 4.93 | 3.46 |
| Plasma apparent ellimination rate ($h^{-1}$) | 0.30 | 0.18 | 0.14 |
| Area Under Curve (AUC) 1-24 (ng*h/mL) | 11.9 | 24.0 | 17.9 |

Inhaled TPDs are present in the lungs for an extended duration and are associated with a slow, sustained release of TRE into the blood. This duration of activity is increased with TPD formulated in lipid nanoparticles.

Example 12—Pharmacokinetic Profile of $C_{16}$-TR Alkyl Ester Lipid Nanoparticle Formulation in Dogs Twelve beagle dogs of either sex were randomly assigned to different inhaled doses of treprostinil in PBS or the compound of Formula (A) wherein $R_2 = $ (long alkyl chain structure)

($C_{16}$-TR) formulated in a lipid nanoparticle formulation (T623) that is suspended in PBS (see Table 14), with both given by nebulizer Formulations were nebulized with an Aeroneb nebulizer (MMAD: 2.5-4 µm) delivered into a 500 ml expansion chamber. Formulations were nebulized for 2 min at ventilator settings of 90 ml/breath, 15 breaths/min (delivered volume=2.7 L) and collected on a filter. Drug amount (µg) on the filter was measured by HPLC to calculate the concentration of drug delivered through the ventilator circuit (µg/L).

Dosimetry was performed in propofol-anesthetized dogs in which nebulized drugs were introduced into a mixing chamber interposed on the inspiratory limb of a canine respirator. Technical trials were performed before each experiment to measure the concentration of drug (µg/L) delivered for each breath. The inhaled drug dose (µg/kg) was calculated using the formula: Inhaled Drug Dose (µ/kg)= Drug Conc. (µg/L)×(µg/L)×Minute Ventilation (L/min.)× Time (min.)/Body Weight (kg). After delivery of the drugs, the dogs were disconnected from the respirator and blood samples were collected over a 72 h period to measure the treprostinil plasma concentrations by HPLC/MS/MS. Clinical signs were monitored over this 72 hr. period.

Use of the anesthetized, intubated and ventilated approach provided reproducibility between dogs to achieve the targeted inhaled dose for both treprostinil (5±1 and 16±2 µg/kg) and $C_{16}$-TR (7±1, 22±1, 46±1 and 95±1 µg/kg). At inhaled doses of 5 and 16 µg/kg, treprostinil plasma Cmax values for dogs dosed with treprostinil (2.7 and 5.9 ng/ml, respectively) were between 15-20 fold higher compared to treprostinil levels achieved upon dosing with similar inhaled doses (7 and 22 µg/kg) of $C_{16}$-TR in the T623 formulation (0.2 and 0.3 ng/mL, respectively) (FIG. 36). Furthermore, the plasma levels of treprostinil were sustained over a 48 hour period with inhalation of T623 but disappeared within a few hours following inhalation of treprostinil (FIG. 36). Coughing and rapid shallow breathing were absent during delivery of treprostinil to anesthetized, ventilated dogs but were present during the recovery period. Dogs receiving T623 showed no signs of respiratory irritation with inhaled doses as high as 46 µg/kg.

Comparison of $C_{16}$ Alkyl Ester Lipid Nanoparticle Treprostinil Formulation to $C_{12}$ and $C_{14}$ Alkyl Ester Lipid Nanoparticle Treprostinil Formulations Twelve beagle dogs were exposed to inhaled treprostinil and three treprostinil alkyl ester lipid nanoparticle formulations T568 (dodecyl-treprostinil, $C_{12}$-TR), T631 (tetradecyl-treprostinil, $C_{14}$-TR) and T623 (hexadecyl-treprostinil, $C_{16}$-TR). The components of each formulation are provided in Table 14, above.

Dosimetry was performed in propofol-anesthetized, artificially ventilated dogs in which nebulized drugs were introduced into a mixing chamber interposed on the inspiratory limb of the respirator. Technical trials were performed before each experiment measuring the concentration of drug (μg/L) per breath, minute ventilation and time required to achieve a targeted pulmonary dose. After recovery from the anesthesia, blood samples were collected over 72 h and plasma levels of TRF measured by HPLC/MS/MS. Clinical signs (cough, rapid shallow breathing, emesis and pale gums) were also monitored.

At a targeted pulmonary dose of 18 μg/kg, plasma levels of treprostinil were highest for free treprostinil (Cmax=5.9±0.6 ng/ml) immediately alter dosing but corresponding Cmax values for $C_{12}$-TR, $C_{14}$-TR and $C_{16}$-TR were 5-, 13- and 20-fold lower. Plasma treprostinil was below the level of quantification by 4 h after inhaled free treprostinil, but was sustained for 48-72 h after inhaled treprostinil alkyl ester formulations.

Dose-dependent increases in Cmax and AUC were seen with inhaled $C_{16}$-TR (6-90 μg/kg) with a prolonged presence of treprostinil in the plasma for up to 72 h at higher doses. Adverse clinical signs were seen with free treprostinil and $C_{12}$-TR at a targeted dose of 18 μg/kg, but not with $C_{14}$-TR and $C_{16}$-TR. In the dose-response study with $C_{16}$-TR, adverse clinical signs were seen in only 1 dog at a targeted pulmonary dose of 90 μg/kg.

Based upon this PK study in dogs, inhaled $C_{16}$-TR in a nanoparticle formulation provides sustained presence of treprostinil in the plasma and lower side effect potential than inhaled free treprostinil at comparable doses.

Example 13—Characterization of a Lipid Nanoparticle $C_{16}$ Alkyl Ester Treprostinil Formulation T748, a lipid nanoparticle $C_{16}$ alkyl ester treprostinil formulation having the following components, was characterized.

| $C_{16}$-TR (mol %) | Squalane (mol %) | DSPE-PEG2k (mol %) |
| --- | --- | --- |
| 45 | 45 | 10 |

Assessment of the Tolerability and Pharmacokinetics (PK) of Treprostinil in Rats administered T748 lipid nanoparticle formulation To assess whether repealed dosing with inhaled $C_{16}$-TR is well tolerated and alters PK, rats were exposed to $C_{16}$-TR for 14-consecutive days.

5 groups (n=4 per group) of Sprague Dawley rats were exposed to inhaled phosphate buffered saline (PBS) or 4 doses of $C_{16}$-TR (0.6, 1.8, 6 and 18 μg/kg) given by nebulization in a nose-only inhalation chamber. Cohorts of rats were studied after 1, 7 and 14 daily inhaled doses of $C_{16}$-TR and blood samples were collected at 1, 3, 6 and 24 hr., and lungs harvested at 24 hr. after the last dose of the drug. Concentrations of treprostinil and $C_{16}$-TR in the plasma and lungs were measured by HPLC/MS/MS. Body weights were recorded daily and organ weights (lungs, heart, liver) were measured 24 hr. after the last drug dose.

There were no tolerability issues or significant changes (relative to PBS) in body weights and organ weights after inhalation of $C_{16}$-TR for 14-consecutive days. Increasing inhaled doses of $C_{16}$-TR (0.6-18 μg/kg) increased the plasma $C_{max}$ and AUC but this was not consistently affected upon repeated dosing. There was some variability in AUC between days 1 and 14 within the different dosing groups with 2 of the 4 doses (1.8 and 18 μg/kg) showing no difference, and the other 2 doses (0.6 and 6 μg/kg) showing a 3- to 4-fold increase in AUC by day 14. The presence of $C_{16}$-TR was not detected in the plasma at any dose. However, relatively high concentrations of $C_{16}$-TR (approximately 1,000-fold higher than plasma treprostinil) were found in the lungs. Inhaled $C_{16}$-TR produced a dose-dependent increase in the concentration of $C_{16}$-TR in the lungs, but this was not changed by repeated dosing for 14-consecutive days.

Inhaled $C_{16}$-TR (0.6-18 μg/kg) was well tolerated with no evidence of body weight and organ weight change after dosing for 14 consecutive days.

Effect of $C_{16}$ Alkyl Ester Lipid Nanoparticle Treprostinil Formulation on the Cough Reflex in Guinea Pigs In this study, the tussive effects of inhaled treprostinil and a lipid nanoparticle formulation of the alkyl ester hexadecyl-treprostinil ($C_{16}$-TR), were studied in guinea pigs.

Three groups of male Dunkin Hartley guinea pigs were placed in a whole body plethysmograph and exposed to aerosolized phosphate buffered saline (PBS), TRE (1-300 μg/ml) and $C_{16}$-TR lipid nanoparticle formulation T748 (30 μg/ml), respectively. T623 has the following components:

Aerosols were generated with an Ultra-Neb Pro nebulizer (nebulizer output 0.36 mL/min.) that was mixed with inspired air delivered at a rate of 2 L/min. The PBS or drugs were delivered for 10 min. and the number of coughs recorded during and for 20 min. after the delivery. Coughs were detected by visual observations, plethysmograph recordings and cough sounds.

Exposure to aerosolized PBS did not induce cough. TRE exposure did not consistently evoke cough in the animals tested until the exposure concentration was equal to or greater than 30 μg/mL. The cough response was characterized by bouts of high frequency cough with lowered cough sounds compared to the typical cough sound induced by citric acid or capsaicin. TRE at a nebulized concentration of 30 μg/mL produced consistent cough in 7 of 7 guinea pigs with 1-4 cough bouts and a total number of coughs averaging 36±9 coughs. In contrast, inhaled $C_{16}$-TR lipid nanoparticle formulation at a nebulized concentration of 30 μg/mL did not induce cough, no events, in 6 of 6 guinea pigs.

The results in this study demonstrate that inhaled TRE induces cough in guinea pigs, the profile of which is somewhat similar to that previously described (Type II coughs) with inhaled prostaglandins in guinea pigs (Maher and Belvisi, 2010). On the other hand, inhaled $C_{16}$-TR lipid nanoparticle formulation, did not induce cough and suggests that this formulation may eliminate some of the local adverse side effects such as cough seen with inhaled TRE therapy in humans.

Example 14—Acylation of Treprostinil Derivatives

Treprostinil or treprostinil ester derivatives (e.g., derivatized with alkyl or alkenyl groups at the carboxylic acid moiety as prepared in Example 1) are acylated as follows.

The compound of Example 1 (0.05 mol) or treprostinil is dissolved in 10 mL of dichloromethane at 0° C. Dimethylaminopyridine is added (20 mol %), and then a solution of an acyl chloride R(CO)Cl (2.1 equivalents) at 0° C. (wherein R is $R_5$ or $R_6$ as described herein) is added to the compound of Example 1 or treprostinil. The solution is allowed to stir and warm to 23° C. over 1 hour. The reaction is monitored by thin layer chromatography, and when no further change is observed, the reaction is quenched with $NaHCO_3$ (sat), and the quenched mixture is extracted with dichloromethane (3×10 mL). The combined organic extracts are dried over anhydrous sodium sulfate, and the solvent is removed under vacuum to afford the crude product. Purification is effected by column chromatography on silica gel with 2% methanol in dichloromethane.

A general scheme for synthesis of the acylated treprostinil-derivatives is shown below ($R_2$ is described herein, for example as H or a linear or branched alkyl group):

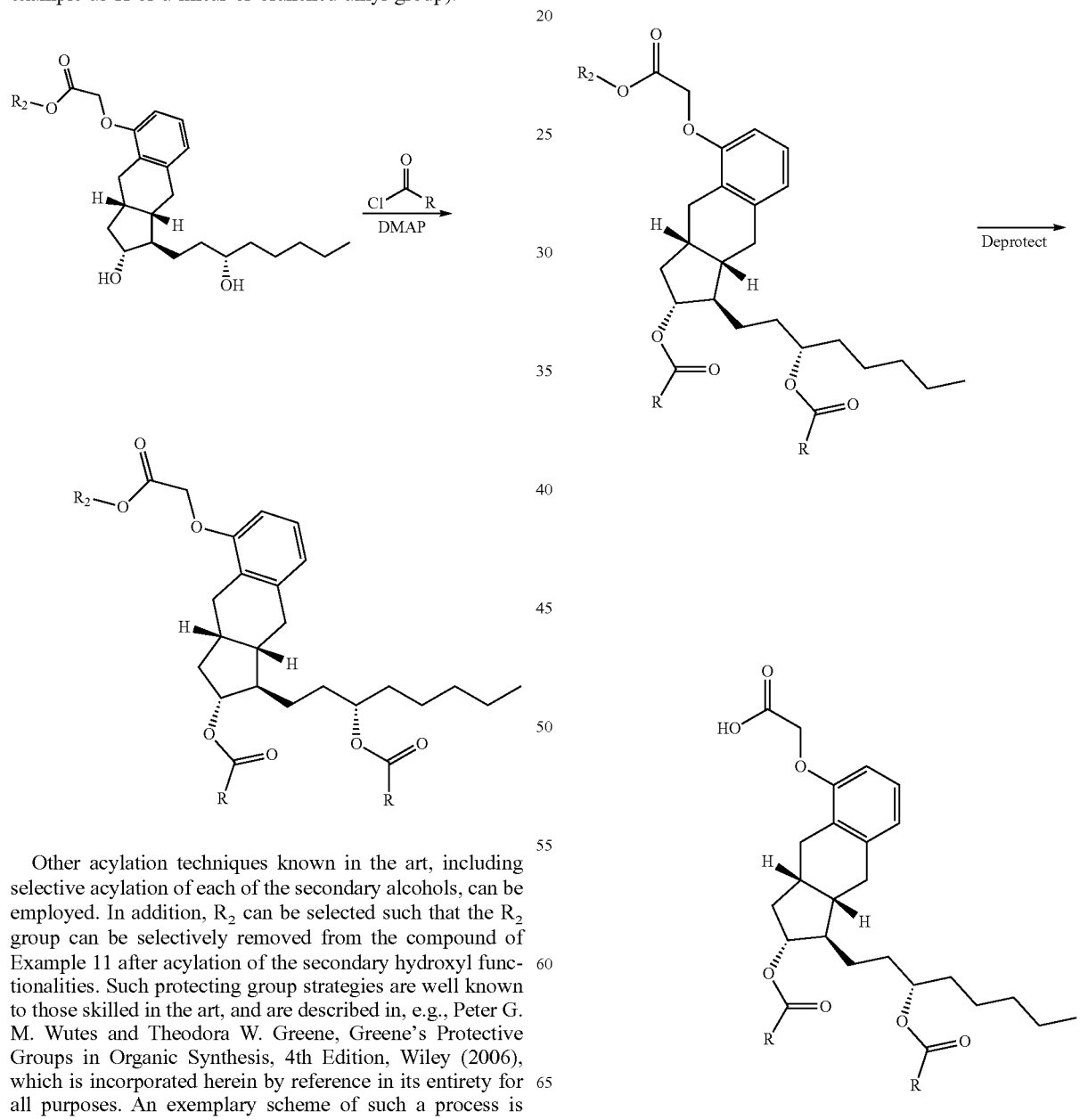

Other acylation techniques known in the art, including selective acylation of each of the secondary alcohols, can be employed. In addition, $R_2$ can be selected such that the $R_2$ group can be selectively removed from the compound of Example 11 after acylation of the secondary hydroxyl functionalities. Such protecting group strategies are well known to those skilled in the art, and are described in, e.g., Peter G. M. Wutes and Theodora W. Greene, Greene's Protective Groups in Organic Synthesis, 4th Edition, Wiley (2006), which is incorporated herein by reference in its entirety for all purposes. An exemplary scheme of such a process is shown below:

Synthesis of $C_{16}$TR-OAc:

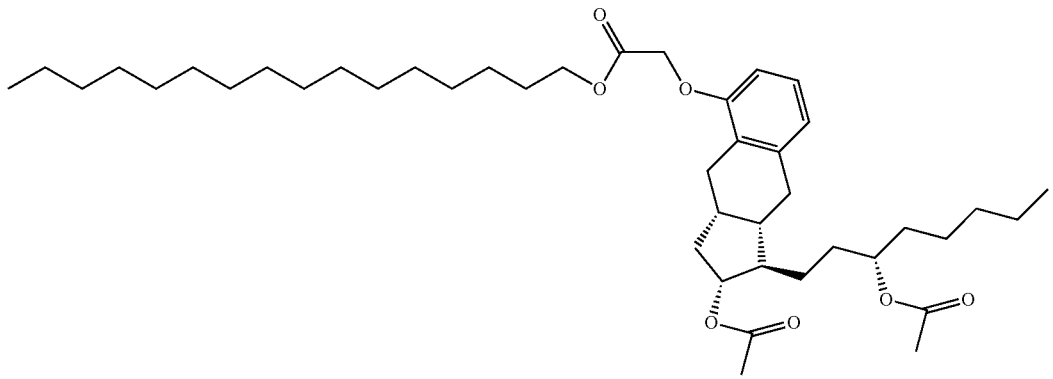 [SMILES: CCCCCCCCCCCCCCCCOC(=O)COc1cccc2c1C[C@H]1C[C@@H](OC(C)=O)[C@H](CC[C@H](CCCCC)OC(C)=O)[C@H]1C2]

To a solution of (1R,2R,3aS,9aS)-[[2,3,3a,4,9,9a-hexahydro-2-hydroxy-1-[(3S)-3-hydroxyoctyl]-1H-benz[f]inden-5-yl]oxy]acetic acid (treprostinil) (78.1 mg, 200 μmoles) dissolved in 1,4-Dioxane (2.0 mL) was added triethylamine (TEA) (98 μL, 700 μmoles, 3.5 equivalents), acetic anhydride (166 μL, 1,760 μmoles, 8.8 equivalents), and a catalytic amount of dimethylaminopyridine (DMAP). The reaction mixture was allowed to shake at 40° C. for 72 hours. Solvent was removed under reduced pressure to yield a thick colorless oil. The crude material was dissolved in hexanes and washed with a solution of saturated $NaHCO_3$ (3×5 mL). The organic layers were combined and solvent was removed using a gentle stream of warmed $N_2$ gas and gentle heat to yield a thick colorless oil. The crude material was dissolved in 20% "PrOH/Hexanes, passed through a 0.45 μm syringe filter, and submitted to preparatory HPLC purification. Solvent was removed from the purified material using a gentle stream of warmed $N_2$ gas and gentle heat to yield a thick colorless oil. The pure material was suspended in ethyl lactate for storage and was submitted to analytical HPLC for concentration determination.

$C_{16}$-TR-OAc: 73% overall yield. The compound was also characterized by NMR spectroscopy:

$^1$H NMR (500 MHz, $CDCl_3$) δ 0.89 (t, J=7.0 Hz, 6H), 1.17-1.32 (m, 33H), 1.43-1.46 (m, 2H), 1.49-1.66 (m, 8H), 1.89-1.93 (m, 1H), 1.99 (s, 3H), 2.06 (s, 3H), 2.30-2.35 (m, 2h), 2.47 (d of d, J=14.5 Hz, J=6.0 Hz, 1H), 2.55 (d of d, J=15.0 Hz, J=6.0 Hz, 1H), 2.76 (d, of d, J=14.5 Hz, J=6.0 Hz, 1H), 2.90 (d of d, J=15.0 Hz, J=6.0 Hz, 1H), 4.19 (t, J=7.0 Hz, 2H), 4.62 (s, 2H), 4.70-4.74 (m, 1H), 4.87 (p, J=6.0 Hz, 1H), 6.63 (d, J=8.0 Hz, 1H), 6.82 (d, J=8.0 Hz, 1H), 7.08 (t, J=8.0 Hz, 1H), ppm; $^{13}$C NMR (125 MHz, $CDCl_3$) δ 14.2, 14.3, 21.5 (2), 22.7, 22.9, 25.1, 26.0 (2), 28.3, 28.8, 29.4, 29.6, 29.7, 29.8, 29.9, 31.9, 32.1, 33.6, 33.7, 34.3, 37.8, 40.7, 49.0, 65.6, 66.2, 74.6, 79.0, 109.8, 121.8, 126.4, 127.6, 140.7, 155.1, 169.6, 171.0, 171.1 ppm.

Example 15—Synthesis of Treprostinil Amide Derivatives

Treprostinil is available commercially, and can be synthesized, for example, by the methods disclosed in U.S. Pat. Nos. 6,765,117 and 8,497,393. Synthesis of prostaglandin derivatives is described in U.S. Pat. No. 4,668,814. The disclosures of U.S. Pat. Nos. 6,765,117; 8,497,393 and 4,668,814 are each incorporated by reference in their entireties for all purposes.

To a solution of (1R,2R,3aS,9aS)-[[2,3,3a,4,9,9a-hexahydro-2-hydroxy-1-[(3S)-3-hydroxyoctyl]-1H-benz[f]inden-5-yl]oxy]acetic acid (i.e., treprostinil) (78.1 mg, 200 μmoles) dissolved in 1,4-Dioxane (2.0 mL) was added triethylamine (TEA) (98 μL, 700 μmoles, 3.5 equivalents), alkylamine $R_1$—$NH_2$ (240 μmoles, 1.2 equivalents), and a solution of PyBOP (364 mg, 700 μmoles, 3.5 equivalents) dissolved in 2.0 mL MeCN (acetonitrile).

The reaction mixture was heated to 40° C. and allowed to shake at approximately 100 rpm overnight. Solvent was removed under reduced pressure to yield the crude product as a thick yellow oil. The product was extracted (l-l extraction) from the oil by repeated washings with 20% "PrOH/Hexanes (3×3 mL). Solvent was removed from the organic extract using a gentle stream of warmed $N_2$ gas and gentle heat to yield a thick, slightly yellow oil. The crude material was dissolved in 20% "PrOH/Hexanes, parsed through a 0.45 μm syringe filter, and submitted to preparatory HPLC purification. Solvent was removed from the purified material using a gentle stream of warmed $N_2$ gas and gentle heat to yield a thick, colorless oil. The pure material was suspended in ethyl lactate for storage and was submitted to analytical HPLC for concentration determination.

The following treprostinil amide derivatives of Formula B were made by the synthesis scheme provided above (Table 17) Percentage yield is also provided in parentheses.

Formula (B)

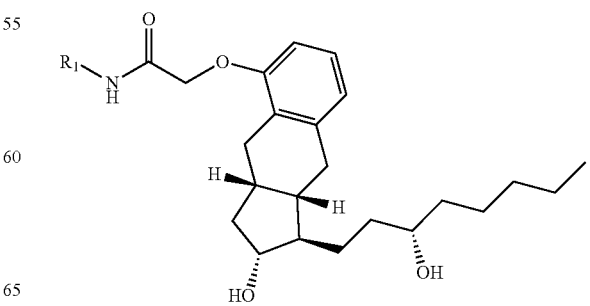

TABLE 17
Treprostinil amide derivatives
| R₁ group | Yield | Compound abbreviation |
|---|---|---|
| R₁ = 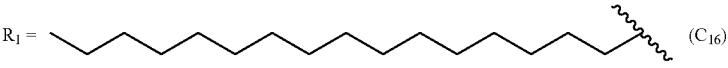 (C₁₆) | 88% | C₁₆-TR-A |
| R₁ = 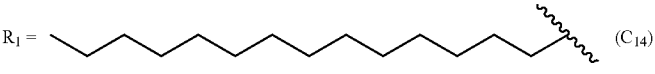 (C₁₄) | 71% | C₁₄-TR-A |
| R₁ = 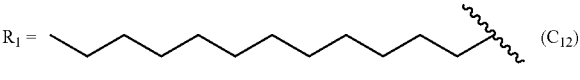 (C₁₂) | 57% | C₁₂-TR-A |
| R₁ = 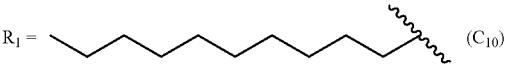 (C₁₀) | 62% | C₁₀-TR-A |
| R₁ = 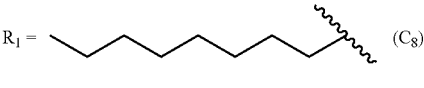 (C₈) | 47% | C₈-TR-A |
| R₁ = 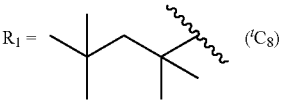 (ᵗC₈) | 72% | ᵗC₈-TR-A |
| R₁ = 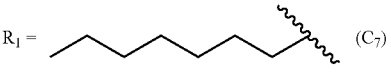 (C₇) | 50% | C₇-TR-A |
| R₁ = 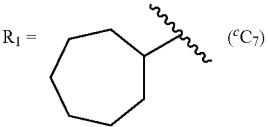 (ᶜC₇) | 62% | ᶜC₇-TR-A |
| R₁ = 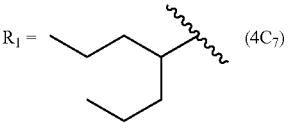 (4C₇) | 65% | 4C₇-TR-A |
| R₁ = 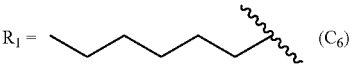 (C₆) | 58% | C₆-TR-A |
| R₁ = 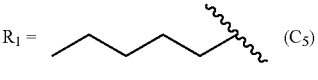 (C₅) | 77% | C₅-TR-A |
| R₁ = 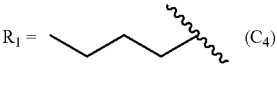 (C₄) | 28% | C₄-TR-A |
| R₁ = 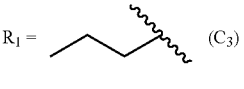 (C₃) | 12% | C₃-TR-A |
| R₁ = 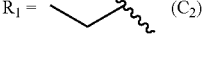 (C₂) | 12% | C₂-TR-A |

TABLE 17-continued

Treprostinil amide derivatives

| $R_1$ group | Yield | Compound abbreviation |
|---|---|---|
| 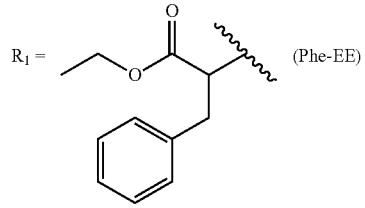 $R_1 =$ (Phe-EE) | 60% | Phe-EE-TR-A |
| 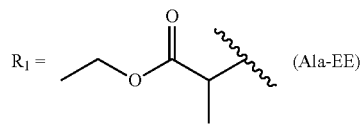 $R_1 =$ (Ala-EE) | Not determined | Ala-EE-TR-A |
| 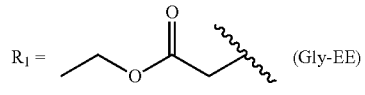 $R_1 =$ (Gly-EE) | Not determined | Gly-EE-TR-A |
| 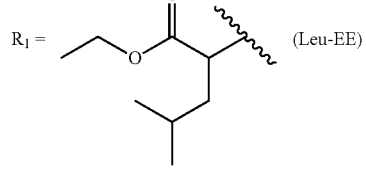 $R_1 =$ (Leu-EE) | Not determined | Leu-EE-TR-A |

$C_6$-TR-A and $C_2$-TR-A were characterized by NMR spectroscopy.

NMR Characterization of C6-TR-A $^1$H NMR (500 MHz, CDCl$_3$) δ 0.90 (q, J=7.0 Hz, 6H), 1.17 (q, J=12.0 Hz, 1H), 1.30-170 (m, 18H), 1.81-1.83 (m, 1H), 1.80-1.93 (m, 1H), 2.20 (p, J=6.0 Hz, 1H), 2.22-2.23 (m, 1H), 2.47-2.54 (m, 2H), 2.75-2.82 (m, 2H), 3.16 (sextet, J=4.0 Hz, 1H), 3.35 (q, J=7.0 Hz, 2H), 3.63 (s, 1H), 3.70-3.80 (m, 1H), 4.48 (s, 2H), 6.55 (s, 1H), 6.70 (d, J=7.5 Hz, 1H), 6.85 (d, J=7.5 Hz, 1H), 7.11 (t, J=7.5 Hz, 1H) ppm, $^{13}$C NMR (125 MHz, CDCl$_3$) δ 14.2, 14.3, 22.8, 22.9, 25.6, 26.4, 26.7(2), 28.8, 29.7, 31.6, 32.1, 33.0, 33.8, 35.1, 37.7, 39.2, 41.4, 41.6, 46.5, 52.4, 68.4, 72.8, 110.4, 122.2, 126.8, 127.3, 141.2, 154.5, 168.7 ppm; HRMS (ESI, 2:2:1 MeCN, MeOH, H$_2$O): m/z=474.35717 ([M+H]$^+$).

NMR Characterization of C12-TR-A

HRMS (ESI, 2:2:1 MeCN, MeOH, H$_2$O): m/z=558.45099 ([M+H]$^+$).

Example 16—Treprostinil Amide Derivative Solubility in Hydrofluoroalkane Propellants Selected treprostinil derivatives were evaluated for the use in a metered dose inhaler (MDI). Four ester derivatives, dodecyl-treprostinil (C$_{12}$-TR), tetradecyl-treprostinil (C$_{14}$-TR), hexadecyl-treprostinil (C$_{16}$-TR), and the branched chain nonanyl-treprostinil (5C9-TR), and two amide derivatives, C$_{16}$-TR-A and C$_{12}$-TR-A (see Table 17) were tested for solubility in hydrofluoroalkane propellants HFA-134a and HFA-227 with added ethanol.

5 mg of each treprostinil compound was added in a glass bottle. Specific amount of ethanol was added by weight. An MDI valve was crimped to each bottle, and HFA propellant added through the valve to the total volume of 5 mL. Compounds were allowed to dissolve for 24 hours at room temperature. The formulations were assessed visually for solubility. The goal was to estimate the minimum ethanol concentration required to solubilize each compound in propellant.

Soluble samples presented as clear and colorless solutions. Less than soluble samples had a thin liquid-vapor ring of various density visible on the bottle surface at the liquid-vapor interface. Non-soluble samples had white precipitate or crystals formed. Ethanol was added as a solubility aid. As it can be seen from the solubility tables below (Table 18 and Table 19), compounds that were not soluble at 3% added ethanol became soluble at 10 or 13% added ethanol.

TABLE 18

Solubility chart of treprostinil prodrugs in HFA-134a with added ethanol.

| HFA-134a | C$_{12}$-TR | C$_{14}$-TR | C$_{16}$-TR | 5C$_9$-TR | C$_6$-TR-A | C$_{12}$-TR-A |
|---|---|---|---|---|---|---|
| 13% EtOH | S | S | R | S | n/e | n/e |
| 10% EtOH | S | S | R | R | S | S |
| 7% EtOH | S | R | R | R | R | R |
| 5% EtOH | R | R | R | R | R | R |
| 3% EtOH | R | R | n/e | R | R | P |

S—soluble; R—thin liquid-vapor ring is visible; P—precipitate is visible; n/e—not evaluated.

TABLE 19

Solubility chart of treprostinil derivatives in HFA-227 with added ethanol.

| HFA-227 | $C_{12}$-TR | $C_{14}$-TR | $C_{16}$-TR | $5C_9$-TR | $C_6$-TR-A | $C_{12}$-TR-A |
|---|---|---|---|---|---|---|
| 13% EtOH | S | n/e | S | S | n/e | n/e |
| 10% EtOH | n/e | R | n/e | n/e | n/e | S |
| 7% EtOH | n/e | R | R | R | R | R |
| 5% EtOH | n/e | n/e | R | n/e | R | R |
| 3% EtOH | R | R | n/e | R | R | P |

S—soluble; R—thin liquid-vapor ring is visible; P—precipitate is visible; n/e—not evaluated.

Example 17—Pharmacokinetis of Blood Plasma Treprostinil After Inhalation of $C_{12}$ Amide Linked Treprostinil Nanoparticle Formulation in Ventilated Rats Male Sprague Dawley rats (N=3) were anesthetized and prepared with endotracheal tube for ventilation. The right femoral vein was cannulated to facilitate blood collections. Rats were administered the lipid nanoparticle formulation T763, which has the following components: ($C_{12}$-TR-A 45 mol %, squalane 45 mol %, DSPE-PEG2000 10 mol %).

Aeroneb® nebulizer and a controller (Aerogen, Dangan, Galway, Ireland) were used to produce aerosol of a mass median aerodynamic diameter (MMAD) between 2.5 μm and 4 μm and at a rate of 0.1 mL/min.

A SAR-830/AP Small Animal Ventilator (CWE Inc., Ardmore, Pa.) set up at ventilator tidal volume (VT) of 8 mL/kg, rate of 90 breaths/min was used to deliver nebulized test articles of volume 300 μL. The targeted dose was 6 ug/kg of Treprostinil equivalent.

The plasma level of treprostinil were significantly lower than when nanoparticle formulation T568 ($C_{12}$-TR 40 mol %, squalane 40 mol %, chol-PEG2k 10 mol %, DOPC 10 mol %), containing $C_{12}$-TR alkyl ester was used with the same dose. This suggests that the conversion rate of the amide prodrug is much slower than the rate for the ester prodrug of treprostinil.

While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

Patents, patent applications, patent application publications, journal articles and protocols referenced herein are incorporated by reference in their entireties, for all purposes.

The invention claimed is:

1. A method of treating pulmonary fibrosis in a patient in need thereof comprising administering to the patient via pulmonary administration, a composition comprising an effective amount of a compound of Formula (II), or a pharmaceutically acceptable salt thereof, Formula (II)

wherein $R_1$ is 0;
$R_2$ is tetradecyl, pentadecyl, hexadecyl, heptadecyl or octadecyl and
n is an integer from 0 to 5.

2. The method of claim 1, wherein pulmonary administration comprises administration via a metered dose inhaler, a dry powder inhaler or a nebulizer.

3. The method of claim 1, wherein the effective amount of the compound of Formula (II), or the pharmaceutically acceptable salt thereof, is administered once daily.

4. The method of claim 1, wherein the effective amount of the compound of Formula (II), or the pharmaceutically acceptable salt thereof, is administered two or more times daily.

5. The method of claim 1, wherein n is 1.

6. The method of claim 1, wherein $R_2$ is hexadecyl.

7. The method of claim 6, wherein n is 1.

8. The method of claim 1, wherein n is 1, $R_2$ is hexadecyl and pulmonary administration comprises administration via a nebulizer.

9. The method of claim 8, wherein the nebulizer is a vibrating mesh nebulizer.

10. The method of claim 1, wherein n is 1, $R_2$ is hexadecyl and pulmonary administration comprises administration via a dry powder inhaler.

11. The method of claim 1, wherein the composition comprises a lipid-polyethylene glycol (PEG) conjugate.

12. The method of claim 11, wherein the PEG is PEG-400, PEG500, PEG 1000, PEG2000, PEG3000, PEG4000 or PEG5000.

13. The method of claim 11, wherein the PEG is PEG2000.

14. The method of claim 11, wherein the lipid is cholesterol.

15. The method of claim 11, wherein the lipid is a phospholipid.

16. The method of claim 11, wherein the lipid is distearoyl phosphatidylethanolamine (DSPE), dimyristoyl phosphoethanol amine (DMPE) or distearoyl glycerol (DSG).

17. The method of claim 11, wherein the lipid-PEG conjugate is cholesterol-PEG2000, DSPE-PEG1000, DSPE-PEG2000 or DSG-PEG2000.

18. The method of claim 11, wherein the lipid-PEG conjugate is DSPE-PEG2000.

19. The method of claim 10, wherein the composition comprises a lipid-polyethylene glycol (PEG) conjugate.

20. The method of claim 19, wherein the PEG is PEG-400, PEG500, PEG 1000, PEG2000, PEG3000, PEG4000 or PEG5000.

21. The method of claim 19, wherein the PEG is PEG2000.

22. The method of claim 19, wherein the lipid is cholesterol.

23. The method of claim 19, wherein the lipid is a phospholipid.

24. The method of claim 23, wherein the lipid is distearoyl phosphatidylethanolamine (DSPE), dimyristoyl phosphoethanol amine (DMPE) or distearoyl glycerol (DSG).

25. The method of claim 19, wherein the lipid-PEG conjugate is cholesterol-PEG2000, DSPE-PEG1000, DSPE-PEG2000 or DSG-PEG2000.

26. The method of claim 19, wherein the lipid-PEG conjugate is DSPE-PEG2000.

27. The method of claim 1, wherein the composition comprises a hydrophobic additive.

28. The method of claim 27, wherein the hydrophobic additive is a hydrocarbon, a terpene or a hydrophobic lipid, alkyl ester, cholesteryl ester or an alkyl-glyceride.

29. The method of claim 27, wherein the hydrophobic additive is a terpene.

30. The method of claim 29, wherein the terpene is squalane.

31. The method of claim 27, wherein the composition comprises a lipid-polyethylene glycol (PEG) conjugate.

32. The method of claim 31, wherein the PEG is PEG400, PEG500, PEG 1000, PEG2000, PEG3000, PEG4000 or PEG-5000.

33. The method of claim 32, wherein the PEG is PEG-2000.

34. The method of claim 31, wherein the lipid is cholesterol.

35. The method of claim 31, wherein the lipid is a phospholipid.

36. The method of claim 35, wherein the lipid is distearoyl phosphatidylethanolamine (DSPE), dimyristoyl phosphoethanolamine (DMPE) or distearoyl glycerol (DSG).

37. The method of claim 31, wherein the lipid-PEG conjugate is cholesterol-PEG2000, DSPE-PEG 1000, DSPE-PEG2000 or DSG-PEG2000.

38. The method of claim 31, wherein the lipid-PEG conjugate is DSPE-PEG2000.

39. The method of claim 31, wherein the hydrophobic additive is a terpene.

40. The method of claim 39, wherein the terpene is squalane.

41. The method of claim 40, wherein the lipid-PEG conjugate is DSPE-PEG2000.

\* \* \* \* \*

UNITED STATES PATENT AND TRADEMARK OFFICE
CERTIFICATE OF CORRECTION

Page 1 of 2

PATENT NO. : 10,526,274 B2
APPLICATION NO. : 15/994574
DATED : January 7, 2020
INVENTOR(S) : Malinin et al.

It is certified that error appears in the above-identified patent and that said Letters Patent is hereby corrected as shown below:

On the Title Page

Item (63), please delete:
"Continuation of application No. 15/154,631, filed on May 13, 2016, now Pat. No. 10,010,518, which is a continuation of application No. 14/523,538, filed on Oct. 24, 2014, now Pat. No. 9,469,600, which is a continuation of application No. 61/895,680, filed on Oct. 25, 2013."
And replace with:
--Continuation of application No. 15/154,631, filed on May 13, 2016, now Pat. No. 10,010,518, which is a continuation of application No. 14/523,538, filed on Oct. 24, 2014, now Pat. No. 9,469,600.--.

Item (60), please delete:
"Provisional application No. 62/042,123, filed on Aug. 26, 2014, provisional application No. 62/028,758, filed on Jul. 24, 2014, provisional application No. 61/950,967, filed on Mar. 11, 2014, provisional application No. 61/910,703, filed on Dec. 2, 2013."
And replace with:
--Provisional application No. 62/042,123, filed on Aug. 26, 2014, provisional application No. 62/028,758, filed on Jul. 24, 2014, provisional application No. 61/950,967, filed on Mar. 11, 2014, provisional application No. 61/910,703, filed on Dec. 2, 2013, provisional application No. 61/895,680, filed on Oct. 25, 2013.--.

In the Claims

At Claim 1, Column 94, Line 16, please delete:
"wherein $R_1$ is 0;"
And replace with:
--wherein $R_1$ is O;--.

At Claim 12, Column 94, Lines 44-45, please delete:
"PEG-400, PEG500, PEG 1000,"

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*

And replace with:
--PEG400, PEG500, PEG1000,--.

At Claim 20, Column 94, Lines 63-64, please delete:
"PEG-400, PEG500, PEG 1000,"
And replace with:
--PEG400, PEG500, PEG1000,--.

At Claim 32, Column 96, Line 2, please delete:
"PEG 1000,"
And replace with:
--PEG1000,--.

At Claim 32, Column 96, Line 3, please delete:
"PEG-5000,"
And replace with:
--PEG5000,--.

At Claim 33, Column 96, Lines 4-5, please delete:
"PEG-2000,"
And replace with:
--PEG2000,--.

At Claim 37, Column 96, Line 14, please delete:
"DSPE-PEG 1000,"
And replace with:
--DSPE-PEG1000,--.